(12) United States Patent
Erickson

(10) Patent No.: US 9,872,894 B2
(45) Date of Patent: Jan. 23, 2018

(54) IMMUNOGENIC POLYPEPTIDE COCKTAIL FOR THE TREATMENT OF MEDULLARY THYROID CARCINOMA

(71) Applicant: Timothy Andrew Erickson, Beaverton, OR (US)

(72) Inventor: Timothy Andrew Erickson, Beaverton, OR (US)

(73) Assignee: Timothy Andrew Erickson, Beaverton, OR (US)

( * ) Notice: Subject to any disclaimer, the term of this patent is extended or adjusted under 35 U.S.C. 154(b) by 0 days.

(21) Appl. No.: 15/436,525

(22) Filed: Feb. 17, 2017

(65) Prior Publication Data

US 2017/0246274 A1 Aug. 31, 2017

Related U.S. Application Data

(60) Provisional application No. 62/299,941, filed on Feb. 25, 2016.

(51) Int. Cl.
*A61K 38/00* (2006.01)
*A61K 39/00* (2006.01)

(52) U.S. Cl.
CPC . *A61K 39/0011* (2013.01); *A61K 2039/55511* (2013.01); *A61K 2039/55561* (2013.01); *A61K 2039/55566* (2013.01); *A61K 2039/572* (2013.01); *A61K 2039/585* (2013.01)

(58) Field of Classification Search
None
See application file for complete search history.

(56) References Cited

U.S. PATENT DOCUMENTS 7,504,509 B2 * 3/2009 Ibrahim ............... C07D 471/04
546/113

OTHER PUBLICATIONS

M. Schott et al., "Immunotheraphy for Medullary Thyroid Carcinoma by Dendritic Cell Vaccination", The Journal of Clinical Endocrinology & Metabolism 86(10):4965-4969.

C. Papewalis et al., "Dendritic CellVaccinationwith Xenogenic Polypeptide Hormone InducesTumor Rejection in Neuroendocrine Cancer"; Clinical Cancer Research 2008;14(13) Jul. 1, 2008.

M. Schott et al., "Calcitonin-specific antitumor immunity in medullary thyroid carcinoma following dendritic cell vaccination", Cancer Immunol Immunother (2002) 51: 663-668.

M. Wuttke et al., "Amino Acid-Modified Calcitonin Immunization Induces Tumor Epitope-Specific Immunity in a Transgenic Mouse Model for Medullary Thyroid Carcinoma", Endocrinology 149(11):5627-5634.

* cited by examiner

*Primary Examiner* — Laura B Goddard
*Assistant Examiner* — Meera Natarajan

(57) ABSTRACT

Disclosed are immunogenic compositions that include one or more polypeptides that, when administered to a subject with adjuvant, elicit an immune response against medullary thyroid cancer. Disclosed are methods of eliciting an immune response and/or treating cancer, such as medullary thyroid carcinoma or other thyroid carcinomas.

6 Claims, 3 Drawing Sheets

SEQUENCE LISTING

<160> NUMBER OF SEQ ID NOS: 61

<210> SEQ ID NO 1
<211> LENGTH: 1114
<212> TYPE: PRT
<213> ORGANISM: Homo sapien

<400> SEQUENCE: 1

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

```
Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
```

```
            515                 520                 525
Glu Glu Cys Gly Gly Leu Gly Ser Pro Thr Gly Arg Cys Glu Trp Arg
            530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
            595                 600                 605

Cys Asn Cys Phe Pro Glu Glu Lys Cys Phe Cys Glu Pro Glu Asp
        610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
                675                 680                 685

Ser Ser Gly Ala Arg Arg Pro Ser Leu Asp Ser Met Glu Asn Gln Val
        690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
                740                 745                 750

Thr Thr Val Ala Val Lys Met Leu Lys Glu Asn Ala Ser Pro Ser Glu
            755                 760                 765

Leu Arg Asp Leu Leu Ser Glu Phe Asn Val Leu Lys Gln Val Asn His
        770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
        850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Thr Ala Ile Glu Ser Leu Phe Asp His Ile Tyr
            915                 920                 925

Thr Thr Gln Ser Asp Val Trp Ser Phe Gly Val Leu Leu Trp Glu Ile
        930                 935                 940
```

```
Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp  Ile Ser Lys Asp Leu  Glu Lys Met
        995                 1000                1005

Met Val  Lys Arg Arg Asp Tyr  Leu Asp Leu Ala Ala  Ser Thr Pro
    1010                1015                1020

Ser Asp  Ser Leu Ile Tyr Asp  Asp Gly Leu Ser Glu  Glu Glu Thr
    1025                1030                1035

Pro Leu  Val Asp Cys Asn Asn  Ala Pro Leu Pro Arg  Ala Leu Pro
    1040                1045                1050

Ser Thr  Trp Ile Glu Asn Lys  Leu Tyr Gly Met Ser  Asp Pro Asn
    1055                1060                1065

Trp Pro  Gly Glu Ser Pro Val  Pro Leu Thr Arg Ala  Asp Gly Thr
    1070                1075                1080

Asn Thr  Gly Phe Pro Arg Tyr  Pro Asn Asp Ser Val  Tyr Ala Asn
    1085                1090                1095

Trp Met  Leu Ser Pro Ser Ala  Ala Lys Leu Met Asp  Thr Phe Asp
    1100                1105                1110

Ser

<210> SEQ ID NO 2
<211> LENGTH: 21
<212> TYPE: PRT
<213> ORGANISM: artificial sequence
<220> FEATURE:
<223> OTHER INFORMATION: polypeptide encoding part of RET M918T mutation

<400> SEQUENCE: 2

Gln Gly Arg Ile Pro Val Lys Trp Thr Ala Ile Glu Ser Leu Phe Asp
1               5                   10                  15

His Ile Tyr Thr Thr
            20

<210> SEQ ID NO 3
<211> LENGTH: 30
<212> TYPE: PRT
<213> ORGANISM: artificial sequence
<220> FEATURE:
<223> OTHER INFORMATION: polypeptide encoding part of wild-type RET
      sequence

<400> SEQUENCE: 3

Arg Glu Asn Arg Pro Pro Gly Thr Phe His Gln Phe Arg Leu Leu Pro
1               5                   10                  15

Val Gln Phe Leu Cys Pro Asn Ile Ser Val Ala Tyr Arg Leu
            20                  25                  30

<210> SEQ ID NO 4
<211> LENGTH: 9
<212> TYPE: PRT
<213> ORGANISM: artificial sequence
<220> FEATURE:
<223> OTHER INFORMATION: Generic RET M918T 9-mer sequence with variable
      Xaa placeholder amino acids at anchor residue positions 2 and 9
<220> FEATURE:
<221> NAME/KEY: misc_feature
```

```
<222> LOCATION: (2)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 4

Pro Xaa Lys Trp Thr Ala Ile Glu Xaa
1               5

<210> SEQ ID NO 5
<211> LENGTH: 9
<212> TYPE: PRT
<213> ORGANISM: artificial sequence
<220> FEATURE:
<223> OTHER INFORMATION: RET M918T polypeptide with modified anchor
      residues

<400> SEQUENCE: 5

Pro Tyr Lys Trp Thr Ala Ile Glu Ile
1               5

<210> SEQ ID NO 6
<211> LENGTH: 9
<212> TYPE: PRT
<213> ORGANISM: artificial sequence
<220> FEATURE:
<223> OTHER INFORMATION: RET M918T polypeptide with modified anchor
      residues

<400> SEQUENCE: 6

Pro Thr Lys Trp Thr Ala Ile Glu Tyr
1               5

<210> SEQ ID NO 7
<211> LENGTH: 9
<212> TYPE: PRT
<213> ORGANISM: artificial sequence
<220> FEATURE:
<223> OTHER INFORMATION: RET M918T polypeptide with modified anchor
      residues

<400> SEQUENCE: 7

Arg Leu Pro Val Lys Trp Thr Ala Leu
1               5

<210> SEQ ID NO 8
<211> LENGTH: 189
<212> TYPE: PRT
<213> ORGANISM: Homo sapien

<400> SEQUENCE: 8

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95
```

```
Arg Glu Gln Ile Lys Arg Val Lys Asp Ser Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 9
<211> LENGTH: 189
<212> TYPE: PRT
<213> ORGANISM: Homo sapien

<400> SEQUENCE: 9

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 10
<211> LENGTH: 766
<212> TYPE: PRT
<213> ORGANISM: Homo sapien ce

<400> SEQUENCE: 10

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45
```

```
Asn Ile Lys Gln Met Ile Lys Leu Thr Gln Glu His Ile Glu Ala Leu
 50                  55                  60

Leu Asp Lys Phe Gly Gly Glu His Asn Pro Pro Ser Ile Tyr Leu Glu
 65                  70                  75                  80

Ala Tyr Glu Glu Tyr Thr Ser Lys Leu Asp Ala Leu Gln Gln Arg Glu
                 85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
                180                 185                 190

Glu Cys Cys Ala Val Tyr Arg Ile Gln Asp Gly Glu Lys Lys Pro Ile
            195                 200                 205

Gly Trp Asp Thr Asp Ile Ser Trp Leu Thr Gly Glu Glu Leu His Val
        210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
                275                 280                 285

Leu Phe Val Ser Lys Phe Phe Glu His His Pro Ile Pro Gln Glu Glu
290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
                355                 360                 365

Val His Ile Asn Thr Ile Glu Pro Val Asn Ile Asp Asp Leu Ile Arg
                370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
                450                 455                 460
```

```
Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 11
<211> LENGTH: 29
<212> TYPE: PRT
<213> ORGANISM: artificial sequence
<220> FEATURE:
<223> OTHER INFORMATION: HRAS sequence with variable Xaa mutant amino
      acid residue
<220> FEATURE:
<221> NAME/KEY: misc_feature
<222> LOCATION: (15)..(15)
<223> OTHER INFORMATION: Xaa can be any naturally occurring amino acid

<400> SEQUENCE: 11

Asp Gly Glu Thr Cys Leu Leu Asp Ile Leu Asp Thr Ala Gly Xaa Glu
1               5                   10                  15

Glu Tyr Ser Ala Met Arg Asp Gln Tyr Met Arg Thr Gly
            20                  25
```

```
<210> SEQ ID NO 12
<211> LENGTH: 29
<212> TYPE: PRT
<213> ORGANISM: artificial sequence
<220> FEATURE:
<223> OTHER INFORMATION: polypeptide encoding the HRAS Q61R mutation

<400> SEQUENCE: 12

Asp Gly Glu Thr Cys Leu Leu Asp Ile Leu Asp Thr Ala Gly Arg Glu
1               5                   10                  15

Glu Tyr Ser Ala Met Arg Asp Gln Tyr Met Arg Thr Gly
            20                  25

<210> SEQ ID NO 13
<211> LENGTH: 29
<212> TYPE: PRT
<213> ORGANISM: artificial sequence
<220> FEATURE:
<223> OTHER INFORMATION: polypeptide encoding the HRAS Q61K mutation

<400> SEQUENCE: 13

Asp Gly Glu Thr Cys Leu Leu Asp Ile Leu Asp Thr Ala Gly Lys Glu
1               5                   10                  15

Glu Tyr Ser Ala Met Arg Asp Gln Tyr Met Arg Thr Gly
            20                  25

<210> SEQ ID NO 14
<211> LENGTH: 25
<212> TYPE: PRT
<213> ORGANISM: artificial sequence
<220> FEATURE:
<223> OTHER INFORMATION: polypeptide encoding the HRAS G13R mutation

<400> SEQUENCE: 14

Met Thr Glu Tyr Lys Leu Val Val Val Gly Ala Gly Arg Val Gly Lys
1               5                   10                  15

Ser Ala Leu Thr Ile Gln Leu Ile Gln
            20                  25

<210> SEQ ID NO 15
<211> LENGTH: 29
<212> TYPE: PRT
<213> ORGANISM: artificial sequence
<220> FEATURE:
<223> OTHER INFORMATION: polypeptide encoding the HRAS K117N mutation

<400> SEQUENCE: 15

Val Lys Asp Ser Asp Asp Val Pro Met Val Leu Val Gly Asn Asn Cys
1               5                   10                  15

Asp Leu Ala Ala Arg Thr Val Glu Ser Arg Gln Ala Gln
            20                  25

<210> SEQ ID NO 16
<211> LENGTH: 29
<212> TYPE: PRT
<213> ORGANISM: artificial sequence
<220> FEATURE:
<223> OTHER INFORMATION: polypeptide encoding the HRAS A146V mutation

<400> SEQUENCE: 16

Asp Leu Ala Arg Ser Tyr Gly Ile Pro Phe Ile Glu Thr Ser Val Lys
1               5                   10                  15

Thr Arg Gln Arg Val Glu Asp Ala Phe Tyr Thr Leu Val
            20                  25
```

```
<210> SEQ ID NO 17
<211> LENGTH: 23
<212> TYPE: PRT
<213> ORGANISM: artificial sequence
<220> FEATURE:
<223> OTHER INFORMATION: polypeptide encoding generic KRAS mutation at
      position twelve with Xaa as mutant amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 17

Met Thr Glu Tyr Lys Leu Val Val Val Gly Ala Xaa Gly Val Gly Lys
1               5                   10                  15

Ser Ala Leu Thr Ile Gln Leu
            20

<210> SEQ ID NO 18
<211> LENGTH: 23
<212> TYPE: PRT
<213> ORGANISM: artificial sequence
<220> FEATURE:
<223> OTHER INFORMATION: polypeptide encoding the KRAS G12V mutation

<400> SEQUENCE: 18

Met Thr Glu Tyr Lys Leu Val Val Val Gly Ala Val Gly Val Gly Lys
1               5                   10                  15

Ser Ala Leu Thr Ile Gln Leu
            20

<210> SEQ ID NO 19
<211> LENGTH: 23
<212> TYPE: PRT
<213> ORGANISM: artificial sequence
<220> FEATURE:
<223> OTHER INFORMATION: polypeptide encoding the KRAS G12R mutation

<400> SEQUENCE: 19

Met Thr Glu Tyr Lys Leu Val Val Val Gly Ala Arg Gly Val Gly Lys
1               5                   10                  15

Ser Ala Leu Thr Ile Gln Leu
            20

<210> SEQ ID NO 20
<211> LENGTH: 28
<212> TYPE: PRT
<213> ORGANISM: artificial sequence
<220> FEATURE:
<223> OTHER INFORMATION: polypeptide encoding generic BRAF mutation at
      position 600 with Xaa as mutant amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 20

Glu Asp Leu Thr Val Lys Ile Gly Asp Phe Gly Leu Ala Thr Xaa Lys
1               5                   10                  15

Ser Arg Trp Ser Gly Ser His Gln Phe Glu Gln Leu
            20                  25

<210> SEQ ID NO 21
<211> LENGTH: 28
<212> TYPE: PRT
<213> ORGANISM: artificial sequence
```

```
<220> FEATURE:
<223> OTHER INFORMATION: polypeptide encoding the BRAF V600E mutation

<400> SEQUENCE: 21

Glu Asp Leu Thr Val Lys Ile Gly Asp Phe Gly Leu Ala Thr Glu Lys
1               5                   10                  15

Ser Arg Trp Ser Gly Ser His Gln Phe Glu Gln Leu
            20                  25

<210> SEQ ID NO 22
<211> LENGTH: 28
<212> TYPE: PRT
<213> ORGANISM: artificial sequence
<220> FEATURE:
<223> OTHER INFORMATION: polypeptide encoding the BRAF V600K mutation

<400> SEQUENCE: 22

Glu Asp Leu Thr Val Lys Ile Gly Asp Phe Gly Leu Ala Thr Lys Lys
1               5                   10                  15

Ser Arg Trp Ser Gly Ser His Gln Phe Glu Gln Leu
            20                  25

<210> SEQ ID NO 23
<211> LENGTH: 9
<212> TYPE: PRT
<213> ORGANISM: artificial sequence
<220> FEATURE:
<223> OTHER INFORMATION: Generic BRAF 9-mer sequence with variable Xaa
      placeholder amino acids at positions 2, 5 and 9
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 23

Gly Xaa Ala Thr Xaa Lys Ser Arg Xaa
1               5

<210> SEQ ID NO 24
<211> LENGTH: 9
<212> TYPE: PRT
<213> ORGANISM: artificial sequence
<220> FEATURE:
<223> OTHER INFORMATION: HLA-A1 restricted BRAF 9-mer sequence with
      variable Xaa placeholder amino acids at position 5
<220> FEATURE:
<221> NAME/KEY: misc_feature
<222> LOCATION: (5)..(5)
<223> OTHER INFORMATION: Xaa can be any naturally occurring amino acid

<400> SEQUENCE: 24

Gly Thr Ala Thr Xaa Lys Ser Arg Tyr
1               5

<210> SEQ ID NO 25
<211> LENGTH: 9
<212> TYPE: PRT
<213> ORGANISM: artificial sequence
<220> FEATURE:
<223> OTHER INFORMATION: HLA-A2 restricted BRAF 9-mer sequence with
      variable Xaa placeholder amino acids at position 5
```

-continued

```
<220> FEATURE:
<221> NAME/KEY: misc_feature
<222> LOCATION: (5)..(5)
<223> OTHER INFORMATION: Xaa can be any naturally occurring amino acid

<400> SEQUENCE: 25

Gly Leu Ala Thr Xaa Lys Ser Arg Leu
1               5

<210> SEQ ID NO 26
<211> LENGTH: 9
<212> TYPE: PRT
<213> ORGANISM: artificial sequence
<220> FEATURE:
<223> OTHER INFORMATION: HLA-A24 restricted BRAF 9-mer sequence with
      variable Xaa placeholder amino acids at position 5
<220> FEATURE:
<221> NAME/KEY: misc_feature
<222> LOCATION: (5)..(5)
<223> OTHER INFORMATION: Xaa can be any naturally occurring amino acid

<400> SEQUENCE: 26

Gly Tyr Ala Thr Xaa Lys Ser Arg Phe
1               5

<210> SEQ ID NO 27
<211> LENGTH: 32
<212> TYPE: PRT
<213> ORGANISM: Homo sapien

<400> SEQUENCE: 27

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
                20                  25                  30

<210> SEQ ID NO 28
<211> LENGTH: 32
<212> TYPE: PRT
<213> ORGANISM: artificial sequence
<220> FEATURE:
<223> OTHER INFORMATION: amino-acid modified calcitonin

<400> SEQUENCE: 28

Cys Thr Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Ala Ala Pro
                20                  25                  30

<210> SEQ ID NO 29
<211> LENGTH: 700
<212> TYPE: PRT
<213> ORGANISM: Homo sapien

<400> SEQUENCE: 29

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
                20                  25                  30

Thr Ala Lys Leu Thr Ile Glu Ser Thr Pro Phe Asn Val Ala Glu Gly
            35                  40                  45

Lys Glu Val Leu Leu Leu Val His Asn Leu Pro Gln His Leu Phe Gly
        50                  55                  60

Tyr Ser Trp Tyr Lys Gly Glu Arg Val Asp Gly Asn Arg Gln Ile Ile
```

```
            65                  70                  75                  80
Gly Tyr Val Ile Gly Thr Gln Gln Ala Thr Pro Gly Pro Ala Tyr Ser
                    85                  90                  95
Gly Arg Glu Ile Ile Tyr Pro Asn Ala Ser Leu Leu Ile Gln Asn Ile
                   100                 105                 110
Ile Gln Asn Asp Thr Gly Phe Tyr Thr Leu His Val Ile Lys Ser Asp
                   115                 120                 125
Leu Val Asn Glu Glu Ala Thr Gly Gln Phe Arg Val Tyr Pro Glu Leu
                   130                 135                 140
Pro Lys Pro Ser Ile Ser Ser Asn Asn Ser Lys Pro Val Glu Asp Lys
145                 150                 155                 160
Asp Ala Val Ala Phe Thr Cys Glu Pro Glu Thr Gln Asp Ala Thr Tyr
                        165                 170                 175
Leu Trp Trp Val Asn Asn Gln Ser Leu Pro Val Ser Pro Arg Leu Gln
                   180                 185                 190
Leu Ser Asn Gly Asn Arg Thr Leu Thr Leu Phe Asn Val Thr Arg Asn
                   195                 200                 205
Asp Thr Ala Ser Tyr Lys Cys Glu Thr Gln Asn Pro Val Ser Ala Arg
                   210                 215                 220
Arg Ser Asp Ser Val Ile Leu Asn Val Leu Tyr Gly Pro Asp Ala Pro
225                 230                 235                 240
Thr Ile Ser Pro Leu Asn Thr Ser Tyr Arg Ser Gly Glu Asn Leu Asn
                   245                 250                 255
Leu Ser Cys His Ala Ala Ser Asn Pro Pro Ala Gln Tyr Ser Trp Phe
                   260                 265                 270
Val Asn Gly Thr Phe Gln Gln Ser Thr Gln Glu Leu Phe Ile Pro Asn
                   275                 280                 285
Ile Thr Val Asn Asn Ser Gly Ser Tyr Thr Cys Gln Ala His Asn Ser
                   290                 295                 300
Asp Thr Gly Leu Asn Arg Thr Thr Val Thr Thr Ile Thr Val Tyr Ala
305                 310                 315                 320
Glu Pro Pro Lys Pro Phe Ile Thr Ser Asn Asn Ser Asn Pro Val Glu
                   325                 330                 335
Asp Glu Asp Ala Val Ala Leu Thr Cys Glu Pro Glu Ile Gln Asn Thr
                   340                 345                 350
Thr Tyr Leu Trp Trp Val Asn Asn Gln Ser Leu Pro Val Ser Pro Arg
                   355                 360                 365
Leu Gln Leu Ser Asn Asp Asn Arg Thr Leu Thr Leu Leu Ser Val Thr
                   370                 375                 380
Arg Asn Asp Val Gly Pro Tyr Glu Cys Gly Ile Gln Asn Lys Leu Ser
385                 390                 395                 400
Val Asp His Ser Asp Pro Val Ile Leu Asn Val Leu Tyr Gly Pro Asp
                        405                 410                 415
Asp Pro Thr Ile Ser Pro Ser Tyr Thr Tyr Tyr Arg Pro Gly Val Asn
                   420                 425                 430
Leu Ser Leu Ser Cys His Ala Ala Ser Asn Pro Pro Ala Gln Tyr Ser
                   435                 440                 445
Trp Leu Ile Asp Gly Asn Ile Gln Gln His Thr Gln Glu Leu Phe Ile
                   450                 455                 460
Ser Asn Ile Thr Glu Lys Asn Ser Gly Leu Tyr Thr Cys Gln Ala Asn
465                 470                 475                 480
Asn Ser Ala Ser Gly His Ser Arg Thr Thr Val Lys Thr Ile Thr Val
                   485                 490                 495
```

-continued

Ser Ala Glu Leu Pro Lys Pro Ser Ile Ser Ser Asn Asn Ser Lys Pro
                500                 505                 510

Val Glu Asp Lys Asp Ala Val Ala Phe Thr Cys Glu Pro Glu Ala Gln
            515                 520                 525

Asn Thr Thr Tyr Leu Trp Trp Val Asn Gly Gln Ser Leu Pro Val Ser
        530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala
    690                 695                 700

<210> SEQ ID NO 30
<211> LENGTH: 30
<212> TYPE: PRT
<213> ORGANISM: artificial sequence
<220> FEATURE:
<223> OTHER INFORMATION: polypeptide encoding CEACAM5 amino acids
      652-681

<400> SEQUENCE: 30

Thr Tyr Ala Cys Phe Val Ser Asn Leu Ala Thr Gly Arg Asn Asn Ser
1               5                   10                  15

Ile Val Lys Ser Ile Thr Val Ser Ala Ser Gly Thr Ser Pro
            20                  25                  30

<210> SEQ ID NO 31
<211> LENGTH: 28
<212> TYPE: PRT
<213> ORGANISM: artificial sequence
<220> FEATURE:
<223> OTHER INFORMATION: polypeptide encoding CEACAM5 amino acids
      108-135

<400> SEQUENCE: 31

Leu Ile Gln Asn Ile Ile Gln Asn Asp Thr Gly Phe Tyr Thr Leu His
1               5                   10                  15

Val Ile Lys Ser Asp Leu Val Asn Glu Glu Ala Thr
            20                  25

<210> SEQ ID NO 32
<211> LENGTH: 9
<212> TYPE: PRT
<213> ORGANISM: artificial sequence
<220> FEATURE:
<223> OTHER INFORMATION: polypeptide encoding CEACAM5 amino acids
      467-475

<400> SEQUENCE: 32

Ile Thr Glu Lys Asn Ser Gly Leu Tyr
1               5

<210> SEQ ID NO 33
<211> LENGTH: 1255
<212> TYPE: PRT
<213> ORGANISM: Homo sapien

<400> SEQUENCE: 33

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
                115                 120                 125

Gly Ser Thr Ala Pro Pro Ala His Gly Val Thr Ser Ala Pro Asp Thr
            130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
                180                 185                 190

Pro Pro Ala His Gly Val Thr Ser Ala Pro Asp Thr Arg Pro Ala Pro
            195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
                260                 265                 270

Pro Pro Ala His Gly Val Thr Ser Ala Pro Asp Thr Arg Pro Ala Pro
            275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

```
Gly Val Thr Ser Ala Pro Asp Thr Arg Pro Ala Pro Gly Ser Thr Ala
            340                 345                 350
Pro Pro Ala His Gly Val Thr Ser Ala Pro Asp Thr Arg Pro Ala Pro
        355                 360                 365
Gly Ser Thr Ala Pro Pro Ala His Gly Val Thr Ser Ala Pro Asp Thr
    370                 375                 380
Arg Pro Ala Pro Gly Ser Thr Ala Pro Pro Ala His Gly Val Thr Ser
385                 390                 395                 400
Ala Pro Asp Thr Arg Pro Ala Pro Gly Ser Thr Ala Pro Pro Ala His
            405                 410                 415
Gly Val Thr Ser Ala Pro Asp Thr Arg Pro Ala Pro Gly Ser Thr Ala
        420                 425                 430
Pro Pro Ala His Gly Val Thr Ser Ala Pro Asp Thr Arg Pro Ala Pro
        435                 440                 445
Gly Ser Thr Ala Pro Pro Ala His Gly Val Thr Ser Ala Pro Asp Thr
    450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
            485                 490                 495
Gly Val Thr Ser Ala Pro Asp Thr Arg Pro Ala Pro Gly Ser Thr Ala
        500                 505                 510
Pro Pro Ala His Gly Val Thr Ser Ala Pro Asp Thr Arg Pro Ala Pro
        515                 520                 525
Gly Ser Thr Ala Pro Pro Ala His Gly Val Thr Ser Ala Pro Asp Thr
    530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
            565                 570                 575
Gly Val Thr Ser Ala Pro Asp Thr Arg Pro Ala Pro Gly Ser Thr Ala
        580                 585                 590
Pro Pro Ala His Gly Val Thr Ser Ala Pro Asp Thr Arg Pro Ala Pro
        595                 600                 605
Gly Ser Thr Ala Pro Pro Ala His Gly Val Thr Ser Ala Pro Asp Thr
    610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
            645                 650                 655
Gly Val Thr Ser Ala Pro Asp Thr Arg Pro Ala Pro Gly Ser Thr Ala
        660                 665                 670
Pro Pro Ala His Gly Val Thr Ser Ala Pro Asp Thr Arg Pro Ala Pro
        675                 680                 685
Gly Ser Thr Ala Pro Pro Ala His Gly Val Thr Ser Ala Pro Asp Thr
    690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
            725                 730                 735
Gly Val Thr Ser Ala Pro Asp Thr Arg Pro Ala Pro Gly Ser Thr Ala
        740                 745                 750
```

```
Pro Pro Ala His Gly Val Thr Ser Ala Pro Asp Thr Arg Pro Ala Pro
        755                 760                 765
Gly Ser Thr Ala Pro Pro Ala His Gly Val Thr Ser Ala Pro Asp Thr
    770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
            805                 810                 815
Gly Val Thr Ser Ala Pro Asp Thr Arg Pro Ala Pro Gly Ser Thr Ala
        820                 825                 830
Pro Pro Ala His Gly Val Thr Ser Ala Pro Asp Thr Arg Pro Ala Pro
        835                 840                 845
Gly Ser Thr Ala Pro Pro Ala His Gly Val Thr Ser Ala Pro Asp Thr
    850                 855                 860
Arg Pro Ala Pro Gly Ser Thr Ala Pro Pro Ala His Gly Val Thr Ser
865                 870                 875                 880
Ala Pro Asp Thr Arg Pro Ala Pro Gly Ser Thr Ala Pro Pro Ala His
            885                 890                 895
Gly Val Thr Ser Ala Pro Asp Thr Arg Pro Ala Pro Gly Ser Thr Ala
        900                 905                 910
Pro Pro Ala His Gly Val Thr Ser Ala Pro Asp Thr Arg Pro Ala Pro
        915                 920                 925
Gly Ser Thr Ala Pro Pro Ala His Gly Val Thr Ser Ala Pro Asp Asn
    930                 935                 940
Arg Pro Ala Leu Gly Ser Thr Ala Pro Pro Val His Asn Val Thr Ser
945                 950                 955                 960
Ala Ser Gly Ser Ala Ser Gly Ser Ala Ser Thr Leu Val His Asn Gly
            965                 970                 975
Thr Ser Ala Arg Ala Thr Thr Thr Pro Ala Ser Lys Ser Thr Pro Phe
            980                 985                 990
Ser Ile Pro Ser His His Ser Asp Thr Pro Thr Thr Leu Ala Ser His
        995                 1000                1005
Ser Thr Lys Thr Asp Ala Ser Ser Thr His His Ser Ser Val Pro
    1010                1015                1020
Pro Leu Thr Ser Ser Asn His Ser Thr Ser Pro Gln Leu Ser Thr
    1025                1030                1035
Gly Val Ser Phe Phe Phe Leu Ser Phe His Ile Ser Asn Leu Gln
    1040                1045                1050
Phe Asn Ser Ser Leu Glu Asp Pro Ser Thr Asp Tyr Tyr Gln Glu
    1055                1060                1065
Leu Gln Arg Asp Ile Ser Glu Met Phe Leu Gln Ile Tyr Lys Gln
    1070                1075                1080
Gly Gly Phe Leu Gly Leu Ser Asn Ile Lys Phe Arg Pro Gly Ser
    1085                1090                1095
Val Val Val Gln Leu Thr Leu Ala Phe Arg Glu Gly Thr Ile Asn
    1100                1105                1110
Val His Asp Val Glu Thr Gln Phe Asn Gln Tyr Lys Thr Glu Ala
    1115                1120                1125
Ala Ser Arg Tyr Asn Leu Thr Ile Ser Asp Val Ser Val Ser Asp
    1130                1135                1140
Val Pro Phe Pro Phe Ser Ala Gln Ser Gly Ala Gly Val Pro Gly
    1145                1150                1155
Trp Gly Ile Ala Leu Leu Val Leu Val Cys Val Leu Val Ala Leu
```

```
                    1160                1165                1170
Ala  Ile  Val  Tyr  Leu  Ile  Ala  Leu  Ala  Val  Cys  Gln  Cys  Arg  Arg
          1175                1180                1185

Lys  Asn  Tyr  Gly  Gln  Leu  Asp  Ile  Phe  Pro  Ala  Arg  Asp  Thr  Tyr
          1190                1195                1200

His  Pro  Met  Ser  Glu  Tyr  Pro  Thr  Tyr  His  Thr  His  Gly  Arg  Tyr
          1205                1210                1215

Val  Pro  Pro  Ser  Ser  Thr  Asp  Arg  Ser  Pro  Tyr  Glu  Lys  Val  Ser
          1220                1225                1230

Ala  Gly  Asn  Gly  Gly  Ser  Ser  Leu  Ser  Tyr  Thr  Asn  Pro  Ala  Val
          1235                1240                1245

Ala  Ala  Thr  Ser  Ala  Asn  Leu
          1250                1255

<210> SEQ ID NO 34
<211> LENGTH: 2169
<212> TYPE: PRT
<213> ORGANISM: Homo sapien

<400> SEQUENCE: 34

Met  Lys  Gly  Ala  Arg  Trp  Arg  Arg  Val  Pro  Trp  Val  Ser  Leu  Ser  Cys
1                 5                   10                  15

Leu  Cys  Leu  Cys  Leu  Leu  Pro  His  Val  Val  Pro  Gly  Thr  Thr  Glu  Asp
                20                  25                  30

Thr  Leu  Ile  Thr  Gly  Ser  Lys  Thr  Ala  Ala  Pro  Val  Thr  Ser  Thr  Gly
            35                  40                  45

Ser  Thr  Thr  Ala  Thr  Leu  Glu  Gly  Gln  Ser  Thr  Ala  Ala  Ser  Ser  Arg
    50                  55                  60

Thr  Ser  Asn  Gln  Asp  Ile  Ser  Ala  Ser  Ser  Gln  Asn  His  Gln  Thr  Lys
65                  70                  75                  80

Ser  Thr  Glu  Thr  Thr  Ser  Lys  Ala  Gln  Thr  Asp  Thr  Leu  Thr  Gln  Met
                85                  90                  95

Met  Thr  Ser  Thr  Leu  Phe  Ser  Ser  Pro  Ser  Val  His  Asn  Val  Met  Glu
            100                 105                 110

Thr  Val  Thr  Gln  Glu  Thr  Ala  Pro  Pro  Asp  Glu  Met  Thr  Thr  Ser  Phe
        115                 120                 125

Pro  Ser  Ser  Val  Thr  Asn  Thr  Leu  Met  Met  Thr  Ser  Lys  Thr  Ile  Thr
130                 135                 140

Met  Thr  Thr  Ser  Thr  Asp  Ser  Thr  Leu  Gly  Asn  Thr  Glu  Glu  Thr  Ser
145                 150                 155                 160

Thr  Ala  Gly  Thr  Glu  Ser  Ser  Thr  Pro  Val  Thr  Ser  Ala  Val  Ser  Ile
                165                 170                 175

Thr  Ala  Gly  Gln  Glu  Gly  Gln  Ser  Arg  Thr  Thr  Ser  Trp  Arg  Thr  Ser
            180                 185                 190

Ile  Gln  Asp  Thr  Ser  Ala  Ser  Ser  Gln  Asn  His  Trp  Thr  Arg  Ser  Thr
        195                 200                 205

Gln  Thr  Thr  Arg  Glu  Ser  Gln  Thr  Ser  Thr  Leu  Thr  His  Arg  Thr  Thr
    210                 215                 220

Ser  Thr  Pro  Ser  Phe  Ser  Pro  Ser  Val  His  Asn  Val  Thr  Gly  Thr  Val
225                 230                 235                 240

Ser  Gln  Lys  Thr  Ser  Pro  Ser  Gly  Glu  Thr  Ala  Thr  Ser  Ser  Leu  Cys
                245                 250                 255

Ser  Val  Thr  Asn  Thr  Ser  Met  Met  Thr  Ser  Glu  Lys  Ile  Thr  Val  Thr
            260                 265                 270
```

```
Thr Ser Thr Gly Ser Thr Leu Gly Asn Pro Gly Glu Thr Ser Ser Val
            275                 280                 285

Pro Val Thr Gly Ser Leu Met Pro Val Thr Ser Ala Ala Leu Val Thr
290                 295                 300

Val Asp Pro Glu Gly Gln Ser Pro Ala Thr Phe Ser Arg Thr Ser Thr
305                 310                 315                 320

Gln Asp Thr Thr Ala Phe Ser Lys Asn His Gln Thr Gln Ser Val Glu
                325                 330                 335

Thr Thr Arg Val Ser Gln Ile Asn Thr Leu Asn Thr Leu Thr Pro Val
            340                 345                 350

Thr Thr Ser Thr Val Leu Ser Ser Pro Ser Gly Phe Asn Pro Ser Gly
        355                 360                 365

Thr Val Ser Gln Glu Thr Phe Pro Ser Gly Glu Thr Thr Ile Ser Ser
370                 375                 380

Pro Ser Ser Val Ser Asn Thr Phe Leu Val Thr Ser Lys Val Phe Arg
385                 390                 395                 400

Met Pro Ile Ser Arg Asp Ser Thr Leu Gly Asn Thr Glu Glu Thr Ser
                405                 410                 415

Leu Ser Val Ser Gly Thr Ile Ser Ala Ile Thr Ser Lys Val Ser Thr
            420                 425                 430

Ile Trp Trp Ser Asp Thr Leu Ser Thr Ala Leu Ser Pro Ser Ser Leu
        435                 440                 445

Pro Pro Lys Ile Ser Thr Ala Phe His Thr Gln Gln Ser Glu Gly Ala
        450                 455                 460

Glu Thr Thr Gly Arg Pro His Glu Arg Ser Ser Phe Ser Pro Gly Val
465                 470                 475                 480

Ser Gln Glu Ile Phe Thr Leu His Glu Thr Thr Thr Trp Pro Ser Ser
                485                 490                 495

Phe Ser Ser Lys Gly His Thr Thr Trp Ser Gln Thr Glu Leu Pro Ser
                500                 505                 510

Thr Ser Thr Gly Ala Ala Thr Arg Leu Val Thr Gly Asn Pro Ser Thr
            515                 520                 525

Arg Ala Ala Gly Thr Ile Pro Arg Val Pro Ser Lys Val Ser Ala Ile
530                 535                 540

Gly Glu Pro Gly Glu Pro Thr Thr Tyr Ser Ser His Ser Thr Thr Leu
545                 550                 555                 560

Pro Lys Thr Thr Gly Ala Gly Ala Gln Thr Gln Trp Thr Gln Glu Thr
                565                 570                 575

Gly Thr Thr Gly Glu Ala Leu Leu Ser Ser Pro Ser Tyr Ser Val Ile
            580                 585                 590

Gln Met Ile Lys Thr Ala Thr Ser Pro Ser Ser Ser Pro Met Leu Asp
        595                 600                 605

Arg His Thr Ser Gln Gln Ile Thr Thr Ala Pro Ser Thr Asn His Ser
        610                 615                 620

Thr Ile His Ser Thr Ser Thr Ser Pro Gln Glu Ser Pro Ala Val Ser
625                 630                 635                 640

Gln Arg Gly His Thr Arg Ala Pro Gln Thr Thr Gln Glu Ser Gln Thr
                645                 650                 655

Thr Arg Ser Val Ser Pro Met Thr Asp Thr Lys Thr Val Thr Thr Pro
            660                 665                 670

Gly Ser Ser Phe Thr Ala Ser Gly His Ser Pro Ser Glu Ile Val Pro
        675                 680                 685

Gln Asp Ala Pro Thr Ile Ser Ala Ala Thr Thr Phe Ala Pro Ala Pro
```

```
                690                 695                 700
Thr Gly Asn Gly His Thr Thr Gln Ala Pro Thr Thr Ala Leu Gln Ala
705                 710                 715                 720

Ala Pro Ser Ser His Asp Ala Thr Leu Gly Pro Ser Gly Thr Ser
                725                 730                 735

Leu Ser Lys Thr Gly Ala Leu Thr Leu Ala Asn Ser Val Val Ser Thr
                740                 745                 750

Pro Gly Gly Pro Glu Gly Gln Trp Thr Ser Ala Ser Ala Ser Thr Ser
                755                 760                 765

Pro Asp Thr Ala Ala Ala Met Thr His Thr His Gln Ala Glu Ser Thr
770                 775                 780

Glu Ala Ser Gly Gln Thr Gln Thr Ser Glu Pro Ala Ser Ser Gly Ser
785                 790                 795                 800

Arg Thr Thr Ser Ala Gly Thr Ala Thr Pro Ser Ser Ser Gly Ala Ser
                805                 810                 815

Gly Thr Thr Pro Ser Gly Ser Glu Gly Ile Ser Thr Ser Gly Glu Thr
                820                 825                 830

Thr Arg Phe Ser Ser Asn Pro Ser Arg Asp Ser His Thr Thr Gln Ser
                835                 840                 845

Thr Thr Glu Leu Leu Ser Ala Ser Ala Ser His Gly Ala Ile Pro Val
                850                 855                 860

Ser Thr Gly Met Ala Ser Ser Ile Val Pro Gly Thr Phe His Pro Thr
865                 870                 875                 880

Leu Ser Glu Ala Ser Thr Ala Gly Arg Pro Thr Gly Gln Ser Ser Pro
                885                 890                 895

Thr Ser Pro Ser Ala Ser Pro Gln Glu Thr Ala Ala Ile Ser Arg Met
                900                 905                 910

Ala Gln Thr Gln Arg Thr Gly Thr Ser Arg Gly Ser Asp Thr Ile Ser
                915                 920                 925

Leu Ala Ser Gln Ala Thr Asp Thr Phe Ser Thr Val Pro Pro Thr Pro
                930                 935                 940

Pro Ser Ile Thr Ser Ser Gly Leu Thr Ser Pro Gln Thr Gln Thr His
945                 950                 955                 960

Thr Leu Ser Pro Ser Gly Ser Gly Lys Thr Phe Thr Thr Ala Leu Ile
                965                 970                 975

Ser Asn Ala Thr Pro Leu Pro Val Thr Ser Thr Ser Ser Ala Ser Thr
                980                 985                 990

Gly His Ala Thr Pro Leu Ala Val  Ser Ser Ala Thr Ser  Ala Ser Thr
                995                 1000                1005

Val Ser  Ser Asp Ser Pro Leu  Lys Met Glu Thr Ser  Gly Met Thr
                1010                1015                1020

Thr Pro  Ser Leu Lys Thr Asp  Gly Gly Arg Arg Thr  Ala Thr Ser
                1025                1030                1035

Pro Pro  Pro Thr Thr Ser Gln  Thr Ile Ile Ser Thr  Ile Pro Ser
                1040                1045                1050

Thr Ala  Met His Thr Arg Ser  Thr Ala Ala Pro Ile  Pro Ile Leu
                1055                1060                1065

Pro Glu  Arg Gly Val Ser Leu  Phe Pro Tyr Gly Ala  Gly Ala Gly
                1070                1075                1080

Asp Leu  Glu Phe Val Arg Arg  Thr Val Asp Phe Thr  Ser Pro Leu
                1085                1090                1095

Phe Lys  Pro Ala Thr Gly Phe  Pro Leu Gly Ser Ser  Leu Arg Asp
                1100                1105                1110
```

-continued

Ser Leu Tyr Phe Thr Asp Asn Gly Gln Ile Ile Phe Pro Glu Ser
1115                 1120                1125

Asp Tyr Gln Ile Phe Ser Tyr Pro Asn Pro Leu Pro Thr Gly Phe
1130                 1135                1140

Thr Gly Arg Asp Pro Val Ala Leu Val Ala Pro Phe Trp Asp Asp
1145                 1150                1155

Ala Asp Phe Ser Thr Gly Arg Gly Thr Thr Phe Tyr Gln Glu Tyr
1160                 1165                1170

Glu Thr Phe Tyr Gly Glu His Ser Leu Leu Val Gln Gln Ala Glu
1175                 1180                1185

Ser Trp Ile Arg Lys Met Thr Asn Asn Gly Gly Tyr Lys Ala Arg
1190                 1195                1200

Trp Ala Leu Lys Val Thr Trp Val Asn Ala His Ala Tyr Pro Ala
1205                 1210                1215

Gln Trp Thr Leu Gly Ser Asn Thr Tyr Gln Ala Ile Leu Ser Thr
1220                 1225                1230

Asp Gly Ser Arg Ser Tyr Ala Leu Phe Leu Tyr Gln Ser Gly Gly
1235                 1240                1245

Met Gln Trp Asp Val Ala Gln Arg Ser Gly Asn Pro Val Leu Met
1250                 1255                1260

Gly Phe Ser Ser Gly Asp Gly Tyr Phe Glu Asn Ser Pro Leu Met
1265                 1270                1275

Ser Gln Pro Val Trp Glu Arg Tyr Arg Pro Asp Arg Phe Leu Asn
1280                 1285                1290

Ser Asn Ser Gly Leu Gln Gly Leu Gln Phe Tyr Arg Leu His Arg
1295                 1300                1305

Glu Glu Arg Pro Asn Tyr Arg Leu Glu Cys Leu Gln Trp Leu Lys
1310                 1315                1320

Ser Gln Pro Arg Trp Pro Ser Trp Gly Trp Asn Gln Val Ser Cys
1325                 1330                1335

Pro Cys Ser Trp Gln Gln Gly Arg Arg Asp Leu Arg Phe Gln Pro
1340                 1345                1350

Val Ser Ile Gly Arg Trp Gly Leu Gly Ser Arg Gln Leu Cys Ser
1355                 1360                1365

Phe Thr Ser Trp Arg Gly Gly Val Cys Cys Ser Tyr Gly Pro Trp
1370                 1375                1380

Gly Glu Phe Arg Glu Gly Trp His Val Gln Arg Pro Trp Gln Leu
1385                 1390                1395

Ala Gln Glu Leu Glu Pro Gln Ser Trp Cys Cys Arg Trp Asn Asp
1400                 1405                1410

Lys Pro Tyr Leu Cys Ala Leu Tyr Gln Gln Arg Arg Pro His Val
1415                 1420                1425

Gly Cys Ala Thr Tyr Arg Pro Pro Gln Pro Ala Trp Met Phe Gly
1430                 1435                1440

Asp Pro His Ile Thr Thr Leu Asp Gly Val Ser Tyr Thr Phe Asn
1445                 1450                1455

Gly Leu Gly Asp Phe Leu Leu Val Gly Ala Gln Asp Gly Asn Ser
1460                 1465                1470

Ser Phe Leu Leu Gln Gly Arg Thr Ala Gln Thr Gly Ser Ala Gln
1475                 1480                1485

Ala Thr Asn Phe Ile Ala Phe Ala Ala Gln Tyr Arg Ser Ser Ser
1490                 1495                1500

```
Leu Gly Pro Val Thr Val Gln Trp Leu Leu Glu Pro His Asp Ala
    1505                1510                1515

Ile Arg Val Leu Leu Asp Asn Gln Thr Val Thr Phe Gln Pro Asp
    1520                1525                1530

His Glu Asp Gly Gly Gly Gln Glu Thr Phe Asn Ala Thr Gly Val
    1535                1540                1545

Leu Leu Ser Arg Asn Gly Ser Glu Val Ser Ala Ser Phe Asp Gly
    1550                1555                1560

Trp Ala Thr Val Ser Val Ile Ala Leu Ser Asn Ile Leu His Ala
    1565                1570                1575

Ser Ala Ser Leu Pro Pro Glu Tyr Gln Asn Arg Thr Glu Gly Leu
    1580                1585                1590

Leu Gly Val Trp Asn Asn Asn Pro Glu Asp Asp Phe Arg Met Pro
    1595                1600                1605

Asn Gly Ser Thr Ile Pro Pro Gly Ser Pro Glu Glu Met Leu Phe
    1610                1615                1620

His Phe Gly Met Thr Trp Gln Ile Asn Gly Thr Gly Leu Leu Gly
    1625                1630                1635

Lys Arg Asn Asp Gln Leu Pro Ser Asn Phe Thr Pro Val Phe Tyr
    1640                1645                1650

Ser Gln Leu Gln Lys Asn Ser Ser Trp Ala Glu His Leu Ile Ser
    1655                1660                1665

Asn Cys Asp Gly Asp Ser Ser Cys Ile Tyr Asp Thr Leu Ala Leu
    1670                1675                1680

Arg Asn Ala Ser Ile Gly Leu His Thr Arg Glu Val Ser Lys Asn
    1685                1690                1695

Tyr Glu Gln Ala Asn Ala Thr Leu Asn Gln Tyr Pro Pro Ser Ile
    1700                1705                1710

Asn Gly Gly Arg Val Ile Glu Ala Tyr Lys Gly Gln Thr Thr Leu
    1715                1720                1725

Ile Gln Tyr Thr Ser Asn Ala Glu Asp Ala Asn Phe Thr Leu Arg
    1730                1735                1740

Asp Ser Cys Thr Asp Leu Glu Leu Phe Glu Asn Gly Thr Leu Leu
    1745                1750                1755

Trp Thr Pro Lys Ser Leu Glu Pro Phe Thr Leu Glu Ile Leu Ala
    1760                1765                1770

Arg Ser Ala Lys Ile Gly Leu Ala Ser Ala Leu Gln Pro Arg Thr
    1775                1780                1785

Val Val Cys His Cys Asn Ala Glu Ser Gln Cys Leu Tyr Asn Gln
    1790                1795                1800

Thr Ser Arg Val Gly Asn Ser Ser Leu Glu Val Ala Gly Cys Lys
    1805                1810                1815

Cys Asp Gly Gly Thr Phe Gly Arg Tyr Cys Glu Gly Ser Glu Asp
    1820                1825                1830

Ala Cys Glu Glu Pro Cys Phe Pro Ser Val His Cys Val Pro Gly
    1835                1840                1845

Lys Gly Cys Glu Ala Cys Pro Pro Asn Leu Thr Gly Asp Gly Arg
    1850                1855                1860

His Cys Ala Ala Leu Gly Ser Ser Phe Leu Cys Gln Asn Gln Ser
    1865                1870                1875

Cys Pro Val Asn Tyr Cys Tyr Asn Gln Gly His Cys Tyr Ile Ser
    1880                1885                1890

Gln Thr Leu Gly Cys Gln Pro Met Cys Thr Cys Pro Pro Ala Phe
```

-continued

```
                     1895                1900                1905

Thr  Asp  Ser  Arg  Cys  Phe  Leu  Ala  Gly  Asn  Asn  Phe  Ser  Pro  Thr
         1910                1915                1920

Val  Asn  Leu  Glu  Leu  Pro  Leu  Arg  Val  Ile  Gln  Leu  Leu  Leu  Ser
         1925                1930                1935

Glu  Glu  Glu  Asn  Ala  Ser  Met  Ala  Glu  Val  Asn  Ala  Ser  Val  Ala
         1940                1945                1950

Tyr  Arg  Leu  Gly  Thr  Leu  Asp  Met  Arg  Ala  Phe  Leu  Arg  Asn  Ser
         1955                1960                1965

Gln  Val  Glu  Arg  Ile  Asp  Ser  Ala  Ala  Pro  Ala  Ser  Gly  Ser  Pro
         1970                1975                1980

Ile  Gln  His  Trp  Met  Val  Ile  Ser  Glu  Phe  Gln  Tyr  Arg  Pro  Arg
         1985                1990                1995

Gly  Pro  Val  Ile  Asp  Phe  Leu  Asn  Asn  Gln  Leu  Leu  Ala  Ala  Val
         2000                2005                2010

Val  Glu  Ala  Phe  Leu  Tyr  His  Val  Pro  Arg  Arg  Ser  Glu  Glu  Pro
         2015                2020                2025

Arg  Asn  Asp  Val  Val  Phe  Gln  Pro  Ile  Ser  Gly  Glu  Asp  Val  Arg
         2030                2035                2040

Asp  Val  Thr  Ala  Leu  Asn  Val  Ser  Thr  Leu  Lys  Ala  Tyr  Phe  Arg
         2045                2050                2055

Cys  Asp  Gly  Tyr  Lys  Gly  Tyr  Asp  Leu  Val  Tyr  Ser  Pro  Gln  Ser
         2060                2065                2070

Gly  Phe  Thr  Cys  Val  Ser  Pro  Cys  Ser  Arg  Gly  Tyr  Cys  Asp  His
         2075                2080                2085

Gly  Gly  Gln  Cys  Gln  His  Leu  Pro  Ser  Gly  Pro  Arg  Cys  Ser  Cys
         2090                2095                2100

Val  Ser  Phe  Ser  Ile  Tyr  Thr  Ala  Trp  Gly  Glu  His  Cys  Glu  His
         2105                2110                2115

Leu  Ser  Met  Lys  Leu  Asp  Ala  Phe  Phe  Gly  Ile  Phe  Phe  Gly  Ala
         2120                2125                2130

Leu  Gly  Gly  Leu  Leu  Leu  Leu  Gly  Val  Gly  Thr  Phe  Val  Val  Leu
         2135                2140                2145

Arg  Phe  Trp  Gly  Cys  Ser  Gly  Ala  Arg  Phe  Ser  Tyr  Phe  Leu  Asn
         2150                2155                2160

Ser  Ala  Glu  Ala  Leu  Pro
         2165

<210> SEQ ID NO 35
<211> LENGTH: 32
<212> TYPE: PRT
<213> ORGANISM: artificial sequence
<220> FEATURE:
<223> OTHER INFORMATION: MUC1 polypeptide sequence

<400> SEQUENCE: 35

Gln  Arg  Asp  Ile  Ser  Glu  Met  Phe  Leu  Gln  Ile  Tyr  Lys  Gln  Gly  Gly
1                    5                   10                  15

Phe  Leu  Gly  Leu  Ser  Asn  Ile  Lys  Phe  Arg  Pro  Gly  Ser  Val  Val  Val
                20                  25                  30

<210> SEQ ID NO 36
<211> LENGTH: 18
<212> TYPE: PRT
<213> ORGANISM: artificial sequence
<220> FEATURE:
<223> OTHER INFORMATION: MUC4 polypeptide sequence
```

```
<400> SEQUENCE: 36

Glu Ser Asp Tyr Gln Ile Phe Ser Tyr Pro Asn Pro Leu Pro Ser Gly
1               5                   10                  15

Phe Thr

<210> SEQ ID NO 37
<211> LENGTH: 180
<212> TYPE: PRT
<213> ORGANISM: Homo sapien

<400> SEQUENCE: 37

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Gly Ala Pro Arg Gly Pro
        50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 38
<211> LENGTH: 30
<212> TYPE: PRT
<213> ORGANISM: artificial sequence
<220> FEATURE:
<223> OTHER INFORMATION: polypeptide of amino acids 82-111 of NY-ESO-1

<400> SEQUENCE: 38

Gly Pro Glu Ser Arg Leu Leu Glu Phe Tyr Leu Ala Met Pro Phe Ala
1               5                   10                  15

Thr Pro Met Glu Ala Glu Leu Ala Arg Arg Ser Leu Ala Gln
                20                  25                  30

<210> SEQ ID NO 39
<211> LENGTH: 142
<212> TYPE: PRT
<213> ORGANISM: Homo sapien

<400> SEQUENCE: 39

Met Gly Ala Pro Thr Leu Pro Pro Ala Trp Gln Pro Phe Leu Lys Asp
1               5                   10                  15
```

```
His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu His Lys His
65                  70                  75                  80

Ser Ser Gly Cys Ala Phe Leu Ser Val Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Glu Phe Glu Glu Thr Ala
        115                 120                 125

Lys Lys Val Arg Arg Ala Ile Glu Gln Leu Ala Ala Met Asp
            130                 135                 140

<210> SEQ ID NO 40
<211> LENGTH: 30
<212> TYPE: PRT
<213> ORGANISM: artificial sequence
<220> FEATURE:
<223> OTHER INFORMATION: survivin sequence with variable Xaa mutant
      amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 40

Ala Phe Leu Ser Val Lys Lys Gln Phe Glu Glu Leu Xaa Leu Gly Glu
1               5                   10                  15

Phe Leu Lys Xaa Asp Arg Glu Arg Ala Lys Asn Lys Ile Ala
            20                  25                  30

<210> SEQ ID NO 41
<211> LENGTH: 30
<212> TYPE: PRT
<213> ORGANISM: artificial sequence
<220> FEATURE:
<223> OTHER INFORMATION: amino-acid modified survivin sequence

<400> SEQUENCE: 41

Ala Phe Leu Ser Val Lys Lys Gln Phe Glu Glu Leu Thr Leu Gly Glu
1               5                   10                  15

Phe Leu Lys Leu Asp Arg Glu Arg Ala Lys Asn Lys Ile Ala
            20                  25                  30

<210> SEQ ID NO 42
<211> LENGTH: 30
<212> TYPE: PRT
<213> ORGANISM: artificial sequence
<220> FEATURE:
<223> OTHER INFORMATION: amino-acid modified survivin sequence

<400> SEQUENCE: 42

Ala Phe Leu Ser Val Lys Lys Gln Phe Glu Glu Leu Thr Leu Gly Glu
1               5                   10                  15

Phe Leu Lys Tyr Asp Arg Glu Arg Ala Lys Asn Lys Ile Ala
```

<210> SEQ ID NO 43
<211> LENGTH: 30
<212> TYPE: PRT
<213> ORGANISM: artificial sequence
<220> FEATURE:
<223> OTHER INFORMATION: amino-acid modified survivin sequence

<400> SEQUENCE: 43

Ala Phe Leu Ser Val Lys Lys Gln Phe Glu Glu Leu Thr Leu Gly Glu
1               5                   10                  15
Phe Leu Lys Ile Asp Arg Glu Arg Ala Lys Asn Lys Ile Ala
            20                  25                  30

<210> SEQ ID NO 44
<211> LENGTH: 30
<212> TYPE: PRT
<213> ORGANISM: artificial sequence
<220> FEATURE:
<223> OTHER INFORMATION: amino-acid modified survivin sequence

<400> SEQUENCE: 44

Ala Phe Leu Ser Val Lys Lys Gln Phe Glu Glu Leu Tyr Leu Gly Glu
1               5                   10                  15
Phe Leu Lys Leu Asp Arg Glu Arg Ala Lys Asn Lys Ile Ala
            20                  25                  30

<210> SEQ ID NO 45
<211> LENGTH: 403
<212> TYPE: PRT
<213> ORGANISM: Homo sapien

<400> SEQUENCE: 45

Met Ala His Ala Met Glu Asn Ser Trp Thr Ile Ser Lys Glu Tyr His
1               5                   10                  15
Ile Asp Glu Glu Val Gly Phe Ala Leu Pro Asn Pro Gln Glu Asn Leu
            20                  25                  30
Pro Asp Phe Tyr Asn Asp Trp Met Phe Ile Ala Lys His Leu Pro Asp
        35                  40                  45
Leu Ile Glu Ser Gly Gln Leu Arg Glu Arg Val Glu Lys Leu Asn Met
    50                  55                  60
Leu Ser Ile Asp His Leu Thr Asp His Lys Ser Gln Arg Leu Ala Arg
65                  70                  75                  80
Leu Val Leu Gly Cys Ile Thr Met Ala Tyr Val Trp Gly Lys Gly His
                85                  90                  95
Gly Asp Val Arg Lys Val Leu Pro Arg Asn Ile Ala Val Pro Tyr Cys
            100                 105                 110
Gln Leu Ser Lys Lys Leu Glu Leu Pro Pro Ile Leu Val Tyr Ala Asp
        115                 120                 125
Cys Val Leu Ala Asn Trp Lys Lys Lys Asp Pro Asn Lys Pro Leu Thr
    130                 135                 140
Tyr Glu Asn Met Asp Val Leu Phe Ser Phe Arg Asp Gly Asp Cys Ser
145                 150                 155                 160
Lys Gly Phe Phe Leu Val Ser Leu Leu Val Glu Ile Ala Ala Ala Ser
                165                 170                 175
Ala Ile Lys Val Ile Pro Thr Val Phe Lys Ala Met Gln Met Gln Glu
            180                 185                 190
Arg Asp Thr Leu Leu Lys Ala Leu Leu Glu Ile Ala Ser Cys Leu Glu

```
                195                 200                 205
Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270

Phe Asp Val Leu Leu Gly Ile Gln Gln Thr Ala Gly Gly His Ala
        275                 280                 285

Ala Gln Phe Leu Gln Asp Met Arg Arg Tyr Met Pro Pro Ala His Arg
    290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
                325                 330                 335

Lys Ala Leu Val Ser Leu Arg Ser Tyr His Leu Gln Ile Val Thr Lys
            340                 345                 350

Tyr Ile Leu Ile Pro Ala Ser Gln Gln Pro Lys Glu Asn Lys Thr Ser
        355                 360                 365

Glu Asp Pro Ser Lys Leu Glu Ala Lys Gly Thr Gly Thr Asp Leu
    370                 375                 380

Met Asn Phe Leu Lys Thr Val Arg Ser Thr Thr Glu Lys Ser Leu Leu
385                 390                 395                 400

Lys Glu Gly

<210> SEQ ID NO 46
<211> LENGTH: 30
<212> TYPE: PRT
<213> ORGANISM: artificial sequence
<220> FEATURE:
<223> OTHER INFORMATION: polypeptide sequence encoding surviving amino
      acids 104-133

<400> SEQUENCE: 46

Pro Arg Asn Ile Ala Val Pro Tyr Cys Gln Leu Ser Lys Lys Leu Glu
1               5                   10                  15

Leu Pro Pro Ile Leu Val Tyr Ala Asp Cys Val Leu Ala Asn
            20                  25                  30

<210> SEQ ID NO 47
<211> LENGTH: 338
<212> TYPE: PRT
<213> ORGANISM: Homo sapien

<400> SEQUENCE: 47

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80
```

-continued

```
Pro Glu Tyr Trp Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
            195                 200                 205

Pro Lys Thr His Val Thr His His Pro Val Phe Asp Tyr Glu Ala Thr
210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Glu Pro Leu Met Leu Arg Trp Lys Gln Ser Ser Leu Pro
290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp
```

<210> SEQ ID NO 48
<211> LENGTH: 15
<212> TYPE: PRT
<213> ORGANISM: artificial sequence
<220> FEATURE:
<223> OTHER INFORMATION: polypeptide encoding amino acids 96-110 of
      modified HLA-G sequence

<400> SEQUENCE: 48

```
Gln Thr Asp Arg Leu Asn Leu Gln Thr Leu Arg Gly Tyr Tyr Asn
1               5                   10                  15
```

<210> SEQ ID NO 49
<211> LENGTH: 435
<212> TYPE: PRT
<213> ORGANISM: Homo sapien

<400> SEQUENCE: 49

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30
```

```
Glu Lys Gly Asp Pro Thr Glu Arg Glu Leu Arg Val Gly Leu Glu Glu
         35                  40                  45

Ser Glu Leu Trp Leu Arg Phe Lys Glu Leu Thr Asn Glu Met Ile Val
 50                  55                  60

Thr Lys Asn Gly Arg Arg Met Phe Pro Val Leu Lys Val Asn Val Ser
 65                  70                  75                  80

Gly Leu Asp Pro Asn Ala Met Tyr Ser Phe Leu Leu Asp Phe Val Ala
                 85                  90                  95

Ala Asp Asn His Arg Trp Lys Tyr Val Asn Gly Glu Trp Val Pro Gly
                100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Gln Tyr Pro Ser Leu Trp Ser
            340                 345                 350

Val Ser Asn Gly Ala Val Thr Pro Gly Ser Gln Ala Ala Val Ser
    355                 360                 365

Asn Gly Leu Gly Ala Gln Phe Phe Arg Gly Ser Pro Ala His Tyr Thr
370                 375                 380

Pro Leu Thr His Pro Val Ser Ala Pro Ser Ser Gly Ser Pro Leu
385                 390                 395                 400

Tyr Glu Gly Ala Ala Ala Ala Thr Asp Ile Val Asp Ser Gln Tyr Asp
                405                 410                 415

Ala Ala Ala Gln Gly Arg Leu Ile Ala Ser Trp Thr Pro Val Ser Pro
            420                 425                 430

Pro Ser Met
        435
```

-continued

```
<210> SEQ ID NO 50
<211> LENGTH: 30
<212> TYPE: PRT
<213> ORGANISM: artificial sequence
<220> FEATURE:
<223> OTHER INFORMATION: polypeptide encoding brachyury amino acids
      151-180

<400> SEQUENCE: 50

Lys Leu Asn Gly Gly Gly Gln Ile Met Leu Asn Ser Leu His Lys Tyr
1               5                   10                  15

Glu Pro Arg Ile His Ile Val Arg Val Gly Gly Pro Gln Arg
            20                  25                  30

<210> SEQ ID NO 51
<211> LENGTH: 25
<212> TYPE: PRT
<213> ORGANISM: artificial sequence
<220> FEATURE:
<223> OTHER INFORMATION: generic sequence with mutant amino acid flanked
      by 12 canonical amino acids on each side.
<220> FEATURE:
<221> NAME/KEY: misc_feature
<222> LOCATION: (1)..(25)
<223> OTHER INFORMATION: Xaa can be any naturally occurring amino acid

<400> SEQUENCE: 51

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 52
<211> LENGTH: 2768
<212> TYPE: PRT
<213> ORGANISM: Homo sapiens

<400> SEQUENCE: 52

Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
            20                  25                  30

Pro Cys Glu Leu Gln Arg Glu Thr Ala Phe Leu Lys Gln Ala Asp Tyr
        35                  40                  45

Val Pro Gln Cys Ala Glu Asp Gly Ser Phe Gln Thr Val Gln Cys Gln
    50                  55                  60

Asn Asp Gly Arg Ser Cys Trp Cys Val Gly Ala Asn Gly Ser Glu Val
65                  70                  75                  80

Leu Gly Ser Arg Gln Pro Gly Arg Pro Val Ala Cys Leu Ser Phe Cys
                85                  90                  95

Gln Leu Gln Lys Gln Gln Ile Leu Leu Ser Gly Tyr Ile Asn Ser Thr
            100                 105                 110

Asp Thr Ser Tyr Leu Pro Gln Cys Gln Asp Ser Gly Asp Tyr Ala Pro
        115                 120                 125

Val Gln Cys Asp Val Gln Gln Val Gln Cys Trp Cys Val Asp Ala Glu
    130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Arg Leu Leu His Gly Val Gly
                165                 170                 175

Asp Lys Ser Pro Pro Gln Cys Ser Ala Glu Gly Glu Phe Met Pro Val
```

```
                180             185             190
Gln Cys Lys Phe Val Asn Thr Thr Asp Met Met Ile Phe Asp Leu Val
            195             200             205
His Ser Tyr Asn Arg Phe Pro Asp Ala Phe Val Thr Phe Ser Ser Phe
            210             215             220
Gln Arg Arg Phe Pro Glu Val Ser Gly Tyr Cys His Cys Ala Asp Ser
225             230             235             240
Gln Gly Arg Glu Leu Ala Glu Thr Gly Leu Glu Leu Leu Asp Glu
            245             250             255
Ile Tyr Asp Thr Ile Phe Ala Gly Leu Asp Leu Pro Ser Thr Phe Thr
            260             265             270
Glu Thr Thr Leu Tyr Arg Ile Leu Gln Arg Arg Phe Leu Ala Val Gln
            275             280             285
Ser Val Ile Ser Gly Arg Phe Arg Cys Pro Thr Lys Cys Glu Val Glu
            290             295             300
Arg Phe Thr Ala Thr Ser Phe Gly His Pro Tyr Val Pro Ser Cys Arg
305             310             315             320
Arg Asn Gly Asp Tyr Gln Ala Val Gln Cys Gln Thr Glu Gly Pro Cys
            325             330             335
Trp Cys Val Asp Ala Gln Gly Lys Glu Met His Gly Thr Arg Gln Gln
            340             345             350
Gly Glu Pro Pro Ser Cys Ala Glu Gly Gln Ser Cys Ala Ser Glu Arg
            355             360             365
Gln Gln Ala Leu Ser Arg Leu Tyr Phe Gly Thr Ser Gly Tyr Phe Ser
            370             375             380
Gln His Asp Leu Phe Ser Ser Pro Glu Lys Arg Trp Ala Ser Pro Arg
385             390             395             400
Val Ala Arg Phe Ala Thr Ser Cys Pro Pro Thr Ile Lys Glu Leu Phe
            405             410             415
Val Asp Ser Gly Leu Leu Arg Pro Met Val Glu Gly Gln Ser Gln Gln
            420             425             430
Phe Ser Val Ser Glu Asn Leu Leu Lys Glu Ala Ile Arg Ala Ile Phe
            435             440             445
Pro Ser Arg Gly Leu Ala Arg Leu Ala Leu Gln Phe Thr Thr Asn Pro
            450             455             460
Lys Arg Leu Gln Gln Asn Leu Phe Gly Gly Lys Phe Leu Val Asn Val
465             470             475             480
Gly Gln Phe Asn Leu Ser Gly Ala Leu Gly Thr Arg Gly Thr Phe Asn
            485             490             495
Phe Ser Gln Phe Phe Gln Gln Leu Gly Leu Ala Ser Phe Leu Asn Gly
            500             505             510
Gly Arg Gln Glu Asp Leu Ala Lys Pro Leu Ser Val Gly Leu Asp Ser
            515             520             525
Asn Ser Ser Thr Gly Thr Pro Glu Ala Ala Lys Lys Asp Gly Thr Met
            530             535             540
Asn Lys Pro Thr Val Gly Ser Phe Gly Phe Glu Ile Asn Leu Gln Glu
545             550             555             560
Asn Gln Asn Ala Leu Lys Phe Leu Ala Ser Leu Leu Glu Leu Pro Glu
            565             570             575
Phe Leu Leu Phe Leu Gln His Ala Ile Ser Val Pro Glu Asp Val Ala
            580             585             590
Arg Asp Leu Gly Asp Val Met Glu Thr Val Leu Ser Ser Gln Thr Cys
            595             600             605
```

-continued

```
Glu Gln Thr Pro Glu Arg Leu Phe Val Pro Ser Cys Thr Glu Gly
    610             615             620
Ser Tyr Glu Asp Val Gln Cys Phe Ser Gly Glu Cys Trp Cys Val Asn
625             630             635             640
Ser Trp Gly Lys Glu Leu Pro Gly Ser Arg Val Arg Gly Gly Gln Pro
                645             650             655
Arg Cys Pro Thr Asp Cys Glu Lys Gln Arg Ala Arg Met Gln Ser Leu
            660             665             670
Met Gly Ser Gln Pro Ala Gly Ser Thr Leu Phe Val Pro Ala Cys Thr
        675             680             685
Ser Glu Gly His Phe Leu Pro Val Gln Cys Phe Asn Ser Glu Cys Tyr
    690             695             700
Cys Val Asp Ala Glu Gly Gln Ala Ile Pro Gly Thr Arg Ser Ala Ile
705             710             715             720
Gly Lys Pro Lys Lys Cys Pro Thr Pro Cys Gln Leu Gln Ser Glu Gln
                725             730             735
Ala Phe Leu Arg Thr Val Gln Ala Leu Leu Ser Asn Ser Ser Met Leu
            740             745             750
Pro Thr Leu Ser Asp Thr Tyr Ile Pro Gln Cys Ser Thr Asp Gly Gln
        755             760             765
Trp Arg Gln Val Gln Cys Asn Gly Pro Pro Glu Gln Val Phe Glu Leu
    770             775             780
Tyr Gln Arg Trp Glu Ala Gln Asn Lys Gly Gln Asp Leu Thr Pro Ala
785             790             795             800
Lys Leu Leu Val Lys Ile Met Ser Tyr Arg Glu Ala Ala Ser Gly Asn
                805             810             815
Phe Ser Leu Phe Ile Gln Ser Leu Tyr Glu Ala Gly Gln Gln Asp Val
            820             825             830
Phe Pro Val Leu Ser Gln Tyr Pro Ser Leu Gln Asp Val Pro Leu Ala
        835             840             845
Ala Leu Glu Gly Lys Arg Pro Gln Pro Arg Glu Asn Ile Leu Leu Glu
    850             855             860
Pro Tyr Leu Phe Trp Gln Ile Leu Asn Gly Gln Leu Ser Gln Tyr Pro
865             870             875             880
Gly Ser Tyr Ser Asp Phe Ser Thr Pro Leu Ala His Phe Asp Leu Arg
                885             890             895
Asn Cys Trp Cys Val Asp Glu Ala Gly Gln Glu Leu Glu Gly Met Arg
            900             905             910
Ser Glu Pro Ser Lys Leu Pro Thr Cys Pro Gly Ser Cys Glu Glu Ala
        915             920             925
Lys Leu Arg Val Leu Gln Phe Ile Arg Glu Thr Glu Glu Ile Val Ser
    930             935             940
Ala Ser Asn Ser Ser Arg Phe Pro Leu Gly Glu Ser Phe Leu Val Ala
945             950             955             960
Lys Gly Ile Arg Leu Arg Asn Glu Asp Leu Gly Leu Pro Pro Leu Phe
                965             970             975
Pro Pro Arg Glu Ala Phe Ala Glu Gln Phe Leu Arg Gly Ser Asp Tyr
            980             985             990
Ala Ile Arg Leu Ala Ala Gln Ser Thr Leu Ser Phe Tyr Gln Arg Arg
        995             1000            1005
Arg Phe Ser Pro Asp Asp Ser Ala Gly Ala Ser Ala Leu Leu Arg
    1010            1015            1020
```

```
Ser Gly Pro Tyr Met Pro Gln Cys Asp Ala Phe Gly Ser Trp Glu
    1025                1030                1035

Pro Val Gln Cys His Ala Gly Thr Gly His Cys Trp Cys Val Asp
    1040                1045                1050

Glu Lys Gly Gly Phe Ile Pro Gly Ser Leu Thr Ala Arg Ser Leu
    1055                1060                1065

Gln Ile Pro Gln Cys Pro Thr Thr Cys Glu Lys Ser Arg Thr Ser
    1070                1075                1080

Gly Leu Leu Ser Ser Trp Lys Gln Ala Arg Ser Gln Glu Asn Pro
    1085                1090                1095

Ser Pro Lys Asp Leu Phe Val Pro Ala Cys Leu Glu Thr Gly Glu
    1100                1105                1110

Tyr Ala Arg Leu Gln Ala Ser Gly Ala Gly Thr Trp Cys Val Asp
    1115                1120                1125

Pro Ala Ser Gly Glu Glu Leu Arg Pro Gly Ser Ser Ser Ser Ala
    1130                1135                1140

Gln Cys Pro Ser Leu Cys Asn Val Leu Lys Ser Gly Val Leu Ser
    1145                1150                1155

Arg Arg Val Ser Pro Gly Tyr Val Pro Ala Cys Arg Ala Glu Asp
    1160                1165                1170

Gly Gly Phe Ser Pro Val Gln Cys Asp Gln Ala Gln Gly Ser Cys
    1175                1180                1185

Trp Cys Val Met Asp Ser Gly Glu Glu Val Pro Gly Thr Arg Val
    1190                1195                1200

Thr Gly Gly Gln Pro Ala Cys Glu Ser Pro Arg Cys Pro Leu Pro
    1205                1210                1215

Phe Asn Ala Ser Glu Val Val Gly Gly Thr Ile Leu Cys Glu Thr
    1220                1225                1230

Ile Ser Gly Pro Thr Gly Ser Ala Met Gln Gln Cys Gln Leu Leu
    1235                1240                1245

Cys Arg Gln Gly Ser Trp Ser Val Phe Pro Pro Gly Pro Leu Ile
    1250                1255                1260

Cys Ser Leu Glu Ser Gly Arg Trp Glu Ser Gln Leu Pro Gln Pro
    1265                1270                1275

Arg Ala Cys Gln Arg Pro Gln Leu Trp Gln Thr Ile Gln Thr Gln
    1280                1285                1290

Gly His Phe Gln Leu Gln Leu Pro Pro Gly Lys Met Cys Ser Ala
    1295                1300                1305

Asp Tyr Ala Asp Leu Leu Gln Thr Phe Gln Val Phe Ile Leu Asp
    1310                1315                1320

Glu Leu Thr Ala Arg Gly Phe Cys Gln Ile Gln Val Lys Thr Phe
    1325                1330                1335

Gly Thr Leu Val Ser Ile Pro Val Cys Asn Asn Ser Ser Val Gln
    1340                1345                1350

Val Gly Cys Leu Thr Arg Glu Arg Leu Gly Val Asn Val Thr Trp
    1355                1360                1365

Lys Ser Arg Leu Glu Asp Ile Pro Val Ala Ser Leu Pro Asp Leu
    1370                1375                1380

His Asp Ile Glu Arg Ala Leu Val Gly Lys Asp Leu Leu Gly Arg
    1385                1390                1395

Phe Thr Asp Leu Ile Gln Ser Gly Ser Phe Gln Leu His Leu Asp
    1400                1405                1410

Ser Lys Thr Phe Pro Ala Glu Thr Ile Arg Phe Leu Gln Gly Asp
```

-continued

```
            1415                1420                1425

His Phe Gly Thr Ser Pro Arg Thr Trp Phe Gly Cys Ser Glu Gly
            1430                1435                1440

Phe Tyr Gln Val Leu Thr Ser Glu Ala Ser Gln Asp Gly Leu Gly
            1445                1450                1455

Cys Val Lys Cys Pro Glu Gly Ser Tyr Ser Gln Asp Glu Glu Cys
            1460                1465                1470

Ile Pro Cys Pro Val Gly Phe Tyr Gln Glu Gln Ala Gly Ser Leu
            1475                1480                1485

Ala Cys Val Pro Cys Pro Val Gly Arg Thr Thr Ile Ser Ala Gly
            1490                1495                1500

Ala Phe Ser Gln Thr His Cys Val Thr Asp Cys Gln Arg Asn Glu
            1505                1510                1515

Ala Gly Leu Gln Cys Asp Gln Asn Gly Gln Tyr Arg Ala Ser Gln
            1520                1525                1530

Lys Asp Arg Gly Ser Gly Lys Ala Phe Cys Val Asp Gly Glu Gly
            1535                1540                1545

Arg Arg Leu Pro Trp Trp Glu Thr Glu Ala Pro Leu Glu Asp Ser
            1550                1555                1560

Gln Cys Leu Met Met Gln Lys Phe Glu Lys Val Pro Glu Ser Lys
            1565                1570                1575

Val Ile Phe Asp Ala Asn Ala Pro Val Ala Val Arg Ser Lys Val
            1580                1585                1590

Pro Asp Ser Glu Phe Pro Val Met Gln Cys Leu Thr Asp Cys Thr
            1595                1600                1605

Glu Asp Glu Ala Cys Ser Phe Phe Thr Val Ser Thr Thr Glu Pro
            1610                1615                1620

Glu Ile Ser Cys Asp Phe Tyr Ala Trp Thr Ser Asp Asn Val Ala
            1625                1630                1635

Cys Met Thr Ser Asp Gln Lys Arg Asp Ala Leu Gly Asn Ser Lys
            1640                1645                1650

Ala Thr Ser Phe Gly Ser Leu Arg Cys Gln Val Lys Val Arg Ser
            1655                1660                1665

His Gly Gln Asp Ser Pro Ala Val Tyr Leu Lys Lys Gly Gln Gly
            1670                1675                1680

Ser Thr Thr Thr Leu Gln Lys Arg Phe Glu Pro Thr Gly Phe Gln
            1685                1690                1695

Asn Met Leu Ser Gly Leu Tyr Asn Pro Ile Val Phe Ser Ala Ser
            1700                1705                1710

Gly Ala Asn Leu Thr Asp Ala His Leu Phe Cys Leu Leu Ala Cys
            1715                1720                1725

Asp Arg Asp Leu Cys Cys Asp Gly Phe Val Leu Thr Gln Val Gln
            1730                1735                1740

Gly Gly Ala Ile Ile Cys Gly Leu Leu Ser Ser Pro Ser Val Leu
            1745                1750                1755

Leu Cys Asn Val Lys Asp Trp Met Asp Pro Ser Glu Ala Trp Ala
            1760                1765                1770

Asn Ala Thr Cys Pro Gly Val Thr Tyr Asp Gln Glu Ser His Gln
            1775                1780                1785

Val Ile Leu Arg Leu Gly Asp Gln Glu Phe Ile Lys Ser Leu Thr
            1790                1795                1800

Pro Leu Glu Gly Thr Gln Asp Thr Phe Thr Asn Phe Gln Gln Val
            1805                1810                1815
```

-continued

Tyr Leu Trp Lys Asp Ser Asp Met Gly Ser Arg Pro Glu Ser Met
1820            1825                1830

Gly Cys Arg Lys Asp Thr Val Pro Arg Pro Ala Ser Pro Thr Glu
1835            1840                1845

Ala Gly Leu Thr Thr Glu Leu Phe Ser Pro Val Asp Leu Asn Gln
1850            1855                1860

Val Ile Val Asn Gly Asn Gln Ser Leu Ser Ser Gln Lys His Trp
1865            1870                1875

Leu Phe Lys His Leu Phe Ser Ala Gln Gln Ala Asn Leu Trp Cys
1880            1885                1890

Leu Ser Arg Cys Val Gln Glu His Ser Phe Cys Gln Leu Ala Glu
1895            1900                1905

Ile Thr Glu Ser Ala Ser Leu Tyr Phe Thr Cys Thr Leu Tyr Pro
1910            1915                1920

Glu Ala Gln Val Cys Asp Asp Ile Met Glu Ser Asn Ala Gln Gly
1925            1930                1935

Cys Arg Leu Ile Leu Pro Gln Met Pro Lys Ala Leu Phe Arg Lys
1940            1945                1950

Lys Val Ile Leu Glu Asp Lys Val Lys Asn Phe Tyr Thr Arg Leu
1955            1960                1965

Pro Phe Gln Lys Leu Met Gly Ile Ser Ile Arg Asn Lys Val Pro
1970            1975                1980

Met Ser Glu Lys Ser Ile Ser Asn Gly Phe Phe Glu Cys Glu Arg
1985            1990                1995

Arg Cys Asp Ala Asp Pro Cys Cys Thr Gly Phe Gly Phe Leu Asn
2000            2005                2010

Val Ser Gln Leu Lys Gly Gly Glu Val Thr Cys Leu Thr Leu Asn
2015            2020                2025

Ser Leu Gly Ile Gln Met Cys Ser Glu Glu Asn Gly Gly Ala Trp
2030            2035                2040

Arg Ile Leu Asp Cys Gly Ser Pro Asp Ile Glu Val His Thr Tyr
2045            2050                2055

Pro Phe Gly Trp Tyr Gln Lys Pro Ile Ala Gln Asn Asn Ala Pro
2060            2065                2070

Ser Phe Cys Pro Leu Val Val Leu Pro Ser Leu Thr Glu Lys Val
2075            2080                2085

Ser Leu Asp Ser Trp Gln Ser Leu Ala Leu Ser Ser Val Val Val
2090            2095                2100

Asp Pro Ser Ile Arg His Phe Asp Val Ala His Val Ser Thr Ala
2105            2110                2115

Ala Thr Ser Asn Phe Ser Ala Val Arg Asp Leu Cys Leu Ser Glu
2120            2125                2130

Cys Ser Gln His Glu Ala Cys Leu Ile Thr Thr Leu Gln Thr Gln
2135            2140                2145

Pro Gly Ala Val Arg Cys Met Phe Tyr Ala Asp Thr Gln Ser Cys
2150            2155                2160

Thr His Ser Leu Gln Gly Gln Asn Cys Arg Leu Leu Leu Arg Glu
2165            2170                2175

Glu Ala Thr His Ile Tyr Arg Lys Pro Gly Ile Ser Leu Leu Ser
2180            2185                2190

Tyr Glu Ala Ser Val Pro Ser Val Pro Ile Ser Thr His Gly Arg
2195            2200                2205

```
Leu Leu Gly Arg Ser Gln Ala Ile Gln Val Gly Thr Ser Trp Lys
2210                2215                2220

Gln Val Asp Gln Phe Leu Gly Val Pro Tyr Ala Ala Pro Pro Leu
2225                2230                2235

Ala Glu Arg Arg Phe Gln Ala Pro Glu Pro Leu Asn Trp Thr Gly
2240                2245                2250

Ser Trp Asp Ala Ser Lys Pro Arg Ala Ser Cys Trp Gln Pro Gly
2255                2260                2265

Thr Arg Thr Ser Thr Ser Pro Gly Val Ser Glu Asp Cys Leu Tyr
2270                2275                2280

Leu Asn Val Phe Ile Pro Gln Asn Val Ala Pro Asn Ala Ser Val
2285                2290                2295

Leu Val Phe Phe His Asn Thr Met Asp Arg Glu Glu Ser Glu Gly
2300                2305                2310

Trp Pro Ala Ile Asp Gly Ser Phe Leu Ala Ala Val Gly Asn Leu
2315                2320                2325

Ile Val Val Thr Ala Ser Tyr Arg Val Gly Val Phe Gly Phe Leu
2330                2335                2340

Ser Ser Gly Ser Gly Glu Val Ser Gly Asn Trp Gly Leu Leu Asp
2345                2350                2355

Gln Val Ala Ala Leu Thr Trp Val Gln Thr His Ile Arg Gly Phe
2360                2365                2370

Gly Gly Asp Pro Arg Arg Val Ser Leu Ala Ala Asp Arg Gly Gly
2375                2380                2385

Ala Asp Val Ala Ser Ile His Leu Leu Thr Ala Arg Ala Thr Asn
2390                2395                2400

Ser Gln Leu Phe Arg Arg Ala Val Leu Met Gly Gly Ser Ala Leu
2405                2410                2415

Ser Pro Ala Ala Val Ile Ser His Glu Arg Ala Gln Gln Gln Ala
2420                2425                2430

Ile Ala Leu Ala Lys Glu Val Ser Cys Pro Met Ser Ser Ser Gln
2435                2440                2445

Glu Val Val Ser Cys Leu Arg Gln Lys Pro Ala Asn Val Leu Asn
2450                2455                2460

Asp Ala Gln Thr Lys Leu Leu Ala Val Ser Gly Pro Phe His Tyr
2465                2470                2475

Trp Gly Pro Val Ile Asp Gly His Phe Leu Arg Glu Pro Pro Ala
2480                2485                2490

Arg Ala Leu Lys Arg Ser Leu Trp Val Glu Val Asp Leu Leu Ile
2495                2500                2505

Gly Ser Ser Gln Asp Asp Gly Leu Ile Asn Arg Ala Lys Ala Val
2510                2515                2520

Lys Gln Phe Glu Glu Ser Arg Gly Arg Thr Ser Ser Lys Thr Ala
2525                2530                2535

Phe Tyr Gln Ala Leu Gln Asn Ser Leu Gly Gly Glu Asp Ser Asp
2540                2545                2550

Ala Arg Val Glu Ala Ala Thr Trp Tyr Tyr Ser Leu Glu His
2555                2560                2565

Ser Thr Asp Asp Tyr Ala Ser Phe Ser Arg Ala Leu Glu Asn Ala
2570                2575                2580

Thr Arg Asp Tyr Phe Ile Ile Cys Pro Ile Ile Asp Met Ala Ser
2585                2590                2595

Ala Trp Ala Lys Arg Ala Arg Gly Asn Val Phe Met Tyr His Ala
```

-continued

```
            2600                2605                2610

Pro Glu Asn Tyr Gly His Gly Ser Leu Glu Leu Leu Ala Asp Val
        2615                2620                2625

Gln Phe Ala Leu Gly Leu Pro Phe Tyr Pro Ala Tyr Glu Gly Gln
        2630                2635                2640

Phe Ser Leu Glu Glu Lys Ser Leu Ser Leu Lys Ile Met Gln Tyr
        2645                2650                2655

Phe Ser His Phe Ile Arg Ser Gly Asn Pro Asn Tyr Pro Tyr Glu
        2660                2665                2670

Phe Ser Arg Lys Val Pro Thr Phe Ala Thr Pro Trp Pro Asp Phe
        2675                2680                2685

Val Pro Arg Ala Gly Gly Glu Asn Tyr Lys Glu Phe Ser Glu Leu
        2690                2695                2700

Leu Pro Asn Arg Gln Gly Leu Lys Lys Ala Asp Cys Ser Phe Trp
        2705                2710                2715

Ser Lys Tyr Ile Ser Ser Leu Lys Thr Ser Ala Asp Gly Ala Lys
        2720                2725                2730

Gly Gly Gln Ser Ala Glu Ser Glu Glu Glu Leu Thr Ala Gly
        2735                2740                2745

Ser Gly Leu Arg Glu Asp Leu Leu Ser Leu Gln Glu Pro Gly Ser
        2750                2755                2760

Lys Thr Tyr Ser Lys
        2765
```

<210> SEQ ID NO 53
<211> LENGTH: 29
<212> TYPE: PRT
<213> ORGANISM: artificial sequence
<220> FEATURE:
<223> OTHER INFORMATION: polypeptide encoding amino acids 249-277 of
      thyroglobulin

<400> SEQUENCE: 53

```
Gly Leu Glu Leu Leu Asp Glu Ile Tyr Asp Thr Ile Phe Ala Gly
1               5                  10                  15

Leu Asp Leu Pro Ser Thr Phe Thr Glu Thr Thr Leu Tyr
            20                  25
```

<210> SEQ ID NO 54
<211> LENGTH: 32
<212> TYPE: PRT
<213> ORGANISM: artificial sequence
<220> FEATURE:
<223> OTHER INFORMATION: polypeptide encoding amino acids 1940-1971 of
      thyroglobulin

<400> SEQUENCE: 54

```
Arg Leu Ile Leu Pro Gln Met Pro Lys Ala Leu Phe Arg Lys Lys Val
1               5                  10                  15

Ile Leu Glu Asp Lys Val Lys Asn Phe Tyr Thr Arg Leu Pro Phe Gln
            20                  25                  30
```

<210> SEQ ID NO 55
<211> LENGTH: 19
<212> TYPE: PRT
<213> ORGANISM: artificial sequence
<220> FEATURE:
<223> OTHER INFORMATION: polypeptide encoding amino acids 2750-2768 of
      thyroglobulin

<400> SEQUENCE: 55

-continued

```
Gly Leu Arg Glu Asp Leu Leu Ser Leu Gln Glu Pro Gly Ser Lys Thr
1               5                   10                  15

Tyr Ser Lys

<210> SEQ ID NO 56
<211> LENGTH: 32
<212> TYPE: PRT
<213> ORGANISM: artificial sequence
<220> FEATURE:
<223> OTHER INFORMATION: polypeptide encoding amino acids 2174-2205 of
      thyroglobulin

<400> SEQUENCE: 56

Leu Leu Leu Arg Glu Glu Ala Thr His Ile Tyr Arg Lys Pro Gly Ile
1               5                   10                  15

Ser Leu Leu Ser Tyr Glu Ala Ser Val Pro Ser Val Pro Ile Ser Thr
                20                  25                  30

<210> SEQ ID NO 57
<211> LENGTH: 933
<212> TYPE: PRT
<213> ORGANISM: Homo sapien

<400> SEQUENCE: 57

Met Arg Ala Leu Ala Val Leu Ser Val Thr Leu Val Met Ala Cys Thr
1               5                   10                  15

Glu Ala Phe Phe Pro Phe Ile Ser Arg Gly Lys Glu Leu Leu Trp Gly
                20                  25                  30

Lys Pro Glu Glu Ser Arg Val Ser Val Leu Glu Ser Lys Arg
                35                  40                  45

Leu Val Asp Thr Ala Met Tyr Ala Thr Met Gln Arg Asn Leu Lys Lys
    50                  55                  60

Arg Gly Ile Leu Ser Pro Ala Gln Leu Leu Ser Phe Ser Lys Leu Pro
65                  70                  75                  80

Glu Pro Thr Ser Gly Val Ile Ala Arg Ala Ala Glu Ile Met Glu Thr
                85                  90                  95

Ser Ile Gln Ala Met Lys Arg Lys Val Asn Leu Lys Thr Gln Gln Ser
                100                 105                 110

Gln His Pro Thr Asp Ala Leu Ser Glu Asp Leu Leu Ser Ile Ile Ala
            115                 120                 125

Asn Met Ser Gly Cys Leu Pro Tyr Met Leu Pro Pro Lys Cys Pro Asn
    130                 135                 140

Thr Cys Leu Ala Asn Lys Tyr Arg Pro Ile Thr Gly Ala Cys Asn Asn
145                 150                 155                 160

Arg Asp His Pro Arg Trp Gly Ala Ser Asn Thr Ala Leu Ala Arg Trp
                165                 170                 175

Leu Pro Pro Val Tyr Glu Asp Gly Phe Ser Gln Pro Arg Gly Trp Asn
                180                 185                 190

Pro Gly Phe Leu Tyr Asn Gly Phe Pro Leu Pro Pro Val Arg Glu Val
            195                 200                 205

Thr Arg His Val Ile Gln Val Ser Asn Glu Val Val Thr Asp Asp Asp
        210                 215                 220

Arg Tyr Ser Asp Leu Leu Met Ala Trp Gly Gln Tyr Ile Asp His Asp
225                 230                 235                 240

Ile Ala Phe Thr Pro Gln Ser Thr Ser Lys Ala Ala Phe Gly Gly Gly
                245                 250                 255
```

```
Ala Asp Cys Gln Met Thr Cys Glu Asn Gln Asn Pro Cys Phe Pro Ile
            260                 265                 270

Gln Leu Pro Glu Glu Ala Arg Pro Ala Ala Gly Thr Ala Cys Leu Pro
        275                 280                 285

Phe Tyr Arg Ser Ser Ala Ala Cys Gly Thr Gly Asp Gln Gly Ala Leu
    290                 295                 300

Phe Gly Asn Leu Ser Thr Ala Asn Pro Arg Gln Gln Met Asn Gly Leu
305                 310                 315                 320

Thr Ser Phe Leu Asp Ala Ser Thr Val Tyr Gly Ser Ser Pro Ala Leu
                325                 330                 335

Glu Arg Gln Leu Arg Asn Trp Thr Ser Ala Glu Gly Leu Leu Arg Val
            340                 345                 350

His Ala Arg Leu Arg Asp Ser Gly Arg Ala Tyr Leu Pro Phe Val Pro
        355                 360                 365

Pro Arg Ala Pro Ala Ala Cys Ala Pro Glu Pro Gly Ile Pro Gly Glu
    370                 375                 380

Thr Arg Gly Pro Cys Phe Leu Ala Gly Asp Gly Arg Ala Ser Glu Val
385                 390                 395                 400

Pro Ser Leu Thr Ala Leu His Thr Leu Trp Leu Arg Glu His Asn Arg
                405                 410                 415

Leu Ala Ala Ala Leu Lys Ala Leu Asn Ala His Trp Ser Ala Asp Ala
            420                 425                 430

Val Tyr Gln Glu Ala Arg Lys Val Val Gly Ala Leu His Gln Ile Ile
        435                 440                 445

Thr Leu Arg Asp Tyr Ile Pro Arg Ile Leu Gly Pro Glu Ala Phe Gln
    450                 455                 460

Gln Tyr Val Gly Pro Tyr Glu Gly Tyr Asp Ser Thr Ala Asn Pro Thr
465                 470                 475                 480

Val Ser Asn Val Phe Ser Thr Ala Ala Phe Arg Phe Gly His Ala Thr
                485                 490                 495

Ile His Pro Leu Val Arg Arg Leu Asp Ala Ser Phe Gln Glu His Pro
            500                 505                 510

Asp Leu Pro Gly Leu Trp Leu His Gln Ala Phe Phe Ser Pro Trp Thr
        515                 520                 525

Leu Leu Arg Gly Gly Gly Leu Asp Pro Leu Ile Arg Gly Leu Leu Ala
    530                 535                 540

Arg Pro Ala Lys Leu Gln Val Gln Asp Gln Leu Met Asn Glu Glu Leu
545                 550                 555                 560

Thr Glu Arg Leu Phe Val Leu Ser Asn Ser Ser Thr Leu Asp Leu Ala
                565                 570                 575

Ser Ile Asn Leu Gln Arg Gly Arg Asp His Gly Leu Pro Gly Tyr Asn
            580                 585                 590

Glu Trp Arg Glu Phe Cys Gly Leu Pro Arg Leu Glu Thr Pro Ala Asp
        595                 600                 605

Leu Ser Thr Ala Ile Ala Ser Arg Ser Val Ala Asp Lys Ile Leu Asp
    610                 615                 620

Leu Tyr Lys His Pro Asp Asn Ile Asp Val Trp Leu Gly Gly Leu Ala
625                 630                 635                 640

Glu Asn Phe Leu Pro Arg Ala Arg Thr Gly Pro Leu Phe Ala Cys Leu
                645                 650                 655

Ile Gly Lys Gln Met Lys Ala Leu Arg Asp Gly Asp Trp Phe Trp Trp
            660                 665                 670

Glu Asn Ser His Val Phe Thr Asp Ala Gln Arg Arg Glu Leu Glu Lys
```

```
                    675                 680                 685
His Ser Leu Ser Arg Val Ile Cys Asp Asn Thr Gly Leu Thr Arg Val
    690                 695                 700
Pro Met Asp Ala Phe Gln Val Gly Lys Phe Pro Glu Asp Phe Glu Ser
705                 710                 715                 720
Cys Asp Ser Ile Thr Gly Met Asn Leu Glu Ala Trp Arg Glu Thr Phe
                    725                 730                 735
Pro Gln Asp Asp Lys Cys Gly Phe Pro Glu Ser Val Glu Asn Gly Asp
                740                 745                 750
Phe Val His Cys Glu Glu Ser Gly Arg Arg Val Leu Val Tyr Ser Cys
            755                 760                 765
Arg His Gly Tyr Glu Leu Gln Gly Arg Glu Gln Leu Thr Cys Thr Gln
        770                 775                 780
Glu Gly Trp Asp Phe Gln Pro Pro Leu Cys Lys Asp Val Asn Glu Cys
785                 790                 795                 800
Ala Asp Gly Ala His Pro Pro Cys His Ala Ser Ala Arg Cys Arg Asn
                    805                 810                 815
Thr Lys Gly Gly Phe Gln Cys Leu Cys Ala Asp Pro Tyr Glu Leu Gly
                820                 825                 830
Asp Asp Gly Arg Thr Cys Val Asp Ser Gly Arg Leu Pro Arg Val Thr
            835                 840                 845
Trp Ile Ser Met Ser Leu Ala Ala Leu Leu Ile Gly Gly Phe Ala Gly
        850                 855                 860
Leu Thr Ser Thr Val Ile Cys Arg Trp Thr Arg Thr Gly Thr Lys Ser
865                 870                 875                 880
Thr Leu Pro Ile Ser Glu Thr Gly Gly Thr Pro Glu Leu Arg Cys
                    885                 890                 895
Gly Lys His Gln Ala Val Gly Thr Ser Pro Gln Arg Ala Ala Ala Gln
                900                 905                 910
Asp Ser Glu Gln Glu Ser Ala Gly Met Glu Gly Arg Asp Thr His Arg
            915                 920                 925
Leu Pro Arg Ala Leu
    930

<210> SEQ ID NO 58
<211> LENGTH: 30
<212> TYPE: PRT
<213> ORGANISM: artificial sequence
<220> FEATURE:
<223> OTHER INFORMATION: polypeptide encoding amino acids 618-647 of TPO

<400> SEQUENCE: 58

Val Ala Asp Lys Ile Leu Asp Leu Tyr Lys His Pro Asp Asn Ile Asp
1               5                   10                  15

Val Trp Leu Gly Gly Leu Ala Glu Asn Phe Leu Pro Arg Ala
            20                  25                  30

<210> SEQ ID NO 59
<211> LENGTH: 30
<212> TYPE: PRT
<213> ORGANISM: artificial sequence
<220> FEATURE:
<223> OTHER INFORMATION: polypeptide encoding amino acids 857-886 of TPO

<400> SEQUENCE: 59

Leu Leu Ile Gly Gly Phe Ala Gly Leu Thr Ser Thr Val Ile Cys Arg
1               5                   10                  15
```

-continued

```
Trp Thr Arg Thr Gly Thr Lys Ser Thr Leu Pro Ile Ser Glu
            20                  25              30

<210> SEQ ID NO 60
<211> LENGTH: 30
<212> TYPE: PRT
<213> ORGANISM: artificial sequence
<220> FEATURE:
<223> OTHER INFORMATION: polypeptide encoding amino acids 355-384 of TPO

<400> SEQUENCE: 60

Arg Leu Arg Asp Ser Gly Arg Ala Tyr Leu Pro Phe Val Pro Pro Arg
1               5                   10                  15

Ala Pro Ala Ala Cys Ala Pro Glu Pro Gly Ile Pro Gly Glu
            20                  25              30

<210> SEQ ID NO 61
<211> LENGTH: 30
<212> TYPE: PRT
<213> ORGANISM: artificial sequence
<220> FEATURE:
<223> OTHER INFORMATION: polypeptide encoding amino acids 235-264 of TPO

<400> SEQUENCE: 61

Gln Tyr Ile Asp His Asp Ile Ala Phe Thr Pro Gln Ser Thr Ser Lys
1               5                   10                  15

Ala Ala Phe Gly Gly Gly Ala Asp Cys Gln Met Thr Cys Glu
            20                  25              30
```

IMMUNOGENIC POLYPEPTIDE COCKTAIL FOR THE TREATMENT OF MEDULLARY THYROID CARCINOMA

CROSS REFERENCE TO RELATED APPLICATION

This application claims the priority benefit of the earlier filing date of U.S. Provisional Application No. 62/299,941, filed Feb. 25, 2016, which is hereby incorporated herein by reference in its entirety.

TECHNICAL FIELD

Embodiments herein relate to treatments for cancer, and more specifically to a multivalent polypeptide/oligonucleotide cocktail for eliciting an immune response to medullary thyroid carcinoma and other solid tumors.

BACKGROUND

Medullary Thyroid Carcinoma (MTC) is a rare malignancy originating from the calcitonin-secreting C cells of the thyroid. Unlike its much more common counterpart, papillary thyroid carcinoma, there is currently no known cure for metastatic MTC, which is not radioiodine avid. Common sites of metastases include the lungs, liver and bones. Among other factors, prognosis depends on disease stage and tumor growth rate, as monitored by the doubling times of serum tumor markers calcitonin and carcinoembryonic antigen (CEA). For patients with distant metastases, the 10 year survival rate is estimated to be 20-40%.

There is no effective adjuvant therapy for early stage MTC, which is commonly resistant to traditional cytotoxic chemotherapy regimens due to slow cytokinetic growth and intrinsic molecular factors, which inhibit apoptosis. Currently available systemic therapies for MTC produce only partial and transient responses, and are limited to use in patients with advanced or rapidly progressing disease. There are currently two FDA-approved targeted molecular therapies for MTC, the multi-kinase inhibitors vandetanib and cabozantinib. In Phase III clinical trials, both drugs improved progression-free survival, but failed to significantly extend overall survival. In fact, for patients lacking RET mutations, cabozantinib reduced median survival by several months. In the hundreds of patients treated in both trials, there were no documented complete responses and investigators deemed several fatalities to be treatment related. The vast majority of patients experienced grade 3 or grade 4 adverse events, including diarrhea, hypertension, desquamation, fatigue and fistulas. Due to harsh side effects, clinical use of both drugs is generally limited to patients with advanced and symptomatic disease. As current treatment regimens are inadequate and impact quality of life, there is a significant unmet clinical need for novel therapies to treat metastatic MTC.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1:
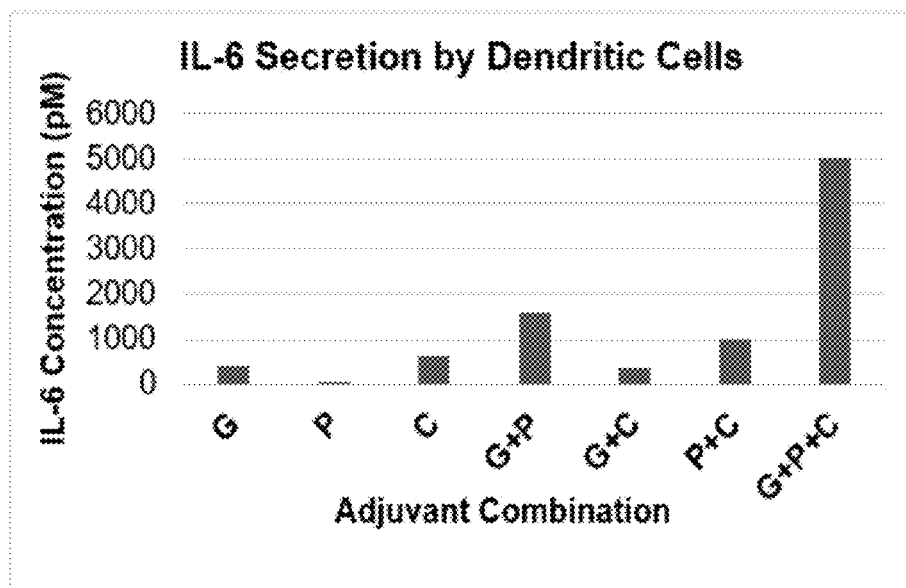
FIG. 1 is a bar graph showing the concentration of interleukin-6 (IL-6) secreted by dendritic cells after 48 hour exposure to various TLR agonists.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

I. Introduction

A strategy for improving treatment of MTC, and other cancers, is to provoke a robust and targeted immune response against cancer cells, for example by administration of an immunogenic composition that elicits an immune response against the cancer cells. The aim of the administration is to reprogram the host's immune system to eradicate cells expressing specific antigen fragments associated with cancer gene expression. Such antigens may include either tissue restricted antigens, i.e. antigens which are exclusively expressed or overexpressed in a given tissue or tumor mutation specific antigens.

Disclosed herein is a novel therapeutic immunogenic composition (which can be referred to herein as MeddieVax) for the treatment of MTC and other human tumors, which may express some or all of the antigens targeted by the immunogenic composition. Also disclosed are methods of treatment using this immunogenic composition as well as methods of making the immunogenic composition.

As disclosed herein, an immunogenic composition includes a novel cocktail of immunogenic polypeptides and adjuvants. This immunogenic composition has been designed to promote a robust immune response against proteins expressed in cancer cells. In addition, the immunogenic composition was designed to address several of the known mechanisms of immune escape, and thereby overcome the deficiencies of previously trialed cancer vaccines.

A. Cancer Biology and Mechanisms of Immune Escape

It has been recognized that tumors can progress due to the failure of the host's immune system to eradicate genetically altered cells which express gene products with mutated polypeptide sequences. These consequential genes, often referred to as oncogenes and tumor suppressor genes, are involved in numerous cellular functions, including DNA damage repair, cell-cycle regulation, proliferation, motility and survival.

The human immune system has sophisticated cellular machinery which can eliminate cells expressing mutated, "non-self" proteins or alternately cells expressing "self" proteins, in a classical autoimmune paradigm. Under normal conditions, nucleated cells routinely present intracellular polypeptide antigen fragments on their membranes which are bound to MHC class I (major histocompatibility complex class I) molecules. This process allows a continuous sampling of the intracellular protein content by patrolling cytotoxic T cells.

MHC class I-restricted epitopes are polypeptide chains comprised of approximately 9 amino acids, which bind with sufficient avidity to MHC class I. Thus, MHC class I molecules, in general, are capable of presenting $20^9=512$ billion possible epitopes. However, only a fraction of these possible epitopes become bona fide epitopes due to HLA restriction. The chemical stability of the MHC I/peptide interaction, as measured by binding affinity, is highly variable, depending on the exact peptide sequence and the host's particular human leukocyte antigen (HLA) alleles. Assuming that a peptide epitope binds with sufficient affinity to a cell's MHC I molecule, it can be transported to the cell surface and presented to patrolling cytotoxic T cells. When a MHC I-bound epitope is presented to a cytotoxic (CD8) T cell, an epitope/MHC/T cell receptor (TCR) complex may be formed. If the epitope/MHC complex binds with sufficient affinity to the TCRs of the activated (non-naïve) T cell, the T cell may be triggered to eradicate the epitope-presenting cell. Under certain conditions, the epitope-presenting cell may be a cancer cell presenting cancer-associated epitopes, and the T cell may be activated cytotoxic T cell. It has been estimated that in a given second, 150 different epitopes are loaded onto a cell's MHC class I molecules. This process enables a vast amount of cellular protein proofreading to occur throughout the course of a single day.

Of note, cytotoxic T cells must first be activated, in order to destroy cells expressing their cognate antigen(s). Prior to activation, T cells are considered naïve, and unable to execute cytolytic functions. Anti-tumoral T cell activation is thought to occur during a process known as cross-priming, whereby dendritic cells or other profession antigen presenting cells (APCs) simultaneously uptake complexed tumor antigens and activating signaling molecules, generically known as PAMPs (pathogen activating molecular patterns) or DAMPs (damage activating molecular patterns). One important class of PAMPs are toll-like receptor (TLR) agonists, including those which activate TLR-2, TLR-7, TLR-8 and TLR-9. The function of the adjuvant is provide such activating signaling molecules to the dendritic cells, in order to promote T cell activation.

The human body is constantly exposed to environmental mutagens from naturally occurring compounds, synthetic chemicals and ionizing radiation from nuclear isotopes and cosmic rays. Furthermore, the process of DNA replication is imperfect. It takes only a few mutations in a single cell to initiate tumor formation. The average human has 37.2 trillion cells and the nucleus of each somatic cell holds an estimated 3.2 billion base pairs. Indeed, a typical human harbors $2.34 \times 10^{23}$ DNA base pairs. Of this mathematically profound genomic library, as few as two point mutations in the entire genome can initiate tumorigenesis. In light of known mutation rates, it is conceivable that the redundancy inherent to the human immune system alongside cellular apoptosis mechanisms prevents a very large number of cancers from forming by eradicating corrupted cells early in the process of tumorigenesis.

On occasion, mutated cells are able to evade immune surveillance and begin the process of tumorigenesis. Via the combined processes of immunoediting and clonal evolution, cancer cells may evade immune eradication by employing several escape mechanisms. A list of six potential escape mechanisms is enumerated as follows.

1. The cancer cells may express weakly immunogenic antigens by virtue of having mutations in epitope regions exhibiting weak MHC I binding affinity as dictated by the host's unique HLA complex. Due to weak MHC binding affinity, mutations in these "immunogenic blind spots" are allowed to persevere without immune clearance, as they are not efficiently presented to cytotoxic T cells by MHC I molecules.

2. The cancer cells may fail to present potential epitopes to cytotoxic T cells via complete or partial loss of MHC I expression, which among other factors, can result from mutations or deletions in genes required for MHC I expression, such as β-2 microglobulin.

3. Initially responsive cytotoxic T cells may become anergic due to interactions with regulatory T cells. Dendritic cells are known to activate clonal expansion of regulatory T cells when potential epitopes are presented in the absence of other immune-stimulating PAMPs and/or DAMPs.

4. Tumor cells are proteomically heterogeneous. T cell clones capable of killing tumor cells expressing a particular epitope will leave behind a contingent of tumor cells which fail to express the targeted epitope.

5. The tumor environment is immunosuppressive, as cancer cells often express inhibitory molecules such as PD-L1, synthesize enzymes such as Indoleamine 2,3-dioxygenase (IDO) or cytokines such as TGF-β and IL-10 which are all known to suppress effector T cells.

6. Cancer cells may upregulate tolerogenic proteins, such as HLA-E, in order to avoid destruction of NK cells, while simultaneously avoiding T cell-mediated destruction by failing to express and present antigens via classical MHC I complexes (HLA-A, HLA-B and HLA-C).

Despite knowledge of tumor immune escape mechanisms, many vaccines have not been designed with countermeasures against these escape mechanisms. As a prime example, it is not uncommon for existing cancer vaccines to target just a single antigen, such as NY-ESO-1, MAGE-3, survivin or CEA, which permits immune escape via escape mechanism #4. As a second example, many cancer vaccines are designed to only target MHC I epitopes by virtue of vaccinating with short (9-10 amino acid) epitope fragments when it is known that longer (~15 amino acid) epitope fragments are required for MHC II presentation, which primes CD4+ helper T cells. CD4+ T helper cells play an essential role in activating both B cells, licensing dendritic cells to prime naive CD8+ T cells and assisting in the formation of memory T cells. Given the profound immune suppression routinely observed in AIDS patients with low CD4+ helper T cell counts, the importance of designing a vaccine, which also activates CD4+ cells, should not be overlooked. Short epitopes, which can only be presented by MHC I molecules, permit immune escape via mechanism #2. In recent years, numerous cancer vaccines, particularly those employing short peptide epitopes, have failed in Phase III clinical trials, as their designs have failed to induce robust and durable immune responses.

The impetus for this disclosure is to improve the efficacy of vaccination therapy for human cancer. Thus, disclosed herein are novel immunogenic compositions, also called MeddieVax, for the treatment of MTC and other human solid tumors harboring the targeted antigens. The disclosed immunogenic compositions have been designed with countermeasures against several immune escape mechanisms. Although this disclosure has particular relevance to MTC, the compositions and methods disclosed herein can be applied to other human cancers, such as human cancers which express the same antigens. In certain embodiments, a disclosed novel immunogenic composition is a vaccine, such as a vaccine for the treatment of MTC and other human solid tumors harboring the targeted antigens.

B. Targeting MTC-Associated Proteins with Immunogenic Epitopes

To be effective, a therapeutic cancer vaccine should elicit a robust immune response against tumor-associated antigens or mutation-derived tumor-specific antigens. To guide selection of target proteins, publicly-available mRNA expression databases were mined in conjunction with a comprehensive literature review to determine viable protein targets. Upon identification of protein targets, the UniProtKP online database was accessed to identify the canonical amino acid sequences for each target protein. Then a number of epitope prediction algorithms were employed to identify specific polypeptide sequences containing epitopes with strong binding affinity for both MHC Class I and MHC Class II molecules, as strong binding is a prerequisite for immunogenicity. In certain instances, epitopes were modified by conservative amino acid substitutions to further enhance predicted MHC binding affinity. Polypeptides were also selected for their predicted ability to serve as B cell epitopes, which is required for antibody production. The novel polypeptide cocktail component of MeddieVax was designed using a comprehensive approach, which was informed by mRNA sequencing, multiple epitope prediction algorithms and immunohistochemical characterization of MTC tumors. As a countermeasure against escape mechanism #4, MeddieVax is designed to provoke a targeted immune response against multiple antigens.

The polypeptide component of MeddieVax establishes antigen targets for immune destruction, but polypeptides alone are insufficiently immunogenic. In fact, when presented without the appropriate stimulatory danger signals (PAMPs), polypeptides can actually promote immune tolerance via induction of regulatory T cells. To elicit a robust immune response, polypeptide vaccines use an adjuvant. In some embodiments, MeddieVax contains a novel adjuvant formulation, which has been empirically verified to prime dendritic cells to secrete immunogenic cytokines and express key surface stimulatory molecules, which are essential to initiating adaptive immune responses. Importantly, the peptides are designed to complex with the adjuvants to enhance production of various cytokines associated with antitumoral immune responses.

On occasion, medullary thyroid carcinomas exhibit a mixed medullary-follicular phenotype. Thus in some embodiments, the compositions and methods disclosed herein are suited for the treatment of medullary thyroid carcinomas having a mixed medullary-follicular phenotype or for well-differentiated thyroid carcinomas or the papillary and follicular kind.

II. Description of Several Embodiments

A. Immunogenic Compositions

Disclosed are immunogenic compositions specifically designed to target tumor associated antigens, and in particular, antigens associated with medullary thyroid carcinoma, papillary thyroid carcinoma and follicular thyroid carcinoma. Although the present disclosure emphasizes medullary thyroid carcinoma, the compositions disclosed herein can also be used in other cancers, for example solid tumors, such as sarcomas and carcinomas, including fibrosarcoma, myxosarcoma, liposarcoma, chondrosarcoma, osteogenic sarcoma and other sarcomas, synovioma, mesothelioma, Ewing's tumor, leiomyosarcoma, rhabdomyosarcoma, colon cancer (such as colon carcinoma), gastric cancer, (for example, gastric adenocarcinoma, such as intestinal type gastric adenocarcinoma and diffuse type gastric adenocarcinoma), lymphoid malignancy, pancreatic cancer, breast cancer (such as adenocarcinoma), lung cancers, gynecological cancers (such as cancers of the uterus (for example endometrial carcinoma), cervix (for example cervical carcinoma, pre-tumor cervical dysplasia), ovaries (for example, ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (for example squamous cell carcinoma, intraepithelial carcinoma, adenocarcinoma, fibrosarcoma, melanoma), vagina (for example clear cell carcinoma, squamous cell carcinoma, botryoid sarcoma), embryonal rhabdomyosarcoma and fallopian tubules (for example carcinoma), prostate cancer, hepatocellular carcinoma, squamous cell carcinoma, basal cell carcinoma, adenocarcinoma, sweat gland carcinoma, analplastic thyroid carcinoma, pheochromocytomas, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma) and skin cancer (such as melanoma and non-melanoma).

On occasion, medullary thyroid carcinomas exhibit a mixed medullary-follicular phenotype, expressing both thyroglobulin and thyroid peroxidase (TPO), which are normally expressed in papillary and follicular thyroid carcinomas. As both thyroglobulin and TPO are highly expressed and likely exclusively expressed in the thyroid, they function as viable targets for therapeutic vaccination. In some embodiments, the disclosed compositions are designed to target tumors expressing thyroglobulin and/or TPO.

An immunogenic composition, such as disclosed herein is composition useful for stimulating or eliciting a specific immune response (or immunogenic response) in a vertebrate. In some embodiments, the immunogenic response is protective or provides protective immunity against cancer. One specific example of a type of immunogenic composition is a vaccine. For in vitro use, the immunogenic composition can consist of the isolated nucleic acid, vector including the nucleic acid/or immunogenic polypeptide. For in vivo use, the immunogenic composition will typically comprise immunogenic polypeptide(s) and/or the nucleic acids encoding the immunogenic polypeptide(s), such as a vector including the nucleic acid, in pharmaceutically acceptable carriers, and/or other agents. An immunogenic composition can optionally include an adjuvant. The disclosed immunogenic compositions include one or more isolated polypeptides, such as a plurality, that, when administered to a subject, elicit an immune response to one or more of RET, HRAS, KRAS, BRAF, calcitonin, carcinoembryonic antigen (CEA), MUC1, MUC4, NY-ESO-1, survivin, indoleamine 2,3-dioxygenase (IDO), HLA-G, brachyury, thyroglobulin, and/or thyroid peroxidase (TPO), and/or mutant forms thereof, such as 2 or more, 3 or more, 4 or more, 5 or more, 6 or more, 7 or more, 8 or more, 9 or more, 10 or more, 11 or more, or 12 or more, 13 or more, 14 or more, or even all 15 of RET, HRAS, KRAS, BRAF, calcitonin, carcinoembryonic antigen (CEA), MUC1, MUC4, NY-ESO-1, survivin, indoleamine 2,3-dioxygenase (IDO), HLA-G, brachyury, thyroglobulin, and/or TPO, and/or mutant forms thereof. In some embodiments, the polypeptides are non-HLA restricted. In some embodiments the polypeptides are HLA restricted, such as HLA-A24, HLA-A1 and HLA-A2 restricted.

In embodiments, an isolated polypeptide that elicits an immune response to a RET polypeptide comprises consists essentially of, and/or consists of, the amino acid sequence set forth as QGRIPVKWTAIESLFDHIYTT (SEQ. ID NO: 2), RENRPPGTFHQFRLLPVQFLCPNISVAYRL (SEQ. ID NO: 3), PX$_1$KWTAIEX$_2$ (SEQ. ID NO: 4), where X$_1$ is Y or T and X$_2$ is Y or I (such as PYKWTAIEI (SEQ. ID NO: 5) or PTKWTAIEY (SEQ. ID NO: 6)), or RLPVKWTAL (SEQ. ID NO: 7). In some embodiments, the sequence set forth as SEQ ID NO: 4 comprises, consists essentially of, and/or consists of, SEQ ID NO: 5 or 6. In some embodiments, an immunogenic composition includes one or more of the polypeptides having the amino acid sequence set forth as one of SEQ ID NOS: 2-7, in any combination. In embodiments, an isolated polypeptide that elicits an immune response to an HRAS polypeptide comprises, consists essentially of, and/or consists of, the amino acid sequence set forth as DGETCLLDILDTAGX$_1$EEYSAMRDQYMRTG (SEQ. ID NO: 11), where X$_1$ can be R or K (such as DGETCLLDILDTAGREEYSAMRDQYMRTG (SEQ. ID NO: 12) or DGETCLLDILDTAGKEEYSAMRDQYMRTG (SEQ. ID NO: 13)), MTEYKLWVGAGRVGKSALTIQLIQ (SEQ. ID NO: 14), or VKDSDDVPMVLVGNNCD-LAARTVESRQAQ (SEQ. ID NO: 15). In some embodiments, the sequence set forth as SEQ ID NO: 11 comprises, consists essentially of, and/or consists of, SEQ ID NO: 12 or 13. In some embodiments, an immunogenic composition includes one or more of the polypeptides having the amino acid sequence set forth as one of SEQ ID NOS: 11-15, in any combination. In embodiments, an isolated polypeptide that elicits an immune response to a KRAS polypeptide comprises, consists essentially of, and/or consists of, the amino acid sequence set forth as DLARSYGIPFIETSVK-TRQRVEDAFYTLV (SEQ. ID NO: 16) or MTEYKLVVVGAX$_1$GVGKSALTIQL (SEQ. ID NO: 17) where X$_1$ can be V or R (such as MTEYKLVWGAVGVGK-SALTIQL (SEQ. ID NO: 18) or MTEYKLVWGARGVGK-SALTIQL (SEQ. ID NO: 19)). In some embodiments, the sequence set forth as SEQ ID NO: 17 comprises, consists essentially of, and/or consists of, SEQ ID NO: 18 or 19. In some embodiments, an immunogenic composition includes one or more of the polypeptides having the amino acid sequence set forth as one of SEQ ID NOS: 16-19, in any combination. In embodiments, an isolated polypeptide that elicits an immune response to a BRAF polypeptide comprises, consists essentially of, and/or consists of, the amino acid sequence set forth as EDLTVKIGDFGLATX$_1$KSRWSGSHQFEQL (SEQ. ID NO: 20), where X$_1$ can be E or K (such as EDLTVKIGD-FGLATEKSRWSGSHQFEQL (SEQ. ID NO: 21), or EDLT-VKIGDFGLATKKSRWSGSHQFEQL (SEQ. ID NO: 22)), or GX$_1$ATX$_2$KSRX$_3$ (SEQ. ID NO: 23) where X$_1$=T, L or Y, X$_2$=E or K, and X$_3$=Y, L, or F (such as (GTATX$_2$KSRY (SEQ. ID NO: 24), where X$_2$=E or K, GLATX$_2$KSRL (SEQ. ID NO: 25), where X$_2$=E or K, or GYATX$_2$KSRF (SEQ. ID NO: 26), where X$_2$=E or K). In some embodiments, the sequence set forth as SEQ ID NO: 20 comprises, consists essentially of, and/or consists of, SEQ ID NO: 21 or 22. In some embodiments, the sequence set forth as SEQ ID NO: 23 comprises, consists essentially of, and/or consists of, SEQ ID NO: 24, 25, or 26. In some embodiments, an immunogenic composition includes one or more of the polypeptides having the amino acid sequence set forth as one of SEQ ID NOS: 20-26, in any combination. In embodiments, an isolated polypeptide that elicits an immune response to a calcitonin polypeptide comprises, consists essentially of, and/or consists of, the amino acid sequence set forth as CTNLSTCMLGTYTQDFNKFHTF-PQTAIGVAAP (SEQ ID NO: 28). In some embodiments, an immunogenic composition includes one or more polypeptides having the amino acid sequence set forth as SEQ. ID NO: 28. In embodiments, an isolated polypeptide that elicits an immune response to a CEA polypeptide comprises, consists essentially of, and/or consists of, the amino acid sequence set forth as TYACFVSNLATGRNNSIVKSIT-VSASGTSP (SEQ. ID NO: 30), LIQNIIQNDTGFYTLH-VIKSDLVNEEAT (SEQ. ID NO: 31), or ITEKNSGLY (SEQ. ID NO: 32). In some embodiments, an immunogenic composition includes the polypeptide having the amino acid sequence set forth as one of SEQ ID NOS: 30-32, in any combination. In embodiments, an isolated polypeptide that elicits an immune response to a MUC1 polypeptide comprises, consists essentially of, and/or consists of, the amino acid sequence set forth as QRDISEMFLQIYKQGGFLGL-SNIKFRPGSVVV (SEQ. ID NO: 35). In some embodiments, an immunogenic composition includes the polypeptide having the amino acid sequence set forth as SEQ ID NO: 35. In embodiments, an isolated polypeptide that elicits an immune response to a MUC4 polypeptide comprises, consists essentially of, and/or consists of, the amino acid sequence set forth as ESDYQIFSYPNPLPSGFT (SEQ. ID NO: 36). In some embodiments, an immunogenic composition includes the polypeptide having the amino acid sequence set forth as SEQ ID NO: 36. In embodiments, an isolated polypeptide that elicits an immune response to a NY-ESO-1 polypeptide comprises, consists essentially of, and/or consists of, the amino acid sequence set forth as GPESRLLEFYLAMPFATPMEAELARRSLAQ (SEQ. ID NO: 38). In some embodiments, an immunogenic composition includes the polypeptide having the amino acid sequence set forth as SEQ ID NO: 38. In embodiments, an isolated polypeptide that elicits an immune response to a survivin polypeptide comprises, consists essentially of, and/or consists of, the amino acid sequence set forth as AFLSVKKQFEELX$_1$LGEFLKX$_2$DRERAKNKIA (SEQ. ID NO: 40), where X$_1$=T, or Y, and X$_2$=L, Y or I (such as AFLSVKKQFEELTLGEFLKLDRERAKNKIA (SEQ. ID NO: 41), AFLSVKKQFEELTLGEFLKYDRERAKNKIA (SEQ. ID NO: 42), AFLSVKKQFEELTLGEFLKIDRE-RAKNKIA (SEQ. ID NO: 43), or AFLSVKKQFEELYLGE-FLKLDRERAKNKIA (SEQ. ID NO: 44)). In some embodiments, the sequence set forth as SEQ ID NO: 40 comprises, consists essentially of, and/or consists of, SEQ ID NOS: 41, 42, 43, or 44. In some embodiments, an immunogenic composition includes one or more of the polypeptides having the amino acid sequence set forth as one of SEQ ID NOS: 40-44, in any combination. In embodiments, an isolated polypeptide that elicits an immune response to an IDO polypeptide comprises, consists essentially of, and/or consists of, the amino acid sequence set forth as PRNIAVPY-CQLSKKLELPPILVYADCVLAN (SEQ. ID NO: 46). In some embodiments, an immunogenic composition includes the polypeptide having the amino acid sequence set forth as SEQ ID NO: 46. In embodiments, an isolated polypeptide that elicits an immune response to a HLA-G polypeptide comprises, consists essentially of, and/or consists of, the amino acid sequence set forth as QTDRLNLQTLRGYYN (SEQ. ID NO: 48). In some embodiments, an immunogenic composition includes the polypeptide having the amino acid sequence set forth as SEQ ID NO: 48. In embodiments, an isolated polypeptide that elicits an immune response to a brachyury polypeptide comprises, consists essentially of, and/or consists of, the amino acid sequence set forth as KLNGGGQIMLNSLHKYEPRIHIVRVGGPQR (SEQ. ID NO: 50). In some embodiments, an immunogenic composition includes the polypeptide having the amino acid sequence set forth as SEQ ID NO: 50. In embodiments an immunogenic composition further includes a polypeptide that, when administered to a subject, elicits an immune response to a mutant passenger protein, the polypeptide comprising, consists essentially of, and/or consists of, the amino acid sequence set forth as SEQ ID NO: 51. In embodiments, an isolated polypeptide that elicits an immune response to a thyroglobulin polypeptide comprises, consists essentially of, and/or consists of, the amino acid sequence set forth as GLELLLDEIYDTIFAGLDLPSTFTETTLY (SEQ ID NO: 53), RLILPQMPKALFRKKVILEDKVKN-FYTRLPFQ (SEQ ID NO: 54), GLREDLLSLQEPGSK-TYSK (SEQ ID NO: 55), or LLLREEATHIYRKPGISLL-SYEASVPSVPIST (SEQ ID NO: 56). In some embodiments, an immunogenic composition includes the polypeptide having the amino acid sequence set forth as one of SEQ ID NOS: 52-56, in any combination. In embodiments, an isolated polypeptide that elicits an immune response to a TPO polypeptide comprises, consists essentially of, and/or consists of, the amino acid sequence set forth as VADKILDLYKHPDNIDVWLGGLAENFLPRA (SEQ ID NO: 58), LLIGGFAGLTSTVICRWTRTGTK-STLPISE (SEQ ID NO: 59), RLRDSGRAYLPFVPPRA-PAACAPEPGIPGE (SEQ ID NO: 60), or QYIDHDIAFT-PQSTSKAAFGGGADCQMTCE (SEQ ID NO: 61). In some embodiments, an immunogenic composition includes the polypeptide having the amino acid sequence set forth as one of SEQ ID NOS: 58-61, in any combination.

In some embodiments, a disclosed composition includes one or more of the polypeptides set forth in Table 2, such as 1 or more SEQ ID NO: 2, SEQ ID NO: 3, SEQ ID NO: 5, SEQ ID NO: 6, SEQ ID NO: 7, SEQ ID NO: 12, SEQ ID NO: 13, SEQ ID NO: 14, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 26, SEQ ID NO: 28, SEQ ID NO: 30, SEQ ID NO: 31, SEQ ID NO: 32, SEQ ID NO: 35, SEQ ID NO: 36, SEQ ID NO: 38, SEQ ID NO: 41, SEQ ID NO: 42, SEQ ID NO: 43, SEQ ID NO: 44, SEQ ID NO: 46, SEQ ID NO: 48, SEQ ID NO: 50, SEQ ID NO: 51, SEQ ID NO: 53, SEQ ID NO: 54, SEQ ID NO: 55, SEQ ID NO: 56, SEQ ID NO: 58, SEQ ID NO: 59, SEQ ID NO: 60, SEQ ID NO: 61, such as 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, or all 40 of SEQ ID NO: 2, SEQ ID NO: 3, SEQ ID NO: 5, SEQ ID NO: 6, SEQ ID NO: 7, SEQ ID NO: 12, SEQ ID NO: 13, SEQ ID NO: 14, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 26, SEQ ID NO: 28, SEQ ID NO: 30, SEQ ID NO: 31, SEQ ID NO: 32, SEQ ID NO: 35, SEQ ID NO: 36, SEQ ID NO: 38, SEQ ID NO: 41, SEQ ID NO: 42, SEQ ID NO: 43, SEQ ID NO: 44, SEQ ID NO: 46, SEQ ID NO: 48, SEQ ID NO: 50, SEQ ID NO: 51, SEQ ID NO: 53, SEQ ID NO: 54, SEQ ID NO: 55, SEQ ID NO: 56, SEQ ID NO: 58, SEQ ID NO: 59, SEQ ID NO: 60, and/or SEQ ID NO: 61, in any combination.

In embodiments, and in particular for use in HLA-A01+ patients with tumors harboring the RET M918T mutation, a disclosed immunogenic composition includes one or more isolated polypeptides, such as a plurality, that, when administered to a subject, elicit an immune response to RET (mutant and/or wildtype), calcitonin, CEA, MUC1, MUC4, NY-ESO-1, survivin, IDO, and brachyury, such as the polypeptides set forth as SEQ ID NOS: 2, 6, 3, 28, 30, 31, 32, 35, 36, 38, 42, 46, and 50. In embodiments, and in particular for use in HLA-A02+ patients with tumors harboring the RET M918T mutation, a disclosed immunogenic composition includes one or more isolated polypeptides, such as a plurality, that, when administered to a subject, elicit an immune response to RET (mutant and/or wildtype), calcitonin, CEA, MUC1, MUC4, NY-ESO-1, survivin, IDO, and brachyury, such as the polypeptides set forth as SEQ ID NOS: 2, 7, 3, 28, 30, 31, 35, 36, 38, 41, 46, and 50. In embodiments, and in particular for use in HLA-A24+ patients with tumors harboring the RET M918T mutation, a disclosed immunogenic composition includes one or more isolated polypeptides, such as a plurality, that, when administered to a subject, elicit an immune response to RET (mutant and/or wildtype), calcitonin, CEA, MUC1, MUC4, NY-ESO-1, survivin, IDO, and brachyury, such as the polypeptides set forth as SEQ ID NOS: 2, 5, 3, 28, 30, 31, 35, 36, 38, 44, 46, and 50. In embodiments, and in particular for use in with tumors with KRAS mutations but not exhibiting thyroglobulin expression, a disclosed immunogenic composition includes one or more isolated polypeptides, such as a plurality, that, when administered to a subject, elicit an immune response to calcitonin, CEA, MUC1, MUC4, NY-ESO-1, survivin, IDO, and brachyury and mutant KRAS, such as the polypeptides set forth as SEQ ID NOS: 28, 30, 31, 32, 35, 36, 38, 41, 46, 50, 16, 18, and 19. In embodiments, and in particular for use in with tumors with HRAS mutations but not exhibiting thyroglobulin expression, a disclosed immunogenic composition includes one or more isolated polypeptides, such as a plurality, that, when administered to a subject, elicit an immune response to calcitonin, CEA, MUC1, MUC4, NY-ESO-1, survivin, IDO, and brachyury and mutant HRAS, such as the polypeptides set forth as SEQ ID NOS: 28, 30, 31, 32, 35, 36, 38, 41, 46, 50, 12, 13, 14, and 15. In embodiments, and in particular for use in HLA-A01+ patients with BRAF mutation harboring tumors expressing thyroglobulin, a disclosed immunogenic composition includes one or more isolated polypeptides, such as a plurality, that, when administered to a subject, elicit an immune response to mutant BRAF, thyroglobulin, TPO, and brachyury, such as the polypeptides set forth as SEQ ID NOS: 21, 22, 24, 53, 54, 55, 56, 58, 59, 60, 61, and 50. In embodiments, and in particular for use in HLA-A02+ patients with BRAF mutation harboring tumors expressing thyroglobulin, a disclosed immunogenic composition includes one or more isolated polypeptides, such as a plurality, that, when administered to a subject, elicit an immune response to mutant BRAF, thyroglobulin, TPO, and brachyury, such as the polypeptides set forth as SEQ ID NOS: 21, 22, 25, 53, 54, 55, 56, 58, 59, 60, 61, and 50. In embodiments, and in particular for use in HLA-A24+ patients with BRAF mutation harboring tumors expressing thyroglobulin, a disclosed immunogenic composition includes one or more isolated polypeptides, such as a plurality, that, when administered to a subject, elicit an immune response to BRAF, thyroglobulin, TPO, and brachyury, such as the polypeptides set forth as SEQ ID NOS: 21, 22, 26, 53, 54, 55, 56, 58, 59, 60, 61, and 50. In embodiments, and in particular for use in patients with HRAS mutation harboring tumors expressing thyroglobulin, a disclosed immunogenic composition includes one or more isolated polypeptides, such as a plurality, that, when administered to a subject, elicit an immune response to mutant HRAS, thyroglobulin, TPO, and brachyury, such as the polypeptides set forth as SEQ ID NOS: 12, 13, 14, 15, 53, 54, 55, 56, 58, 59, 60, 61, and 50. In embodiments, and in particular for use in patients with KRAS mutation harboring tumors expressing thyroglobulin, a disclosed immunogenic composition includes one or more isolated polypeptides, such as a plurality, that, when administered to a subject, elicit an immune response to mutant KRAS, thyroglobulin, TPO, and brachyury, such as the polypeptides set forth as SEQ ID NOS: 16, 18, 19, 53, 54, 55, 56, 58, 59, 60, 61, and 50. In embodiments, and in particular for use in HLA-A24+ patients with BRAF mutation harboring tumors expressing thyroglobulin, a disclosed immunogenic composition includes one or more isolated polypeptides, such as a plurality, that, when administered to a subject, elicit an immune response to mutant BRAF, thyroglobulin, TPO, and brachyury, such as the polypeptides set forth as SEQ ID NOS: 21, 22, 26, 53, 54, 55, 56, 58, 59, 60, 61, and 50. In embodiments, and in particular for use in patients with tumors lacking mutations in RET, BRAF, KRAS and RAS, a disclosed immunogenic composition includes one or more isolated polypeptides, such as a plurality, that, when administered to a subject, elicit an immune response to calcitonin, CEA, MUC1, MUC4, survivin, IDO, and brachyury, such as the polypeptides set forth as 28, 30, 31, 32, 35, 36, 38, 41, 46, and 50.

The disclosed isolated polypeptides include synthetic embodiments of polypeptides described herein. In addition, analogs (non-peptide organic molecules), derivatives (chemically functionalized polypeptide molecules obtained starting with the disclosed polypeptide sequences) and variants (homologs) of these polypeptides can be utilized in the methods described herein. Each polypeptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified polypeptides, and optionally having other desirable properties. For example, peptide sequences with lengths exceeding 19 amino acids, may be reduced in length by 1, 2, 3, 4 5, 6 or 7 amino acids from either the amine end, carboxyl end or both ends of the of the peptide sequence. In another example, carboxylic acid groups of the protein, whether carboxyl-term inal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the polypeptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the polypeptide side chains may be converted to $C_1$-$C_{16}$ alkoxy or to a $C_1$-$C_{16}$ ester using well-recognized techniques. Phenyl and phenolic rings of the polypeptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids.

Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the polypeptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the polypeptide backbone and component amino acid side chains, resulting in such peptido- and organomimetics of an immunogenic polypeptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, Pharmaceutical Biotechnology, Interpharm Press: Buffalo Grove, Ill., pp. 165-174 and Principles of Pharmacology, Munson (ed.) 1995, Ch. 102, for descriptions of techniques used in CADD. Also included are mimetics prepared using such techniques.

In embodiments, an immunogenic polypeptide is included in a fusion protein. For example, any and all of the immunogenic polypeptides included in an immunogenic composition, including a plurality of immunogenic polypeptides, can be in the form of a fusion protein. Thus, the fusion protein can include an immunogenic polypeptide and a second heterologous moiety, such as a myc protein, an enzyme or a carrier (such as a hepatitis carrier protein or bovine serum albumin) covalently linked to the immunogenic polypeptide. A second heterologous moiety can be covalently or non-covalently linked to the immunogenic polypeptide. The immunogenic polypeptides can be included in a fusion protein and can also include heterologous sequences. Thus, in several specific non-limiting examples, one or more of the immunogenic polypeptides are included in a fusion polypeptide, for example a fusion of an immunogenic polypeptide with six sequential histidine residues, a β-galactosidase amino acid sequence, or an immunoglobulin amino acid sequence. The immunogenic polypeptides can also be covalently linked to a carrier. Suitable carriers include, but are not limited to, a hepatitis B small envelope protein HBsAg. This protein has the capacity to self-assemble into aggregates and can form viral-like particles. The preparation of HBsAg is well documented; see for example European Patent Application Publication No. EP-A-0 226 846, European Patent Application Publication No. EP-A-0 299 108 and PCT Publication No. WO 01/117554, and the amino acid sequence disclosed, for example, in Tiollais et al, Nature, 317: 489, 1985, and European Patent Publication No. EP-A-0 278 940, and PCT Publication No. WO 91/14703, all of which are incorporated herein by reference.

A fusion polypeptide can optionally include repetitions of one or more of any of the immunogenic polypeptides disclosed herein. In one specific, non-limiting example, the fusion polypeptide includes two, three, four, five, or up to ten repetitions of a single immunogenic polypeptide. In another example, the fusion polypeptide can optionally include two or more different immunogenic polypeptides disclosed herein. In one specific, non-limiting example, the fusion polypeptide includes two, three, four, five, ten or more different immunogenic polypeptides. A linker sequence can optionally be included between the immunogenic polypeptides.

In embodiments, an immunogenic polypeptide does not include the full-length amino acid sequence of RET, HRAS, KRAS, BRAF, calcitonin, carcinoembryonic antigen (CEA), MUC1, MUC4, NY-ESO-1, survivin, indoleamine 2,3-dioxygenase (IDO), HLA-G, TPO, thyroglobulin or brachyury.

In some embodiments, two or more different disclosed immunogenic polypeptides can be included on a polypeptide, such as an immunogenic molecule. For example, 2-20 or more different immunogenic polypeptides can be included in the polypeptide, such as 2, 3, 4, 5, 6, 7, 8, 9, 10, 11, 12, 13, 14, 15, 16, 17, 18, 19, 20 or more different immunogenic polypeptides. The different immunogenic polypeptides can be separated by a linking molecule, for example polypeptide linkers, or a molecular scaffold.

The compositions described herein can include varying concentrations of each immunogenic polypeptide in a plurality of immunogenic polypeptides.

The immunogenic polypeptides can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al, PNAS 96:5194-97, 1999; Lee et al, J. Immunol. 116: 1711-18, 1976; Dintzis et al, PNAS 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

Nucleic acids encoding one or more of the immunogenic polypeptides are envisioned. These polynucleotides include DNA, cDNA and RNA sequences which encode the polypeptide(s) of interest. Nucleic acid molecules encoding these polypeptides can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same polypeptide.

Nucleic acid sequences encoding one or more of the immunogenic polypeptides can be prepared by any suitable method including, for example, cloning of appropriate sequences or by direct chemical synthesis by methods such as the phosphotriester method of Narang et al, Meth. Enzymol. 68:90-99, 1979; the phosphodiester method of Brown et al, Meth. Enzymol. 68: 109-151, 1979; the diethylphosphoramidite method of Beaucage et al, Tetra. Lett. 22: 1859-1862, 1981; the solid phase phosphoramidite triester method described by Beaucage & Caruthers, Tetra. Letts.

22(20): 1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Exemplary nucleic acids including sequences encoding one or more of the immunogenic polypeptides disclosed herein can be prepared by cloning techniques. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Once the nucleic acids encoding one or more of the immunogenic polypeptides are isolated and cloned, the protein can be expressed in a recombinantly engineered cell such as bacteria, plant, yeast, insect and mammalian cells using a suitable expression vector. One or more DNA sequences encoding one or more immunogenic polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding one or more of the immunogenic polypeptides can be operatively linked to expression control sequences (e.g., a promoter). An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding one or more of the immunogenic polypeptides can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art.

Biologically functional viral and plasmid DNA vectors capable of expression and replication in a host are known in the art.

In embodiments, the immunogenic composition is a vaccine. A vaccine is a pharmaceutical composition that elicits a prophylactic or therapeutic immune response in a subject. In some cases, the immune response is a protective response. Typically, a vaccine elicits an antigen-specific immune response to an antigen of a cell, such as a cancer cell.

C. Therapeutic Formulations

The immunogenic compositions disclosed herein may be included in pharmaceutical compositions (including therapeutic and prophylactic formulations), and may be combined together with one or more pharmaceutically acceptable vehicles and, optionally, other therapeutic ingredients, such as adjuvants.

Such pharmaceutical compositions can be administered to subjects by a variety of administration modes, including by intramuscular, subcutaneous, intravenous, intra-atrial, intra-articular, intraperitoneal, parenteral routes oral, rectal, intranasal, intrapulmonary, or transdermal delivery, or by topical delivery to other surfaces.

To formulate a pharmaceutical composition, the immunogenic compositions can be combined with various pharmaceutically acceptable additives, as well as a base or vehicle for dispersion of the immunogenic compositions. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included.

Adjuvants, such as aluminum hydroxide (for example, AMPHOGEL®, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. In embodiments, a immunogenic composition includes Complete Freund's Adjuvant (CFA), gardiquimod and Poly(I:C).

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The immunogenic compositions can be dispersed in a base or vehicle, which can include a hydrophilic compound having a capacity to disperse the immunogenic composition, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface. The immunogenic composition can be combined with the base or vehicle according to a variety of methods, and release of the immunogenic composition can be by diffusion, disintegration of the vehicle, or associated formation of water channels. In some circumstances, the immunogenic composition is dispersed in microcapsules (microspheres) or nanocapsules (nanospheres) prepared from a suitable polymer, for example, isobutyl 2-cyanoacrylate (see, for example, Michael et al., J. Pharmacy Pharmacol. 43: 1-5, 1991), and dispersed in a biocompatible dispersing medium, which yields sustained delivery and biological activity over a protracted time. The immunogenic compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the immunogenic compositions can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the immunogenic compositions can be brought about by including in the composition an agent which delays absorption, for example, monostearate salts and gelatin.

In certain embodiments, the immunogenic compositions can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various immunogenic compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the immunogenic composition and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body. Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble polypeptides (U.S. Pat. No. 4,675,189).

The pharmaceutical compositions of the disclosure typically are sterile and stable under conditions of manufacture, storage and use. Sterile solutions can be prepared by incorporating the immunogenic compositions in the required amount in an appropriate solvent with one or a combination of ingredients enumerated herein, as required, followed by filtered sterilization. Generally, dispersions are prepared by incorporating the immunogenic composition and/or other biologically active agent into a sterile vehicle that contains a basic dispersion medium and the required other ingredients from those enumerated herein. In the case of sterile powders, methods of preparation include vacuum drying and freeze-drying which yields a powder of the immunogenic composition plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

D. Methods of Treatment

The immunogenic compositions disclosed herein (including immunogenic polypeptides), or nucleic acids encoding the immunogenic polypeptides, polynucleotides encoding such polypeptides and vectors comprising the polynucleotides, can be used in methods of generating or eliciting an immune response, treating a subject with cancer, such as medullary thyroid cancer, and decreasing the growth of a tumor associated medullary thyroid cancer, as described below. In several examples, the subject has medullary thyroid cancer.

In several embodiments, the methods include administering to a subject with an effective amount, such as an immunologically effective dose, of one or more of the immunogenic compositions disclosed in order to generate an immune response. The methods can include selecting a subject in need of treatment, such as a subject that has, is suspected of having, or is predisposed to having cancer, for example a solid tumor, In embodiments, a subject is selected that has or is suspected of having thyroid cancer, such as medullary thyroid carcinoma. Such methods include selecting a subject having or suspected of having cancer, and administering to the subject a therapeutically effective amount of a disclosed immunogenic composition, thereby treating the subject. In embodiments, the cancer is a solid tumor. In embodiments, the cancer comprises thyroid cancer, such as medullary thyroid carcinoma. An immune response is a response of a cell of the immune system, such as a B-cell, T-cell, macrophage or peripheral blood mononuclear cell, to a stimulus. An immune response can include any cell of the body involved in a host defense response. An immune response includes, but is not limited to, an adaptive immune response or inflammation. In some examples, an immune response is stimulated by administering to a subject a vaccine and/or disclosed immunogenic composition.

In exemplary applications, the immunogenic compositions are administered to a subject having a disease, such as cancer (for example, medullary thyroid carcinoma), in an amount sufficient to raise an immune response to cells expressing the antigens targeted by the immunogenic composition. Administration induces a sufficient immune response to slow the proliferation of such cells or to inhibit their growth, or to reduce a sign or a symptom of a tumor. Amounts effective for this use will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer.

In accordance with the various treatment methods of the disclosure, the immunogenic composition can be delivered to a subject in a manner consistent with conventional methodologies associated with management of the disorder for which treatment or prevention is sought. In accordance with the disclosure herein, a prophylactically or therapeutically effective amount of the immunogenic composition and/or other biologically active agent is administered to a subject in need of such treatment for a time and under conditions sufficient to prevent, inhibit, and/or ameliorate a selected disease or condition or one or more symptom(s) thereof, such as cancer, for example medullary thyroid carcinoma.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of as discussed herein, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure. In accordance with these methods and principles, immunogenic compositions and/or other biologically active agent can be administered according to the teachings herein as an independent prophylaxis or treatment program, or as a follow-up, adjunct or coordinate treatment regimen to other treatments, including surgery, vaccination, immunotherapy, hormone treatment, and the like.

The immunogenic compositions can be used in coordinate vaccination protocols or combinatorial formulations. In certain embodiments, novel combinatorial immunogenic compositions and coordinate immunization protocols employ separate immunogens or formulations, each directed toward eliciting a desired immune response. The separate immunogens disclosed herein can be combined in a polyvalent immunogenic composition administered to a subject in a single immunization step, or they can be administered separately (in monovalent immunogenic compositions) in a coordinate immunization protocol.

The administration of the immunogenic compositions of the disclosure can be for either prophylactic or therapeutic purpose. When provided prophylactically, the immunogenic composition is provided in advance of any symptom. The prophylactic administration of the immunogenic composition serves to prevent or ameliorate any progression on the disease. When provided therapeutically, the immunogenic composition is provided at (or shortly after) the onset of a symptom of disease. For prophylactic and therapeutic purposes, the immunogenic compositions can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the immunogenic composition can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the immunogenic composition (for example, amounts that are effective to elicit a desired immune response or alleviate one or more symptoms of a targeted disease). In alternative embodiments, an effective amount or effective dose of the immunogenic compositions may simply inhibit or enhance one or more selected biological activities correlated with a disease or condition, as set forth herein, for either therapeutic or diagnostic purposes.

The actual dosage of the immunogenic compositions will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the immunogenic compositions for eliciting the desired activity or biological response in the subject. Dosage regimens can be adjusted to provide an optimum prophylactic or therapeutic response. A therapeutically effective amount is a quantity of a specific substance (for example, this may be the amount of a disclosed immunogenic composition useful in increasing resistance to, preventing, ameliorating, and/or treating cancer, such as medullary thyroid carcinoma) sufficient to achieve a desired effect in a subject being treated without causing a substantial cytotoxic effect in the subject. For example, a therapeutically effective amount of composition can vary from about 0.01 mg/kg body weight to about 1 g/kg body weight. When administered to a subject, a dosage will generally be used that will achieve target concentrations shown to achieve a desired in vivo effect. A therapeutically effective amount is also one in which any toxic or detrimental side effects of the immunogenic composition and/or other biologically active agent is outweighed in clinical terms by therapeutically beneficial effects. A non-limiting range for a therapeutically effective amount of a the immunogenic composition and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight.

Upon administration of a immunogenic composition of the disclosure (for example, via injection, aerosol, oral, topical or other route), the immune system of the subject typically responds to the immunogenic composition by producing T cells capable of expanding and reacting to the specific antigenic epitopes presented by the immunogenic composition. Such a response signifies that an immunologically effective dose of the immunogenic composition was delivered. An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the immunogenic composition. In some embodiments, the T cell response, as measured by ELISPOT, tetramer staining or intracellular cytokine staining of a subject administered the compositions of the disclosure will be determined in the context of evaluating effective dosages/immunization protocols. In some instances it will be sufficient to assess the percentage of antigen specific T cells and their phenotype via ELISPOT or intracellular cytokine staining. Decisions as to whether to administer booster inoculations and/or to change the amount of the composition administered to the individual can be at least partially based on the ELISPOT data, tetramer staining data or intracellcular cytokine staining data.

Dosage can be varied by the attending clinician to maintain a desired concentration. Higher or lower concentrations can be selected based on the mode of delivery. Dosage can also be adjusted based on the release rate of the administered formulation.

These immunogenic compositions can be used for active immunization, and for preparation of immune antibodies.

The immunogenic compositions are composed of non-toxic components, suitable for infants, children of all ages, and adults.

Kits are also provided. In one embodiment, these kits include a container or formulation that contains one or more of the immunogenic compositions described herein. In one example, this component is formulated in a pharmaceutical preparation for delivery to a subject. The immunogenic composition is optionally contained in a bulk dispensing container or unit or multi-unit dosage form. Optional dispensing means can be provided. Packaging materials optionally include a label or instruction indicating for what treatment purposes and/or in what manner the pharmaceutical agent packaged therewith can be used.

The immunogenic composition of this disclosure can be employed to generate antibodies that recognize the antigens disclosed herein and the antigen from which the disclosed antigen was derived. The methods include administering to a subject immunogenic composition including a disclosed antigen or administering to the subject a polynucleotide encoding a disclosed antigen to generate antibodies that recognize the disclosed antigen. The subject employed in this embodiment is one typically employed for antibody production. Mammals, such as, rodents, rabbits, goats, sheep, etc., are preferred.

The antibodies generated can be either polyclonal or monoclonal antibodies. Polyclonal antibodies are raised by injecting (for example subcutaneous or intramuscular injection) antigenic polypeptides into a suitable animal (for example, a mouse or a rabbit). The antibodies are then obtained from blood samples taken from the animal. The techniques used to produce polyclonal antibodies are extensively described in the literature. Polyclonal antibodies produced by the subjects can be further purified, for example, by binding to and elution from a matrix that is bound with the polypeptide against which the antibodies were raised. Those of skill in the art will know of various standard techniques for purification and/or concentration of polyclonal, as well as monoclonal, antibodies. Monoclonal antibodies can also be generated using techniques known in the art.

E. Synthesis of Polypeptides

The polypeptides used in the disclosed immunogenic compositions can be made by any method available in the art, for example synthesized using solid-phase polypeptide synthesis techniques familiar to those in the art, including Fmoc chemistry, or purification of polypeptides from recombinant prokaryotic or eukaryotic sources.

The disclosed immunogenic compositions can be prepared by cloning techniques. Examples of appropriate cloning and sequencing techniques and instructions sufficient to direct persons of skill through many cloning exercises are found in Sambrook et al, Molecular Cloning: A Laboratory Manual (2nd Ed.), Vols. 1-3, Cold Spring Harbor Laboratory (1989), Berger and Kimmel (eds.), Guide to Molecular Cloning Techniques, Academic Press, Inc., San Diego Calif. (1987) or Ausubel et al. (eds.), Current Protocols in Molecular Biology, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH® laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), INVITROGEN™ (San Diego, Calif.) and Applied Biosystems (Foster City, Calif.), as well as many other commercial sources known to one of skill.

Peptides for the disclosed immunogenic compositions may be produced, for example by chemical synthesis by any of a number of manual or automated methods of synthesis known in the art. In addition, polypeptides that form all or part of a hetero-bifunctional ligand can be produced synthetically. For example, solid phase polypeptide synthesis (SPPS) is carried out on a 0.25 millimole (mmole) scale using an Applied Biosystems Model 43 IA Peptide Synthesizer and using 9-fluorenylmethyloxycarbonyl (Fmoc) amino-terminus protection, coupling with dicyclohexylcarbodiimide/hydroxybenzotriazole or 2-(IH-1-benzo-triazol-1-yl)-1,1,3,3-tetramethyluronium hexafluorophosphate/hydroxybenzotriazole (HBTU/HOBT) and using p-hydroxymethylphenoxymethylpolystyrene (HMP) or Sasrin resin for carboxyl-terminus acids or Rink amide resin for carboxyl-terminus amides. Fmoc-derivatized amino acids are prepared from the appropriate precursor amino acids by tritylation and triphenylmethanol in trifluoroacetic acid, followed by Fmoc derivitization as described by Atherton et al. Solid Phase Peptide Synthesis, IRL Press: Oxford, 1989.

F. Potent Vaccine Adjuvant for MeddieVax

To be safe and effective, a therapeutic cancer vaccine must target self-derived, tumor-specific proteins and elicit a robust immune response. While the polypeptide component of MeddieVax provides the "epitope code" specifying the desired antigens to prime an immune response, polypeptides alone are typically insufficient to provoke a robust immune response. To produce a robust immune response, polypeptide vaccines require a strong adjuvant capable of supplying biochemical danger signals, which alert the immune system to the presence of pathogens. The development of the MeddieVax Adjuvant is now discussed.

In 1898, Dr. William Coley reported a series of case studies whereby bacterial toxins from erysipelas and *bacillus prodigiousus* were injected into the tumors of inoperable sarcoma patients. Remarkably, several patients never recurred and were apparently cured. Over a century later, molecular biology has advanced enough to provide a plausible explanation for this outcome. The bacterial toxins likely disrupted the tumor environment and supplied the requisite "danger signals" via pathogen activated molecular patterns (PAMPs) to activate dendritic cells by promoting expression of CD80 and CD86 and the secretion of key cytokines, including IL-6. The activated dendritic cells could then prime T cells and B cells to carry out their effector functions against tumor cells. Evidently, the lack of an appropriate danger signal may have prevented the initiation of an effective immune response earlier in the course of tumor development as the tumor neoantigens were present prior to bacterial toxin inoculation. Since Coley's initial experiments, our understanding of the immune response has been illuminated by numerous animal models of autoimmune disease, highlighting the biological impact of various adjuvants in polypeptide vaccination.

When deployed with the proper adjuvant, polypeptide vaccines are capable of provoking profound autoimmune responses. Complete Freund's Adjuvant (CFA), consisting of heat-killed *mycobacterium tuberculosis* in non-metabolizable paraffin oil and mannide monooleate, is readily capable of eliciting strong and targeted autoimmune responses. For instance, primates vaccinated with epitopes of myelin oligodendrocyte glycoprotein in CFA often develop fatal autoimmune encephalitis within weeks of injection. Mice vaccinated with CFA and retinal polypeptides subsequently develop blindness due to rapid immune destruction of photoreceptors in their eyes. Rabbits vaccinated with collagen in CFA have been documented to develop symptomatic and crippling arthritis. Furthermore, autoimmune thyroiditis can be readily induced in mice by vaccination of whole protein thyroglobulin in CFA. Conversely, when animals are inoculated with polypeptides in a vehicle lacking any adjuvant function, there is usually no discernible response, and furthermore, future immune responses to such antigens can be dampened even in the presence of a strong adjuvant. Adjuvants are critical elements of a vaccine, as they play an indispensable role in provoking and shaping the immune response.

In cancer, where some degree of immune tolerance has possibly been established, a potent adjuvant is required to prime antigen-presenting cells (APCs) with a "danger signal," in order to break immune tolerance. This concept is analogous to the use of Coley's toxins, which are designed to mimic the natural process of infection, so that antigens can be presented in the appropriate context, in order to engage the immune system. Work on cancer immunotherapy has now spanned three centuries, and it is only in the 21st century that the molecular underpinnings of T cell activation have become well defined.

The adaptive arm of human immune system has intrinsic safeguards to prevent immune responses against self-derived proteins and the development of autoimmune disease. In order to activate effector T cells, antigen-presenting dendritic cells must first be activated with external molecules, which have pathogenic molecular signatures. Toll-like receptors (TLRs) are a major class of dendritic cell surface receptors capable of detecting molecularly conserved microbial complexes. Upon binding of TLR ligands (TLR agonists), TLRs initiate a cascade of intracellular signal events, which activate dendritic cells, priming them to activate effector T cells. TLR ligand binding supplies the required danger signal to induce expression of co-stimulating molecules CD80 and CD86 on dendritic cells and induce secretion of IL-6. CD80 and CD86 serve as activating ligands for the CD28 receptor on T cells, and IL-6 is required for T cells to overcome inhibition by regulatory T cells. The absolute necessity of both CD80/86 expression and IL-6 secretion for dendritic cell activation was only recently discovered by Chandrashekhar Pasare and Ruslan Medzhitov in a series of elegant experiments employing knockout mice. In the absence of either signal, immune tolerance is promoted by dendritic cells.

With ab initio knowledge of the power of CFA to induce profound autoimmune responses, the inventor conducted a set of experiments, in order to evaluate the viability of adding additional adjuvants to CFA, in order to enhance efficacy. CFA, an agonist of TLR2, TLR4 and TLR9, was evaluated alone or in combination with gardiquimod (TLR7 agonist) and Poly(I:C) (TLR3 agonist) supplied from Invitrogen. The adjuvant combinations were evaluated for their ability induce both CD80/CD86 expression on dendritic cells and induce secretion of IL-6. The use of multiple TLR agonists was hypothesized to better mimic the process of natural infection and therefore more potently prime dendritic cells.

In addition to the MeddieVax Adjuvant and administration method discussed in the preceding section, a number of other adjuvants and administration methods may be employed to deliver MeddieVax polypeptides into the patient's body. Other potential adjuvants include, but are not limited to, heat-killed bacteria, mechanically pulverized bacteria, interleukins, aluminum hydroxide, cytosine guanine oligodeoxynucleotide (CpG), RNA oligonucleotides, granulocyte macrophage colony stimulating factor (GM-CSF), saponins, squalene, monophosphoryl lipid A (MPLA), triacylated lipoproteins, other toll-like receptor (TLR) agonists, or recombinant bacteria designed to express the polypeptide components of MeddieVax.

EXAMPLES

Example 1

Design of the MeddieVax Immunogenic Composition

This example describes the development of the MeddieVax immunogenic compositions disclosed herein. A functional description of MeddieVax in the context of rational design and novelty will now be elaborated. The polypeptide component of MeddieVax will first be described followed by a description of the adjuvant.

Identification of Tumor Targets: mRNA Profiling of MTC Cell Line Kinase Activity In order to mine the mechanisms of cellular transformation in MTC, semi-quantitative PCR was used to characterize the relative expression of 42 receptor tyrosine kinases (RTKs) from several available MTC cells lines. MTC TT cells are known to harbor a RET C634W mutation, whereas the MZ-CRC-1 cell line has a RET M918T mutation. The results are shown in Table 1, where relative expression values range from 0 to 100. This approach yielded the following over-activated kinase targets: CSF1R, c-KIT, MET, RET and VEGFR2. All five kinases play essential roles in stem cell renewal and homeostasis. Therefore, targeting all of them is not a viable vaccination strategy due to the potential for severe autoimmune side effects. Of these kinases, only RET has been found to be mutated in a substantial number of MTC tumor specimens, thereby providing a therapeutic window as the antigens encoding the mutated RET kinase can be specifically targeted with its corresponding non-canonical polypeptide sequence.

TABLE 1

Relative mRNA Expression in MTC Cell Lines

| Gene | TT | MZ-CRC-1 | Gene | TT | MZ-CRC-1 |
| --- | --- | --- | --- | --- | --- |
| AXL | 0 | 0 | IDO | 67 | 73 |
| CSF1R | 67 | 60 | IGF1R | 20 | 27 |
| EGFR | 27 | 40 | INSR | 40 | 47 |
| EPHA1 | 0 | 0 | C-KIT | 53 | 73 |
| EPHA2 | 7 | 67 | C-MER | 3 | 20 |
| EPHA3 | 40 | 47 | MET | 47 | 73 |
| EPHA4 | 0 | 0 | MUSK | 0 | 0 |
| EPHA6 | 0 | 7 | NTRK1 | 13 | 0 |
| EPHA7 | 40 | 47 | NTRK2 | 13 | 0 |
| EPHB1 | 33 | 47 | NTRK3 | 33 | 7 |
| EPHB2 | 33 | 33 | PDGFRA | 27 | 27 |
| EPHB4 | 20 | 20 | PDGRFB | 13 | 7 |
| EPHB6 | 7 | 0 | RET | 93 | 100 |
| FGFR1 | 33 | 47 | ROR1 | 40 | 40 |
| FGFR2 | 7 | 7 | ROR2 | 0 | 7 |
| FGFR3 | 0 | 0 | TIE-1 | 0 | 7 |
| FGFR4 | 27 | 27 | TIE-2 | 7 | 7 |
| FLT3 | 0 | 0 | TYRO3 | 13 | 13 |
| HER2/NEU | 13 | 13 | VEGFR1 | 13 | 7 |
| HER3 | 27 | 40 | VEGFR2 | 87 | 93 |
| HER4 | 0 | 13 | VEGFR3 | 0 | 0 |

Prediction Algorithms Used to Engineer MeddieVax

The polypeptide sequences in MeddieVax were engineered using in silico analysis of results from three prediction algorithms. The prediction algorithms were used to predict MHC I and MHC II polypeptide binding affinities as well as capacity of MeddieVax polypeptides to function as linear B cell epitopes. The SYFPEITHI algorithm was used for MHC I binding predictions, while the NetMHCIIpan prediction algorithm was used for MHC II predictions. The LBtope algorithm was used for linear B cell epitope prediction.

Each prediction algorithm employs a unique scoring system to classify MHC binding affinity or B cell epitope probability. For SYFPEITHI, strong MHC I binders are 9-mer polypeptides with a SYFPEITHI score greater than or equal to 20. For NetMHCIIpan, binding affinity results are given in units of nM for 15-mer polypeptides. Strong binders are assumed to have binding values<=100 nM, while weak binders are assigned a cutoff of 500 nM. Polypeptides with binding affinities exceeding 500 nM are classified as non-binders. For LBtope, predication values above 70% are classified as likely B cell epitopes.

Unlike many other human genes, the HLA genes which code for MHC I and MHC II exhibit great diversity among the population, and thus patient response to vaccination may be vary greatly depending on the patient's unique HLA profile. To gauge population-wide immunogenic potential, prediction results are provided for commonly occurring HLA alleles. For MHC I, the HLA A-1, HLA A-2 and HLA-A24 alleles are included as they cover an estimated 70% of the population. MHC I results are given for the 9-mer polypeptide with the maximum SYFPEITHI score for each MeddieVax sequence for each of the three alleles.

For MHC II, the result is computed in the following manner. First, the 15-mer with the highest binding affinity is determined for each allele in a diverse set of six HLA-DR alleles (DRB1*1501, DRB1*0701, DRB1*0301, DRB1*1101, DRB1*1302, DRB1*1202). Then the median is used to generate a single parameter, which serves as an estimate for population-wide HLA-DR binding affinity. There are dozens of HLA-DR alleles, but the six analyzed encompass about 32% of the population and are geographically diverse. As such, they are intended to be representative for sampling purposes. The B cell epitope predications are not allele specific, as B cell binding is determine by somatic hypermutation. To be considered as an MHC II epitope, polypeptide sequences must be at least 13 amino acids in length, and thus 9-mer polypeptides are excluded. Table 3 summarizes the prediction algorithm results for MHC I binding, MHC II Binding and Linear B Cell Probability for MeddieVax Polypeptides The results show that based on advanced prediction algorithms, MeddieVax polypeptides have the capacity to bind to B cell receptors and MHC molecules across multiple HLA allele types, which is a critical component of immunogenicity.

Targeting RET

In agreement with mRNA profiling, numerous studies have established the RET oncogene as a dominant mutational driver in a majority of MTC cases. Sporadic cases account for ~75% of all MTC cases, and a RET mutation is found in majority of sporadic MTC cases. Also, germline RET mutations are found in nearly 100% of genetic MTC cases. In sporadic patients harboring a RET mutation, the RET M918T mutation is most prevalent, while the C634W and C643R mutations are most common in genetic cases. These RET mutations are known to induce constitutive, ligand-free phosphorylation of the RET kinase. Such mutations are particularly oncogenic, as they lead to activation of numerous downstream pathways involved in growth, proliferation, survival and motility, including RAS/RAF/MEK/ERK, PI3K/AKT, NF—KB and STAT3.

While the two FDA-approved therapies inhibit RET at IC50<100 nM concentration, studies have shown that inhibition is only partial at physiologically achievable concentrations and RET's tyrosine residues remain phosphorylated at peak doses. Given the key importance of RET in MTC and the inability to fully inhibit RET with current pharmaceutical regimens MeddieVax was designed to engage the immune system target both mutated and non-mutated portions of the RET protein, as RET is thought to be expressed in all MTC cells, which is in good agreement with mRNA data from Table 1. The canonical RET M918T sequence is provide below.

(SEQ ID NO: 1)
MAKATSGAAGLRLLLLLLLPLLGKVALGLYFSRDAYWEKLYVDQAAGTPL

LYVHALRDAPEEVPSFRLGQHLYGTYRTRLHENNWICIQEDTGLLYLNRS

LDHSSWEKLSVRNRGFPLLTVYLKVFLSPTSLREGECQWPGCARVYFSFF

NTSFPACSSLKPRELCFPETRPSFRIRENRPPGTFHQFRLLPVQFLCPNI

SVAYRLLEGEGLPFRCAPDSLEVSTRWALDREQREKYELVAVCTVHAGAR

EEVVMVPFPVTVYDEDDSAPTFPAGVDTASAVVEFKRKEDTVVATLRVFD

ADVVPASGELVRRYTSTLLPGDTWAQQTFRVEHWPNETSVQANGSFVRAT

VHDYRLVLNRNLSISENRTMQLAVLVNDSDFQGPGAGVLLLHFNVSVLPV

SLHLPSTYSLSVSRRARRFAQIGKVCVENCQAFSGINVQYKLHSSGANCS

TLGVVTSAEDTSGILFVNDTKALRRPKCAELHYMVVATDQQTSRQAQAQL

LVTVEGSYVAEEAGCPLSCAVSKRRLECEECGGLGSPTGRCEWRQGDKG

ITRNFSTCSPSTKTCPDGHCDVVETQDINICPQDCLRGSIVGGHEPGEPR

GIKAGYGTCNCFPEEEKCFCEPEDIQDPLCDELCRTVIAAAVLFSFIVSV

LLSAFCIHCYHKFAHKPPISSAEMTFRRPAQAFPVSYSSSGARRPSLDSM

ENQVSVDAFKILEDPKWEFPRKNLVLGKTLGEGEFGKVVKATAFHLKGRA

GYTTVAVKMLKENASPSELRDLLSEFNVLKQVNHPHVIKLYGACSQDGPL

LLIVEYAKYGSLRGFLRESRKVGPGYLGSGGSRNSSSLDHPDERALTMGD

LISFAWQISQGMQYLAEMKLVHRDLAARNILVAEGRKMKISDFGLSRDVY

EEDSYVKRSQGRIPVKWTAIESLFDHIYTTQSDVWSFGVLLWEIVTLGGN

PYPGIPPERLFNLLKTGHRMERPDNCSEEMYRLMLQCWKQEPDKRPVFAD

ISKDLEKMMVKRRDYLDLAASTPSDSLIYDDGLSEEETPLVDCNNAPLPR

ALPSTWIENKLYGMSDPNWPGESPVPLTRADGTNTGFPRYPNDSVYANWM

LSPSAAKLMDTFDS

The following RET RTK polypeptide sequences were identified as targets for producing an immune response to RET expressing cells:

(SEQ ID NO: 2)
QGRIPVKWTAIESLFDHIYTT (SEQ ID NO: 3)
RENRPPGTFHQFRLLPVQFLCPNISVAYRL (SEQ ID NO: 4)
PX₁KWTAIEX₂, where X₁ is Y or T and X₂ is Y or I, such as (SEQ ID NO: 5)
PYKWTAIEI or (SEQ ID NO: 6)
PTKWTAIEY

(SEQ ID NO: 7)
RLPVKWTAL

SEQ ID NO: 2 is a non-HLA restricted and specifically targets amino acids 910-930 of RET bearing the M918T mutation. SEQ ID NO: 3 targets a hydrophilic extracellular portion of non-mutant RET corresponding to amino acids 176-206, and SEQS. 3-5 are HLA-A24, HLA-A1 and HLA-A2 restricted respectively, and have been modified in the 2nd and C terminal positions to enhance MHC I binding to activate HLA-restricted cytotoxic T cell responses. SEQ ID Nos: 2 and 3 are of sufficient length to activate adaptive immune responses from B cells, cytotoxic T cells and T helper cells.

Targeting RAS and BRAF Mutations

While RET is the most common molecular driver of MTC, present in ~65% of tumor specimens, whole exome sequencing has revealed other mutually exclusive, molecular drivers. Activating point mutations in the RAS GTPases (KRAS and HRAS) as well as BRAF are present in ~20% of MTC cases. All told, RET, RAS or BRAF mutations are found in 85% of MTC tumors. The canonical sequences for HRAS, KRAS and BRAF are provided below.

HRAS:
(SEQ ID NO: 8)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHQYREQI

KRVKDSDDVPMVLVGNKCDLAARTVESRQAQDLARSYGIPYIETSAKTRQ

GVEDAFYTLVREIRQHKLRKLNPPDESGPGCMSCKCVLS

KRAS:
(SEQ ID NO: 9)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

RVEDAFYTLVREIRQYRLKKISKEEKTPGCVKIKKCIIM

BRAF
(SEQ ID NO: 10)
MAALSGGGGGGAEPGQALFNGDMEPEAGAGAGAAASSAADPAIPEEVWNI

KQMIKLTQEHIEALLDKFGGEHNPPSIYLEAYEEYTSKLDALQQREQQLL

ESLGNGTDFSVSSSASMDTVTSSSSSSLSVLPSSLSVFQNPTDVARSNPK

SPQKPIVRVFLPNKQRTVVPARCGVTVRDSLKKALMMRGLIPECCAVYRI

QDGEKKPIGWDTDISWLTGEELHVEVLENVPLTTHNFVRKTFFTLAFCDF

CRKLLFQGFRCQTCGYKFHQRCSTEVPLMCVNYDQLDLLFVSKFFEHHPI

PQEEASLAETALTSGSSPSAPASDSIGPQILTSPSPSKSIPIPQPFRPAD

EDHRNQFGQRDRSSSAPNVHINTIEPVNIDDLIRDQGFRGDGGSTTGLSA

TPPASLPGSLTNVKALQKSPGPQRERKSSSSSEDRNRMKTLGRRDSSDDW

EIPDGQITVGQRIGSGSFGTVYKGKWHGDVAVKMLNVTAPTPQQLQAFKN

-continued

EVGVLRKTRHVNILLFMGYSTKPQLAIVTQWCEGSSLYHHLHIIETKFEM

IKLIDIARQTAQGMDYLHAKSIIHRDLKSNNIFLHEDLTVKIGDFGLATV

KSRWSGSHQFEQLSGSILWMAPEVIRMQDKNPYSFQSDVYAFGIVLYELM

TGQLPYSNINNRDQIIFMVGRGYLSPDLSKVRSNCPKAMKRLMAECLKKK

RDERPLFPQILASIELLARSLPKIHRSASEPSLNRAGFQTEDFSLYACAS

PKTPIQAGGYGAFPVH.

To provide broad coverage against multiple driver mutations, MeddieVax also targets commonly found mutations in RAS and BRAF with the following polypeptide sequences.

(SEQ. ID NO: 11)
DGETCLLDILDTAGX₁EEYSAMRDQYMRTG, where $X_1$ can be R or K, such as SEQ ID NO: 12 or 13.
The HRAS Q61R mutation is targeted with SEQ. ID NO: 12.

(SEQ. ID NO: 12)
DGETCLLDILDTAGREEYSAMRDQYMRTG

The HRAS Q61K mutation is targeted with SEQ. ID NO: 13.

(SEQ. ID NO: 13)
DGETCLLDILDTAGKEEYSAMRDQYMRTG

The HRAS G13R mutation is target with SEQ. ID NO: 14.

(SEQ. ID NO: 14)
MTEYKLVVVGAGRVGKSALTIQLIQ.

The HRAS K117N mutation is targeted with SEQ. ID NO: 15.

(SEQ. ID NO: 15)
VKDSDDVPMVLVGNNCDLAARTVESRQAQ

The KRAS A146V mutation is targeted with SEQ. ID NO: 16.

(SEQ. ID NO: 16)
DLARSYGIPFIETSVKTRQRVEDAFYTLV.

The KRAS mutation at position 12 can be targeted with SEQ. ID NO: 17.

(SEQ. ID NO: 17)
MTEYKLVVVGAX₁GVGKSALTIQL where $X_1$ can be V or R, such as SEQ ID NO: 18 or 19.
The KRAS G12V mutation is targeted with SEQ. ID NO: 18.

(SEQ. ID NO: 18)
MTEYKLVVVGAVGVGKSALTIQL.

The KRAS G12R mutation is targeted with SEQ. ID NO: 19.

(SEQ. ID NO: 19)
MTEYKLVVVGARGVGKSALTIQL

BRAF Mutations at position 600 can be targeted by SEQ ID NO: 20.

(SEQ. ID NO: 20)
EDLTVKIGDFGLATX₁KSRWSGSHQFEQL, where $X_1$ can be E or K, such as SEQ ID NO: 21 or 22.
The BRAF V600E is targeted with SEQ. ID NO: 21.

(SEQ. ID NO: 21)
EDLTVKIGDFGLATEKSRWSGSHQFEQL

The BRAF V600K is targeted with SEQ. ID NO: 22.

(SEQ. ID NO: 22)
EDLTVKIGDFGLATKKSRWSGSHQFEQL

To improve MHC binding relative to the canonical sequence, BRAF mutations are targeted with the following HLA-restricted altered polypeptide ligands, corresponding to V600E and V600K mutations.

(SEQ. ID NO: 23)
GX₁ATX₂KSRX₃ where $X_1$=T, L or Y, $X_2$=E or K, $X_3$=Y, L, or F, such as SEQ ID NO: 24-26.
SEQ. ID NO: 24 is HLA-A1 restricted.

(SEQ. ID NO: 24)
GTATX₂KSRY,

SEQ. ID NO: 25 is HLA-A2 restricted.

(SEQ. ID NO: 25)
GLATX₂KSRL, where $X_2$=E or K.
SEQ. ID NO: 26 is HLA-A24 restricted.

(SEQ. ID NO: 26)
GYATX₂KSRF, where $X_2$=E or K.
Targeting Calcitonin

A primary function of the parafollicular C-cells from which MTC originates is the synthesis and secretion of the 32-amino acid polypeptide hormone calcitonin. As a result, MTC broadly expresses calcitonin and calcitonin levels are elevated in the vast majority of MTC patients. Research has indicated that calcitonin is involved, to some degree, in calcium homeostasis and bone remodeling. Despite its diagnostic importance, calcitonin appears to have very limited physiological activity in adults. Patients who have undergone complete thyroidectomies and have undetectable levels of calcitonin (<2 pg/mL) do not experience overt osteoporosis, while advanced MTC patients with serum calcitonin levels 10,000× normal levels do not experience overt osteopetrosis or calcitonin-induced disruption in calcium homeostasis. This is in direct contrast to parathyroid hormone, where parathyroid carcinomas are known to produce lethal levels of parathyroid hormone, which can fatally disrupt calcium homeostasis.

The canonical sequence for calcitonin is provided below. Calcitonin:

(SEQ ID NO: 27)
CGNLSTCMLGTYTQDFNKFHTFPQTAIGVGAP

Given its exquisite tumor specificity and physiological irrelevance, provoking an autoimmune response to eliminate calcitonin-producing cells could be highly beneficial to MTC patients. MeddieVax is designed to target calcitonin with the following modified-calcitonin polypeptide sequence, whereby side chain glycine residues have been replaced by slightly bulker amino acids at the 2$^{nd}$ and 30$^{th}$ positions. SEQ. ID NO: 28 has been modified from the native form of calcitonin, in order to enhance predicted B cell immunogenicity.

(SEQ. ID NO: 28)
CTNLSTCMLGTYTQDFNKFHTFPQTAIGVAAP

Targeting CEA

Carcinoembryonic antigen (CEA) is a cell surface adhesion molecule, which is frequently overexpressed in MTC. Indeed, CEA is often used alongside calcitonin as a serum tumor marker to monitor disease progression or disease recurrence in MTC patients. The velocity of CEA increase, as indicated by the CEA doubling time, serves as a proxy for tumor growth, and therefore has strong prognostic value. The CEA molecule is intimately involved in the metastatic process. As CEA has a particularly high affinity for fibronectin, CEA is hypothesized to help cells anchor to blood vessels at distant sites and establish metastatic foci. Furthermore, CEA has a high self-affinity and therefore is likely to play a role in tumor formations, by promoting intracellular adhesion.

The canonical CEA sequence is provided below.

(SEQ ID NO: 29)
MESPSAPPHRWCIPWQRLLLTASLLTFWNPPTTAKLTIESTPFNVAEGKE

VLLLVHNLPQHLFGYSVVYKGERVDGNRQIIGYVIGTQQATPGPAYSGRE

IIYPNASLLIQNIIQNDTGFYTLHVIKSDLVNEEATGQFRVYPELPKPSI

SSNNSKPVEDKDAVAFTCEPETQDATYLWWVNNQSLPVSPRLQLSNGNRT

LTLFNVTRNDTASYKCETQNPVSARRSDSVILNVLYGPDAPTISPLNTSY

RSGENLNLSCHAASNPPAQYSWFVNGTFQQSTQELFIPNITVNNSGSYTC

QAHNSDTGLNRTTVTTITVYAEPPKPFITSNNSNPVEDEDAVALTCEPEI

QNTTYLWWVNNQSLPVSPRLQLSNDNRTLTLLSVTRNDVGPYECGIQNKL

SVDHSDPVILNVLYGPDDPTISPSYTYYRPGVNLSLSCHAASNPPAQYSW

LIDGNIQQHTQELFISNITEKNSGLYTCQANNSASGHSRTTVKTITVSAE

LPKPSISSNNSKPVEDKDAVAFTCEPEAQNTTYLWWVNGQSLPVSPRLQL

SNGNRTLTLFNVTRNDARAYVCGIQNSVSANRSDPVTLDVLYGPDTPIIS

PPDSSYLSGANLNLSCHSASNPSPQYSWRINGIPQQHTQVLFIAKITPNN

NGTYACFVSNLATGRNNSIVKSITVSASGTSPGLSAGATVGIMIGVLVGV

A

Given its broad expression in MTC and pathogenic potential, MeddieVax is designed to target CEA. The following polypeptide sequences are employed.

(SEQ. ID NO: 30)
TYACFVSNLATGRNNSIVKSITVSASGTSP (SEQ. ID NO: 31)
LIQNIIQNDTGFYTLHVIKSDLVNEEAT (SEQ. ID NO: 32)
ITEKNSGLY

SEQ ID NOS; 30 and 31 are non-HLA restricted and specifically target amino acids 652-681 and 108-135 of CEA, respectively. SEQ. NO: 32 is HLA-24 restricted and targets amino acids 467-475.

Targeting MUC-1 and MUC-4

MUC1 and MUC4 are members of the mucin-like glycoprotein family. MUC1 and MUC4 are frequently overexpressed in MTC as a result of RET-driven STAT3 activation. MUC1 and MUC4 play oncogenic roles in proliferation, metabolism, invasion, metastasis, and angiogenesis. Specifically, the mucins mediate production of growth factors, influence hypoxic glucose metabolism, and promote metastasis by repressing e-cadherin expression.

MUC4 has been modified to enhance predicted B cell immunogenicity. The canonical sequences for MUC1 and MUC4 are provided below.

MUC1:

(SEQ ID NO: 33)
MTPGTQSPFFLLLLLTVLTVVTGSGHASSTPGGEKETSATQRSSVPSSTE

KNAVSMTSSVLSSHSPGSGSSTTQGQDVTLAPATEPASGSAATWGQDVTS

VPVTRPALGSTTPPAHDVTSAPDNKPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDNRPALGS

TAPPVHNVTSASGSASGSASTLVHNGTSARATTTPASKSTPFSIPSHHSD

TPTTLASHSTKTDASSTHHSSVPPLTSSNHSTSPQLSTGVSFFFLSFHIS

NLQFNSSLEDPSTDYYQELQRDISEMFLQIYKQGGFLGLSNIKFRPGSVV

VQLTLAFREGTINVHDVETQFNQYKTEAASRYNLTISDVSVSDVPFPFSA

QSGAGVPGWGIALLVLVCVLVALAIVYLIALAVCQCRRKNYGQLDIFPAR

DTYHPMSEYPTYHTHGRYVPPSSTDRSPYEKVSAGNGGSSLSYTNPAVAA

TSANL

MUC4:

(SEQ ID NO: 34)

MKGARWRRVPWVSLSCLCLCLLPHVVPGTTEDTLITGSKTAAPVTSTGST

TATLEGQSTAASSRTSNQDISASSQNHQTKSTETTSKAQTDTLTQMMTST

LFSSPSVHNVMETVTQETAPPDEMTTSFPSSVTNTLMMTSKTITMTTSTD

STLGNTEETSTAGTESSTPVTSAVSITAGQEGQSRTTSWRTSIQDTSASS

QNHWTRSTQTTRESQTSTLTHRTTSTPSFSPSVHNVTGTVSQKTSPSGET

ATSSLCSVTNTSMMTSEKITVTTSTGSTLGNPGETSSVPVTGSLMPVTSA

ALVTVDPEGQSPATFSRTSTQDTTAFSKNHQTQSVETTRVSQINTLNTLT

PVTTSTVLSSPSGFNPSGTVSQETFPSGETTISSPSSVSNTFLVTSKVFR

MPISRDSTLGNTEETSLSVSGTISAITSKVSTIWWSDTLSTALSPSSLPP

KISTAFHTQQSEGAETTGRPHERSSFSPGVSQEIFTLHETTTWPSSFSSK

GHTTWSQTELPSTSTGAATRLVTGNPSTRAAGTIPRVPSKVSAIGEPGEP

TTYSSHSTTLPKTTGAGAQTQWTQETGTTGEALLSSPSYSVIQMIKTATS

PSSSPMLDRHTSQQITTAPSTNHSTIHSTSTSPQESPAVSQRGHTRAPQT

TQESQTTRSVSPMTDTKTVTTPGSSFTASGHSPSEIVPQDAPTISAATTF

APAPTGNGHTTQAPTTALQAAPSSHDATLGPSGGTSLSKTGALTLANSVV

STPGGPEGQVVTSASASTSPDTAAAMTHTHQAESTEASGQTQTSEPASSG

SRTTSAGTATPSSSGASGTTPSGSEGISTSGETTRFSSNPSRDSHTTQST

TELLSASASHGAIPVSTGMASSIVPGTFHPTLSEASTAGRPTGQSSPTSP

SASPQETAAISRMAQTQRTGTSRGSDTISLASQATDTFSTVPPTPPSITS

SGLTSPQTQTHTLSPSGSGKTFTTALISNATPLPVTSTSSASTGHATPLA

VSSATSASTVSSDSPLKMETSGMTTPSLKTDGGRRTATSPPPTTSQTIIS

TIPSTAMHTRSTAAPIPILPERGVSLFPYGAGAGDLEFVRRTVDFTSPLF

KPATGFPLGSSLRDSLYFTDNGQIIFPESDYQIFSYPNPLPTGFTGRDPV

ALVAPFWDDADFSTGRGTTFYQEYETFYGEHSLLVQQAESWIRKMTNNGG

YKARWALKVTWVNAHAYPAQWTLGSNTYQAILSTDGSRSYALFLYQSGGM

QWDVAQRSGNPVLMGFSSGDGYFENSPLMSQPVWERYRPDRFLNSNSGLQ

GLQFYRLHREERPNYRLECLQWLKSQPRWPSWGWNQVSCPCSWQQGRRDL

RFQPVSIGRWGLGSRQLCSFTSWRGGVCCSYGPWGEFREGWHVQRPWQLA

QELEPQSWCCRWNDKPYLCALYQQRRPHVGCATYRPPQPAWMFGDPHITT

LDGVSYTFNGLGDFLLVGAQDGNSSFLLQGRTAQTGSAQATNFIAFAAQY

RSSSLGPVTVQWLLEPHDAIRVLLDNQTVTFQPDHEDGGGQETFNATGVL

LSRNGSEVSASFDGWATVSVIALSNILHASASLPPEYQNRTEGLLGVWNN

NPEDDFRMPNGSTIPPGSPEEMLFHFGMTWQINGTGLLGKRNDQLPSNFT

PVFYSQLQKNSSWAEHLISNCDGDSSCIYDTLALRNASIGLHTREVSKNY

EQANATLNQYPPSINGGRVIEAYKGQTTLIQYTSNAEDANFTLRDSCTDL

ELFENGTLLWTPKSLEPFTLEILARSAKIGLASALQPRTVVCHCNAESQC

LYNQTSRVGNSSLEVAGCKCDGGTFGRYCEGSEDACEEPCFPSVHCVPGK

GCEACPPNLTGDGRHCAALGSSFLCQNQSCPVNYCYNQGHCYISQTLGCQ

PMCTCPPAFTDSRCFLAGNNFSPTVNLELPLRVIQLLLSEEENASMAEVN

ASVAYRLGTLDMRAFLRNSQVERIDSAAPASGSPIQHWMVISEFQYRPRG

PVIDFLNNQLLAAVVEAFLYHVPRRSEEPRNDVVFQPISGEDVRDVTALN

VSTLKAYFRCDGYKGYDLVYSPQSGFTCVSPCSRGYCDHGGQCQHLPSGP

RCSCVSFSIYTAWGEHCEHLSMKLDAFFGIFFGALGGLLLLGVGTFVVLR

FWGCSGARFSYFLNSAEALP

MeddieVax is designed to target MUC1 and MUC4 with the following polypeptide sequences.

```
MUC1:
                                       (SEQ. ID NO: 35)
QRDISEMFLQIYKQGGFLGLSNIKFRPGSVVV

MUC4:
                                       (SEQ. ID NO: 36)
ESDYQIFSYPNPLPSGFT
```

Targeting NY-ESO-1

The tumor-associated antigen NY-ESO-1, originally isolated from an esophageal carcinoma specimen, is frequently overexpressed in MTC, but rarely expressed in normal tissue except the testis, which is an immunoprivileged site.

The canonical sequence is provided below.

(SEQ ID NO: 37)

MQAEGRGTGGSTGDADGPGGPGIPDGPGGNAGGPGEAGATGGRGPRGAGA

ARASGPGGGAPRGPHGGAASGLNGCCRCGARGPESRLLEFYLAMPFATPM

EAELARRSLAQDAPPLPVPGVLLKEFTVSGNILTIRLTAADHRQLQLSIS

SCLQQLSLLMWITQCFLPVFLAQPPSGQRR

MeddieVax is designed to target NY-ESO-1 with the following polypeptide sequence, corresponding to amino acids 82-111 of the NY-ESO-1 protein.

(SEQ. ID NO: 38)
GPESRLLEFYLAMPFATPMEAELARRSLAQ

Targeting Survivin

Survivin is a tumor-associated anti-apoptotic protein, which is minimally expressed in normal adult human tissue, but commonly overexpressed by cancer cells. Survivin confers resistance to apoptosis and is thus involved in cancer cell survival. Immunohistochemistry indicates that survivin is broadly expressed in MTC. The canonical survivin sequence is provided below.

Survivin:

(SEQ ID NO: 39)
MGAPTLPPAWQPFLKDHRISTFKNWPFLEGCACTPERMAEAGFIHCPTEN

EPDLAQCFFCFKELEGWEPDDDPIEEHKKHSSGCAFLSVKKQFEELTLGE

FLKLDRERAKNKIAKETNNKKKEFEETAKKVRRAIEQLAAMD

MeddieVax is designed to target survivin with the following sequences.

(SEQ. ID NO: 40)
AFLSVKKQFEELX$_1$LGEFLKX$_2$DRERAKNKIA, where X$_1$=T, or Y, and X$_2$=L, Y or I, such as SEQ ID NO: 41-44.

(SEQ. ID NO: 41)
AFLSVKKQFEELTLGEFLKLDRERAKNKIA (SEQ. ID NO: 42)
AFLSVKKQFEELTLGEFLK<u>Y</u>DRERAKNKIA (SEQ. ID NO: 43)
AFLSVKKQFEELTLGEFLKIDRERAKNKIA (SEQ. ID NO: 44)
AFLSVKKQFEEL<u>Y</u>LGEFLKLDRERAKNKIA

SEQ. ID NO: 39 is designed to target multiple HLA types, whereas SEQ. ID NOs: 40-42 are HLA-A1, HLA-A2 and HLA-A24 restricted, respectively.

Targeting Indoleamine 2,3-Dioxygenase (100):

The enzyme Indoleamine 2,3-dioxygenase (IDO) is overexpressed in MTC, likely as a result of RET-driven STAT3 activation. IDO catalyzes the conversion of tryptophan to kynurenine. As kynurenine suppresses helper T cell proliferation and induces regulatory T cell proliferation, IDO is highly immunosuppressive and is associated with reduced T cell infiltration of tumors. The canonical sequence for the IDO gene is provided below.

IDO:

(SEQ ID NO: 45)
MAHAMENSWTISKEYHIDEEVGFALPNPQENLPDFYNDWMFIAKHLPDLI

ESGQLRERVEKLNMLSIDHLTDHKSQRLARLVLGCITMAYVWGKGHGDVR

KVLPRNIAVPYCQLSKKLELPPILVYADCVLANWKKKDPNKPLTYENMDV

LFSFRDGDCSKGFFLVSLLVEIAAASAIKVIPTVFKAMQMQERDTLLKAL

LEIASCLEKALQVFHQIHDHVNPKAFFSVLRIYLSGWKGNPQLSDGLVYE

GFWEDPKEFAGGSAGQSSVFQCFDVLLGIQQTAGGGHAAQFLQDMRRYMP

PAHRNFLCSLESNPSVREFVLSKGDAGLREAYDACVKALVSLRSYHLQIV

TKYILIPASQQPKENKTSEDPSKLEAKGTGGTDLMNFLKTVRSTTEKSLL

KEG

As a countermeasure against escape mechanism #5, MeddieVax is designed to target IDO with the following sequence.

(SEQ. ID NO: 46)
PRNIAVPYCQLSKKLELPPILVYADCVLAN

Targeting HLA-G

The human leukocyte antigen G (HLA-G) is a non-classic MHC class I molecule, which promotes immune tolerance. Unlike classical MHC class I molecules, (HLA-A, HLA-B and HLA-C), HLA-G exhibits very restricted tissue expression and does not present intracellular polypeptide fragments (antigens) to T cells. Like other MHC molecules, HLA-G serves as a ligand for inhibitory receptors on NK cells. As such, cells exclusively presenting HLA-G are spared destruction by NK, while failing to present antigens to cytotoxic T cells via classic MHC I molecules. In short, cells which exclusively express HLA-G are highly immune to attack from NK cells and cytotoxic T cells.

The prime biological role of HLA-G is maternal-fetal tolerance. The fetal trophoblast broadly expresses HLA-G, thereby preventing destruction by maternal NK cells. To evade destruction by the host's immune system, cancer cells may overexpress HLA-G, while downregulating classical MHC I expression. In doing so, cancer cells cloak themselves from the host immune system by hijacking the same mechanism employed by the developing fetus to avoid rejection from the mother's immune system.

Tumor expression of HLA-G is a negative prognostic indicator, significantly associated with reduced survival. As a countermeasure against HLA-G (escape mechanisms #6), MeddieVax is designed with a unique sequence designed to induce antibodies against HLA-G. The canonical form of HLA-G is provided below.

HLA-G:

(SEQ ID NO. 47)
MVVMAPRTLFLLLSGALTLTETWAGSHSMRYFSAAVSRPGRGEPRFIAM

GYVDDTQFVRFDSDSACPRMEPRAPWVEQEGPEYWEEETRNTKAHAQTDR

MNLQTLRGYYNQSEASSHTLQWMIGCDLGSDGRLLRGYEQYAYDGKDYLA

LNEDLRSWTAADTAAQISKRKCEAANVAEQRRAYLEGTCVEWLHRYLENG

KEMLQRADPPKTHVTHHPVFDYEATLRCWALGFYPAEIILTWQRDGEDQT

QDVELVETRPAGDGTFQKWAAVVVPSGEEQRYTCHVQHEGLPEPLMLRWK

QSSLPTIPIMGIVAGLVVLAAVVTGAAVAAVLWRKKSSD

MeddieVax is designed to target HLA-G with the following polypeptide sequence.

(SEQ. ID NO: 48)
QTDR<u>L</u>NLQTLRGYYN

SEQ. ID NO: 48 codes for the α1 extracellular domain (exon 2), which is found on all membrane-bound and soluble forms of HLA-G. The sequence is modified from its canonical form to enhance predicted B cell immunogenicity. HLA-G displays strong sequence homology to other HLA molecules and perfect sequence homology in many regions of the gene. Notably, SEQ. ID NO: 46 is unique to HLA-G, which is intentionally selected to prevent immune responses from being provoked against other HLA molecules.

Targeting Brachyury

The T Box transcription factor protein brachyury is expressed in thyroid tissues and can be overexpressed in MTC. Brachyury has been implicated in rendering tumor cells resistant to chemotherapy and radiation. Furthermore, molecular evidence indicates that brachyury-derived transcription activities cause epithelial tumor cells to transform into cells with mesenchymal properties. In turn, the associated loss of e-cadherin, among other factors, results in metastasis. The canonical brachyury sequence is provided below.

Brachyury:

(SEQ ID NO: 49)
MSSPGTESAGKSLQYRVDHLLSAVENELQAGSEKGDPTERELRVGLEE

SELWLRFKELTNEMIVTKNGRRMFPVLKVNVSGLDPNAMYSFLLDFVAAD

NHRWKYVNGEWVPGGKPEPQAPSCVYIHPDSPNFGAHWMKAPVSFSKVKL

TNKLNGGGQIMLNSLHKYEPRIHIVRVGGPQRMITSHCFPETQFIAVTAY

QNEEITALKIKYNPFAKAFLDAKERSDHKEMMEEPGDSQQPGYSQWGWLL

PGTSTLCPPANPHPQFGGALSLPSTHSCDRYPTLRSHRSSPYPSPYAHRN

NSPTYSDNSPACLSMLQSHDNWSSLGMPAHPSMLPVSHNASPPTSSSQYP

SLWSVSNGAVTPGSQAAAVSNGLGAQFFRGSPAHYTPLTHPVSAPSSSGS

PLYEGAAAATDIVDSQYDAAAQGRLIASWTPVSPPSM

MeddieVax is designed to target cells overexpressing brachyury with the following sequence.

(SEQ. ID NO: 50)
KLNGGGQIMLNSLHKYEPRIHIVRVGGPQR

Targeting Mutant Passenger Proteins

As each patient's tumor harbors unique mutations, MeddieVax is designed to target those mutations, which can be determined using whole exome sequencing systems, such as the Illumina Hi-Seq. The vaccine is specifically designed to target missense mutations, where changes in DNA result in a single amino being swapped for a different amino acid. For instance, in the common BRAF V600E mutation, a glutamic acid residue (E) is substituted for the native valine residue (V) as a result of a thymine to adenine swap in the codon corresponding to valine. To target such patient specific mutations, MeddieVax employs the following generic 25 amino acid sequence, where U represents the canonical amino acids and X, the lone mutated amino acid. The mutated amino acid, X, is in the center and bordered on each side by 12 canonical amino acids, denoted here by U.

(SEQ. ID NO: 51)
UUUUUUUUUUUUXUUUUUUUUUUUU

Targeting Thyroglobulin and Thyroid Peroxidase

On occasion, medullary thyroid carcinomas exhibit a mixed medullary-follicular phenotype, expressing both thyroglobulin and thyroid peroxidase (TPO), which are normally expressed in papillary and follicular thyroid carcinomas. As both thyroglobulin and TPO are highly expressed and likely exclusively expressed in the thyroid, they function as viable targets for therapeutic vaccination. MeddieVax is designed to target tumors expressing thyroglobulin and/or TPO.

The canonical thyroglobulin sequence is provided below.

Thyroglobulin:

(SEQ ID NO: 52)
MALVLEIFTLLASICWVSANIFEYQVDAQPLRPCELQRETAFLKQADYVP

QCAEDGSFQTVQCQNDGRSCWCVGANGSEVLGSRQPGRPVACLSFCQLQK

QQILLSGYINSTDTSYLPQCQDSGDYAPVQCDVQQVQCWCVDAEGMEVYG

TRQLGRPKRCPRSCEIRNRRLLHGVGDKSPPQCSAEGEFMPVQCKFVNTT

DMMIFDLVHSYNRFPDAFVTFSSFQRRFPEVSGYCHCADSQGRELAETGL

ELLLDEIYDTIFAGLDLPSTFTETTLYRILQRRFLAVQSVISGRFRCPTK

CEVERFTATSFGHPYVPSCRRNGDYQAVQCQTEGPCWCVDAQGKEMHGTR

QQGEPPSCAEGQSCASERQQALSRLYFGTSGYFSQHDLFSSPEKRWASPR

VARFATSCPPTIKELFVDSGLLRPMVEGQSQQFSVSENLLKEAIRAIFPS

RGLARLALQFTTNPKRLQQNLFGGKFLVNVGQFNLSGALGTRGTFNFSQF

FQQLGLASFLNGGRQEDLAKPLSVGLDSNSSTGTPEAAKKDGTMNKPTVG

SFGFEINLQENQNALKFLASLLELPEFLLFLQHAISVPEDVARDLGDVME

TVLSSQTCEQTPERLFVPSCTTEGSYEDVQCFSGECWCVNSWGKELPGSR

VRGGQPRCPTDCEKQRARMQSLMGSQPAGSTLFVPACTSEGHFLPVQCFN

SECYCVDAEGQAIPGTRSAIGKPKKCPTPCQLQSEQAFLRTVQALLSNSS

MLPTLSDTYIPQCSTDGQWRQVQCNGPPEQVFELYQRWEAQNKGQDLTPA

KLLVKIMSYREAASGNFSLFIQSLYEAGQQDVFPVLSQYPSLQDVPLAAL

EGKRPQPRENILLEPYLFWQILNGQLSQYPGSYSDFSTPLAHFDLRNCWC

VDEAGQELEGMRSEPSKLPTCPGSCEEAKLRVLQFIRETEEIVSASNSSR

FPLGESFLVAKGIRLRNEDLGLPPLFPPREAFAEQFLRGSDYAIRLAAQS

TLSFYQRRRFSPDDSAGASALLRSGPYMPQCDAFGSWEPVQCHAGTGHCW

CVDEKGGFIPGSLTARSLQIPQCPTTCEKSRTSGLLSSWKQARSQENPSP

KDLFVPACLETGEYARLQASGAGTWCVDPASGEELRPGSSSSAQCPSLCN

VLKSGVLSRRVSPGYVPACRAEDGGFSPVQCDQAQGSCWCVMDSGEEVPG

TRVTGGQPACESPRCPLPFNASEVVGGTILCETISGPTGSAMQQCQLLCR

QGSWSVFPPGPLICSLESGRWESQLPQPRACQRPQLWQTIQTQGHFQLQL

PPGKMCSADYADLLQTFQVFILDELTARGFCQIQVKTFGTLVSIPVCNNS

SVQVGCLTRERLGVNVTWKSRLEDIPVASLPDLHDIERALVGKDLLGRFT

DLIQSGSFQLHLDSKTFPAETIRFLQGDHFGTSPRTWFGCSEGFYQVLTS

EASQDGLGCVKCPEGSYSQDEECIPCPVGFYQEQAGSLACVPCPVGRTTI

SAGAFSQTHCVTDCQRNEAGLQCDQNGQYRASQKDRGSGKAFCVDGEGRR

LPWWETEAPLEDSQCLMMQKFEKVPESKVIFDANAPVAVRSKVPDSEFPV

MQCLTDCTEDEACSFFTVSTTEPEISCDFYAWTSDNVACMTSDQKRDALG

NSKATSFGSLRCQVKVRSHGQDSPAVYLKKGQGSTTTLQKRFEPTGFQNM

LSGLYNPIVFSASGANLTDAHLFCLLACDRDLCCDGFVLTQVQGGAIICG

LLSSPSVLLCNVKDWMDPSEAWANATCPGVTYDQESHQVILRLGDQEFIK

SLTPLEGTQDTFTNFQQVYLWKDSDMGSRPESMGCRKDTVPRPASPTEAG

LTTELFSPVDLNQVIVNGNQSLSSQKHWLFKHLFSAQQANLWCLSRCVQE

HSFCQLAEITESASLYFTCTLYPEAQVCDDIMESNAQGCRLILPQMPKAL

FRKKVILEDKVKNFYTRLPFQKLMGISIRNKVPMSEKSISNGFFECERRC

DADPCCTGFGFLNVSQLKGGEVTCLTLNSLGIQMCSEENGGAWRILDCGS

PDIEVHTYPFGWYQKPIAQNNAPSFCPLVVLPSLTEKVSLDSWQSLALSS

VVVDPSIRHFDVAHVSTAATSNFSAVRDLCLSECSQHEACLITTLQTQPG

AVRCMFYADTQSCTHSLQGQNCRLLLREEATHIYRKPGISLLSYEASVPS

VPISTHGRLLGRSQAIQVGTSWKQVDQFLGVPYAAPPLAERRFQAPEPLN

-continued

WTGSWDASKPRASCWQPGTRTSTSPGVSEDCLYLNVFIPQNVAPNASVLV

FFHNTMDREESEGWPAIDGSFLAAVGNLIVVTASYRVGVFGFLSSGSGEV

SGNWGLLDQVAALTWVQTHIRGFGGDPRRVSLAADRGGADVASIHLLTAR

ATNSQLFRRAVLMGGSALSPAAVISHERAQQQAIALAKEVSCPMSSSQEV

VSCLRQKPANVLNDAQTKLLAVSGPFHYWGPVIDGHFLREPPARALKRSL

WVEVDLLIGSSQDDGLINRAKAVKQFEESRGRTSSKTAFYQALQNSLGGE

DSDARVEAAATVVYYSLEHSTDDYASFSRALENATRDYFIICPIIDMASA

WAKRARGNVFMYHAPENYGHGSLELLADVQFALGLPFYPAYEGQFSLEEK

SLSLKIMQYFSHFIRSGNPNYPYEFSRKVPTFATPWPDFVPRAGGENYKE

FSELLPNRQGLKKADCSFWSKYISSLKTSADGAKGGQSAESEEEELTAGS

GLREDLLSLQEPGSKTYSK

MeddieVax is designed to target cells expressing thyroglobulin with the following sequences.

(SEQ ID NO: 53)
GLELLLDEIYDTIFAGLDLPSTFTETTLY (SEQ ID NO: 54)
RLILPQMPKALFRKKVILEDKVKNFYTRLPFQ (SEQ ID NO: 55)
GLREDLLSLQEPGSKTYSK (SEQ ID NO: 56)
LLLREEATHIYRKPGISLLSYEASVPSVPIST

The canonical TPO sequence is provided below.

(SEQ ID NO: 57)
MRALAVLSVTLVMACTEAFFPFISRGKELLWGKPEESRVSSVLEESKRL

VDTAMYATMQRNLKKRGILSPAQLLSFSKLPEPTSGVIARAAEIMETSIQ

AMKRKVNLKTQQSQHPTDALSEDLLSIIANMSGCLPYMLPPKCPNTCLAN

KYRPITGACNNRDHPRWGASNTALARWLPPVYEDGFSQPRGWNPGFLYNG

-continued

FPLPPVREVTRHVIQVSNEVVTDDDRYSDLLMAWGQYIDHDIAFTPQSTS

KAAFGGGADCQMTCENQNPCFPIQLPEEARPAAGTACLPFYRSSAACGTG

DQGALFGNLSTANPRQQMNGLTSFLDASTVYGSSPALERQLRNWTSAEGL

LRVHARLRDSGRAYLPFVPPRAPAACAPEPGIPGETRGPCFLAGDGRASE

VPSLTALHTLWLREHNRLAAALKALNAHWSADAVYQEARKVVGALHQIIT

LRDYIPRILGPEAFQQYVGPYEGYDSTANPTVSNVFSTAAFRFGHATIHP

LVRRLDASFQEHPDLPGLWLHQAFFSPWTLLRGGGLDPLIRGLLARPAKL

QVQDQLMNEELTERLFVLSNSSTLDLASINLQRGRDHGLPGYNEWREFCG

LPRLETPADLSTAIASRSVADKILDLYKHPDNIDVWLGGLAENFLPRART

GPLFACLIGKQMKALRDGDWFWWENSHVFTDAQRRELEKHSLSRVICDNT

GLTRVPMDAFQVGKFPEDFESCDSITGMNLEAWRETFPQDDKCGFPESVE

NGDFVHCEESGRRVLVYSCRHGYELQGREQLTCTQEGWDFQPPLCKDVNE

CADGAHPPCHASARCRNTKGGFQCLCADPYELGDDGRTCVDSGRLPRVTW

ISMSLAALLIGGFAGLTSTVICRWTRTGTKSTLPISETGGGTPELRCGKH

QAVGTSPQRAAAQDSEQESAGMEGRDTHRLPRAL

Thyroid Peroxidase is targeted with the following peptide sequences.

(SEQ ID NO: 58)
VADKILDLYKHPDNIDVWLGGLAENFLPRA (SEQ ID NO: 59)
LLIGGFAGLTSTVICRWTRTGTKSTLPISE (SEQ ID NO: 60)
RLRDSGRAYLPFVPPRAPAACAPEPGIPGE (SEQ ID NO: 61)
QYIDHDIAFTPQSTSKAAFGGGADCQMTCE

Summary of Targeted Antigens

Table 2 summarizes the tumor-specific or tumor associated antigens targeted by MeddieVax along with the corresponding epitope(s) for each antigen.

TABLE 2

| Targeted Proteins and Corresponding Exemplary polypeptide Sequences | |
|---|---|
| Mutant RET | QGRIPVKWTAIESLFDHIYTT (SEQ ID NO: 2)<br>PYKWTAIEI (SEQ ID NO: 5)<br>PTKWTAIEY (SEQ ID NO: 6)<br>RLPVKWTAL (SEQ ID NO: 7) |
| Wild-type RET | RENRPPGTFHQFRLLPVQFLCPNISVAYRL (SEQ ID NO: 3) |
| Mutant HRAS | DGETCLLDILDTAGREEYSAMRDQYMRTG (SEQ ID NO: 12)<br>DGETCLLDILDTAGKEEYSAMRDQYMRTG (SEQ ID NO: 13)<br>MTEYKLVVVGAGRVGKSALTIQLIQ (SEQ ID NO: 14)<br>VKDSDDVPMVLVGNNCDLAARTVESRQAQ (SEQ ID NO: 15) |
| Mutant KRAS | DLARSYGIPFIETSVKTRQRVEDAFYTLV (SEQ ID NO: 16)<br>MTEYKLVVVGAVGVGKSALTIQL (SEQ ID NO: 18)<br>MTEYKLVVVGARGVGKSALTIQL (SEQ ID NO: 19) |
| Mutant BRAF | EDLTVKIGDFGLATEKSRWSGSHQFEQL (SEQ ID NO: 21)<br>EDLTVKIGDFGLATKKSRWSGSHQFEQL (SEQ ID NO: 22)<br>GTATXKSRY (SEQ ID NO: 24)<br>GLATXKSRL (SEQ ID NO: 25)<br>GYATXKSRF (SEQ ID NO: 26) |

TABLE 2-continued

Targeted Proteins and Corresponding
Exemplary polypeptide Sequences

| | |
|---|---|
| Calcitonin | CTNLSTCMLGTYTQDFNKFHTFPQTAIGVAAP (SEQ ID NO: 28) |
| CEA | TYACFVSNLATGRNNSIVKSITVSASGTSP (SEQ ID NO: 30)<br>LIQNIIQNDTGFYTLHVIKSDLVNEEAT (SEQ ID NO: 31)<br>ITEKNSGLY (SEQ ID NO: 32) |
| MUC1 | QRDISEMFLQIYKQGGFLGLSNIKFRPGSVVV (SEQ ID NO: 35) |
| MUC4 | ESDYQIFSYPNPLPSGFT (SEQ ID NO: 36) |
| NY-ESO-1 | GPESRLLEFYLAMPFATPMEAELARRSLAQ (SEQ ID NO: 38) |
| Survivin | AFLSVKKQFEELTLGEFLKLDRERAKNKIA (SEQ ID NO: 41)<br>AFLSVKKQFEELTLGEFLKYDRERAKNKIA (SEQ ID NO: 42)<br>AFLSVKKQFEELTLGEFLKIDRERAKNKIA (SEQ ID NO: 43)<br>AFLSVKKQFEELYLGEFLKLDRERAKNKIA (SEQ ID NO: 44) |
| IDO | PRNIAVPYCQLSKKLELPPILVYADCVLAN (SEQ ID NO: 46) |
| HLA-G | QTDRLNLQTLRGYYN (SEQ ID NO: 48) |
| Brachyury | KLNGGGQIMLNSLHKYEPRIHIVRVGGPQR (SEQ ID NO: 50) |
| Mutated Passenger Proteins | UUUUUUUUUUUUXUUUUUUUUUUUU (SEQ ID NO: 51) |
| Thyroglobulin | GLELLLDEIYDTIFAGLDLPSTFTETTLY (SEQ ID NO: 53)<br>RLILPQMPKALFRKKVILEDKVKNFYTRLPFQ (SEQ ID NO: 54)<br>GLREDLLSLQEPGSKTYSK (SEQ ID NO: 55)<br>LLLREEATHIYRKPGISLLSYEASVPSVPIST (SEQ ID NO: 56) |
| TPO | VADKILDLYKHPDNIDVWLGGLAENFLPRA (SEQ ID NO: 58)<br>LLIGGFAGLTSTVICRWTRTGTKSTLPISE (SEQ ID NO: 59)<br>RLRDSGRAYLPFVPPRAPAACAPEPGIPGE (SEQ ID NO: 60)<br>QYIDHDIAFTPQSTSKAAFGGGADCQMTCE (SEQ ID NO: 61) |

TABLE 3

MHC I Binding, MHC II Binding and B Cell Epitope Prediction for MeddieVax polypeptides

| Target Protein | Sequence | HLA-A01 | HLA-A02 | HLA-A24 | MHC II Binding (nM) | B Cell Epitope (%) | SEQ ID NO: |
|---|---|---|---|---|---|---|---|
| RET M918T | QGRIPVKWTAIE SLFDHIYTT | 15 | 25 | 14 | 631 | 72.5 | 2 |
| RET M918T | PYKWTAIEI | 1 | 6 | 19 | | 37.4 | 5 |
| RET M918T | PTKWTAIEY | 22 | 2 | -1 | | 29.3 | 6 |
| RET M918T | RLPVKWTAL | 1 | 22 | 13 | | 24.97 | 7 |
| Wild-type RET | RENRPPGTFHQ FRLLPVQFLCP NISVAYRL | 16 | 21 | 16 | 35 | 64.2 | 3 |
| Mutant HRAS | DGETCLLDILDT AGREEYSAMRD QYMRTG | 19 | 23 | 10 | 993 | 74.8 | 12 |
| Mutant HRAS | DGETCLLDILDT AGKEEYSAMRD QYMRTG | 18 | 23 | 10 | 1324 | 72.6 | 13 |
| Mutant HRAS | MTEYKLVVVGA GRVGKSALTIQ LIQ | 15 | 19 | 14 | 159 | 54.8 | 14 |

TABLE 3-continued

MHC I Binding, MHC II Binding and B Cell Epitope Prediction for MeddieVax polypeptides

| Target Protein | Sequence | HLA-A01 | HLA-A02 | HLA-A24 | MHC II Binding (nM) | B Cell Epitope (%) | SEQ ID NO: |
|---|---|---|---|---|---|---|---|
| Mutant HRAS | VKDSDDVPMVL VGNNCDLAART VESRQAQ | 15 | 23 | 13 | 1055 | 73.5 | 15 |
| Mutant KRAS | DLARSYGIPFIE TSVKTRQRVED AFYTLV | 15 | 20 | 12 | 255 | 76.8 | 16 |
| Mutant KRAS | MTEYKLVVVGA VGVGKSALTIQL | 15 | 21 | 11 | 531 | 58.6 | 18 |
| Mutant KRAS | MTEYKLVVVGA RGVGKSALTIQL | 15 | 19 | 11 | 160 | 70.7 | 19 |
| Mutant BRAF | EDLTVKIGDFGL ATEKSRWSGS HQFEQL | 16 | 17 | 12 | 1314 | 72.3 | 21 |
| Mutant BRAF | EDLTVKIGDFGL ATKKSRWSGS HQFEQL | 11 | 17 | 12 | 627 | 73.6 | 22 |
| Mutant BRAF | GTATXKSRY | 22 | 7 | 0 | | 55.7 | 24 |
| Mutant BRAF | GLATXKSRL | 2 | 23 | 10 | | 36.3 | 25 |
| Mutant BRAF | GYATXKSRF | 1 | 3 | 20 | | 55.8 | 26 |
| Calcitonin | CTNLSTCMLGT YTQDFNKFHTF PQTAIGVAAP | 20 | 17 | 24 | 210 | 74.8 | 28 |
| CEA | TYACFVSNLAT GRNNSIVKSITV SASGTSP | 7 | 18 | 22 | 88 | 71 | 30 |
| CEA | LIQNIIQNDTGFY TLHVIKSDLVNE EAT | 15 | 20 | 14 | 70 | 50.1 | 31 |
| CEA | ITEKNSGLY | 30 | 5 | 3 | — | 43.7 | 32 |
| MUC1 | QRDISEMFLQIY KQGGFLGLSNI KFRPGSVVV | 27 | 19 | 13 | 107 | 71 | 35 |
| MUC4 | ESDYQIFSYPNP LPSGFT | 30 | 21 | 12 | 351 | 78.8 | 36 |
| NY-ESO-1 | GPESRLLEFYL AMPFATPMEAE LARRSLAQ | 16 | 21 | 14 | 149 | 49.7 | 38 |
| Survivin | AFLSVKKQFEE LTLGEFLKLDRE RAKNKIA | 13 | 23 | 19 | 300 | 93.7 | 41 |
| Survivin | AFLSVKKQFEE LTLGEFLKYDR ERAKNKIA | 28 | 17 | 19 | 384 | 87.6 | 42 |
| Survivin | AFLSVKKQFEE LTLGEFLKIDRE RAKNKIA | 13 | 21 | 19 | 300 | 87 | 43 |
| Survivin | AFLSVKKQFEE LYLGEFLKLDR ERAKNKIA | 18 | 19 | 25 | 276 | 88 | 44 |

TABLE 3-continued

MHC I Binding, MHC II Binding and B Cell Epitope Prediction for MeddieVax polypeptides

| Target Protein | Sequence | HLA-A01 | HLA-A02 | HLA-A24 | MHC II Binding (nM) | B Cell Epitope (%) | SEQ ID NO: |
|---|---|---|---|---|---|---|---|
| IDO | PRNIAVPYCQL SKKLELPPILVY ADCVLAN | 21 | 21 | 22 | 277 | 72.9 | 46 |
| HLA-G | QTDRLNLQTLR GYYN | 20 | 16 | 10 | 225 | 64.3 | 48 |
| Thyroglobulin | GLELLLDEIYDT IFAGLDLPSTFT ETTLY | 23 | 25 | 22 | 589 | 63 | 53 |
| Thyroglobulin | RLILPQMPKAL FRKKVILEDKV KNFYTRLPFQ | 26 | 26 | 14 | 142 | 59.1 | 54 |
| Thyroglobulin | GLREDLLSLQE PGSKTYSK | 26 | 30 | 11 | 1330 | 86.7 | 55 |
| Thyroglobulin | LLLREEATHIYR KPGISLLSYEAS VPSVPIST | 24 | 29 | 20 | 152 | 61.7 | 56 |
| TPO | VADKILDLYKH PDNIDVWLGGL AENFLPRA | 27 | 23 | 13 | 1651 | 76.6 | 58 |
| TPO | LLIGGFAGLTST VICRWTRTGTK STLPISE | 8 | 31 | 13 | 843 | 59.7 | 59 |
| TPO | RLRDSGRAYLP FVPPRAPAACA PEPGIPGE | 16 | 18 | 14 | 395 | 61.6 | 60 |
| TPO | QYIDHDIAFTPQ STSKAAFGGGA DCQMTCE | 12 | 20 | 24 | 685 | 62.7 | 61 |
| Brachyury | KLNGGGQIMLN SLHKYEPRIHIV RVGGPQR | 16 | 22 | 14 | 121 | 60.3 | 50 |

Reservation to Modify MeddieVax Polypeptide Composition for Personalized Cancer Therapy Tumors arising from the same cell type in different patients invariably exhibit highly distinct molecular characteristics, relating to both underlying mutations and gene expression, which drive the tumor phenotype. To a lesser degree, tumors within the same patient can exhibit such diversity. Using established methods familiar to those in the art, such as whole exome sequencing, mRNA profiling or immunohistochemical staining, the unique genomic and proteomic expression profile of a patient's tumor specimen can be reliably ascertained. In this context, the MeddieVax vaccine can be formulated, to include various combinations of the epitopes described previously, which are listed in Table 2. By design, this approach will permit tumor-specific or tumor-associated antigens, including immunosuppressive antigens to be targeted, while sparing the patient from any potential side effects related to vaccinating against epitopes absent from the patient's tumor. In one embodiment, the vaccine may include a single polypeptide, such as that for HLA-G. In another embodiment, the vaccine may include polypeptides corresponding to epitopes for calcitonin, CEA and RET M918T. In another embodiment the vaccine may include all of the polypeptides sequences found in Table 2. In general, the vaccine may include any combination of polypeptides in Table 2.

Example 2

Development of a Potent MeddieVax Adjuvant

Dendritic cells from a human donor were isolated using a Human Blood Dendritic Cell Isolation Kit from Miltenyi Biotec®. Cells were then suspended in Dulbecco's Modified Eagle's Medium with 10% FBS and diluted to a concentration of $3\times10^6$ per mL. Cells were then transferred to a sterile, flat-bottom 24 well plate and each plate was filled 0.5 mL of cell medium, corresponding to $1.5\times10^6$ cells. In triplicate, wells were spiked with combinations of the following TLR agonists: Gardiquimod (G), PolyI:C (P), and heat-killed *Mycobacterium tuberculosis* (C) at concentrations of 2 μg/mL, 10 μg/mL and 1 μg/mL, respectively. All seven possible combinations of the three TLR agonists were evaluated, including G, P, C, G/P, C/P, G/C and G/C/P. Of note, C is the active TLR ligand in Complete Freund's Adjuvant (CFA). After addition of the various TLR agonists, cells were incubated for 48 hours in a 5% $CO_2$ environment at 37°

C., after which time sample analysis was performed to quantify secretion of the activating cytokine IL-6 and expression of co-stimulating surface molecules CD80 and CD86.

Figure 2:
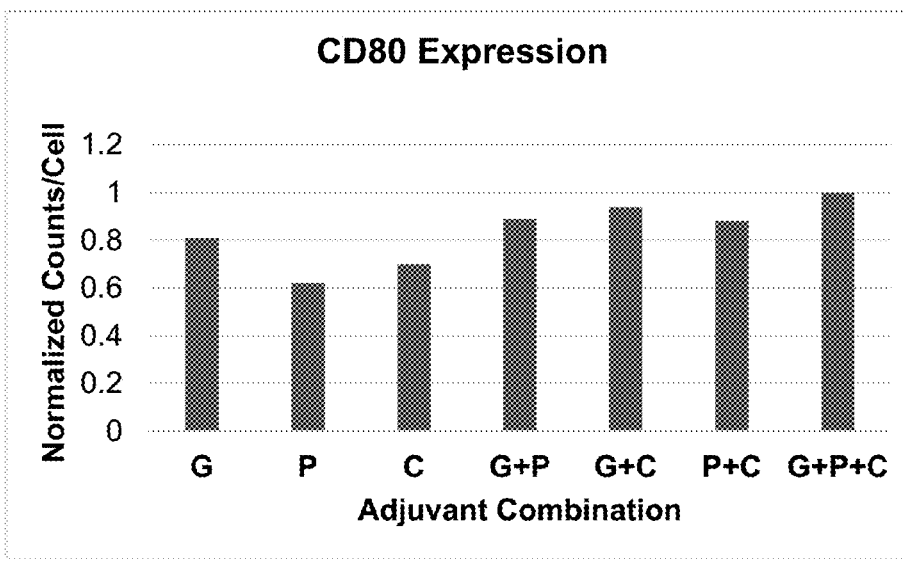
FIG. 2 is a bar graph showing CD80 expression by human dendritic cells primed by various TLR agonists.
Figure 3:
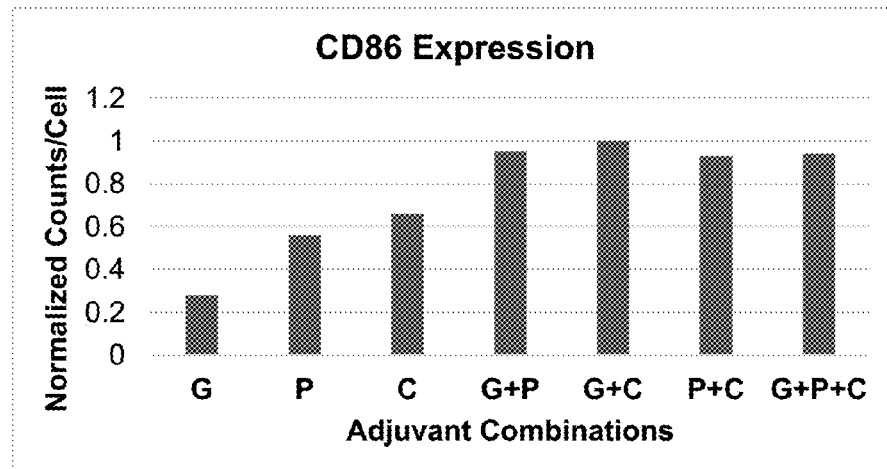
FIG. 3 is a bar graph showing CD86 expression by human dendritic cells primed by various TLR agonists.

ELISA was performed to quantify IL-6 concentration after 1:10 dilutions of each well sample (FIG. 1). After incubating cells with either FITC-conjugated anti-CD86 or FITC-conjugated anti-CD80, the relative expression of CD80 (FIG. 2) and CD86 (FIG. 3) was determined using a 10-bit CCD camera and ImageJ software, whereby the total number of counts is divided by the number of cells in each imaged field, to derive the average number of counts per cell, which is a proxy for CD80/CD86 activation marker expression. For sampling purposes, five random fields were examined for each TLR agonist combo.

Of note, the triplet cocktail of Gardiquimod+PolyI:C+ *Mycobacterium tuberculosis* exhibited a greater increase than would be expected by purely additive effects of each TLR agonist alone, thereby implying a synergy of the triple cocktail. While CFA can be used once for prime vaccination dose, its use in subsequent boosting is not recommended. Clinical trials dating back to 1970 indicate that secondary vaccination with CFA often leads to the formation of painful sterile abscesses.

Based on these experiments, the MeddieVax priming adjuvant is comprised of a novel combination of Freund's Complete Adjuvant (CFA), gardiquimod and PolyI:C, which forms an oil-water liquid emulsion into which the immunogenic polypeptides are suspended. The MeddieVax adjuvant for the prime dose consists of G+P+CFA. As repeated vaccination with CFA is known to occasionally form sterile abscess, this can be avoided by using G+P for subsequent boosting doses, if it is deemed clinically necessary to avoid abscess formation.

Example 3

Vaccine Delivery and Dosing

The MeddieVax vaccine is formulated to be administered as an emulsion, whereby a water and oil suspension formed by polypeptides and adjuvant components (P+G) are dissolved in PBS and vigorously intermixed with CFA (prime dose) or incomplete Freund's Adjuvant (boosting doses) using the two syringe method or other methods. Such methods may include using a homogenizer, vortexer, sonicator or other mixing equipment. As one example, MeddieVax can be administered to the patient via intradermal injection in multiple body locations, which are ideally in close proximity to cervical, inguinal, mediastinal or axillary draining lymph nodes. The total dose of each polypeptide can be varied. In general, the dose of each polypeptide should be 10-10,000 micrograms with a preferred dose of 1,000 micrograms. While intradermal administration is preferred, alternate methods may be employed, including subcutaneous and intramuscular injections. Other administration methods, which do not involve the use of needles may be employed. As an example, polypeptides encapsulated in lipid-based or hydrophobic nanoparticles may be administered via oral ingestion or inhalation. The dose of each polypeptide can be varied depending on the exact method of administration.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

Example 4

Efficacy and Immunogenicity of MeddieVax

The efficacy and immunogenicity of the disclosed MeddieVax therapeutic vaccine was empirically validated in a syngeneic murine tumor model using the p25OE MTC cell line. The experiment was conducted as follows.

Vaccine Preparation

The vaccine and adjuvant only mixture were prepared as follows. First, the following peptides were synthesized by Lifetein (Hillsborough, N.J.) at 98% purity:

(SEQ. ID NO: 2)
QGRIPVKWTAIESLFDHIYTT
and (SEQ. ID NO: 28)
CTNLSTCMLGTYTQDFNKFHTFPQTAIGVAAP.

Of note, the modified calcitonin sequence (SEQ ID NO: 28) and the mutant RET sequence (SEQ ID NO: 2) both exhibit very strong sequence homology (>90%) to their respective murine sequences.

Each peptide was dissolved at a concentration of 1 mg/mL in 1 mL of PBS. The peptide solutions were then mixed together to form a 2 mL solution. After vortexing, the peptide solution containing both sequences was divided into two equal 1 mL volumes. The first volume was used to make the prime part of the vaccine and the second volume was used to make the boost. To make MeddieVax Prime, 1 mL of peptide solution was drawn into a 3 mL glass syringe and emulsified in Complete Freund's Adjuvant (Invivogen, San Diego, Calif.) by vigorously mixing using the two-syringed method, whereby a second 3 mL glass syringe was filled with 1 mL of CFA and the syringes were connected using a 23-gauge connector. The aqueous solution was injected into the CFA and then the mixture was passed back and forth for several minutes, in order to form a stable emulsion. The method yielded 2 mL of MeddieVax Prime. To make MeddieVax Boost, 1 mL of peptide solution was added to a 1 mL solution containing low molecular weight PolyI:C at 1 mg/mL and gardiquimod at 1 mg/mL, generating a 2 mL aqueous solution. This 2 mL solution was then emulsified in 2 mL of Incomplete Freund's Adjuvant (IFA) using the two-syringe method to make 4 mL of MeddieVax Boost. PolyI:C, gardiquimod and IFA were all supplied by Invivogen. Prior to injection, the vaccine and adjuvant cocktails were stored at 4° C. The adjuvant only cocktails (Adjuvant Prime and Adjuvant Boost) were manufactured using the same protocol as the vaccine (peptide plus adjuvant), except no peptides were dissolved in PBS prior to mixing with the adjuvants (CFA or PolyI:C, gardiquimod and IFA).

Expansion of Syngeneic Tumor Cells

To generate sufficient numbers of cells for inoculation, the frozen p25OE cells were thawed in a water bath and rinsed with PBS. Then the cells were expanded in 75 cm$^2$ culture flasks in an incubator at 37° C./5% $CO_2$ in RPMI supplemented with 10% fetal bovine serum (FBS), 20 mM of HEPES and 1 mM of sodium pyruvate and 20 mM of glucose. The cells were noted to grow in suspension, and cells were counted using a hemocytometer and trypan blue exclusion staining. A doubling time of 2-3 days was noted.

Once the cell count reached approximately 150 million, mice were inoculated to generate tumors. For the experiment, 20 female C57BL/6 mice were each injected with 5 million p25OE cells in 20% Matrigel/80% PBS in the left hind flank. The total injection volume was 200 µL per mouse.

Experimental Design and Treatment

Once tumors grew to a volume of approximately 125 mm$^3$, 15 mice were randomized into the following three treatment groups each consisting of five mice: MeddieVax vaccine (peptide plus adjuvant), Adjuvant Alone and untreated control. The day of randomization is considered Day #1.

Treatment Regimen

Mice in the MeddieVax vaccine group were injected with MeddieVax Prime on Day #1, and then injected with MeddieVax Boost on Days 5, 9 and 15. Mice in the MeddieVax vaccine group were injected with MeddieVax Prime on Day #1, and then injected with MeddieVax Boost on Days 5, 9 and 15. Mice in the Adjuvant Alone vaccine group were injected with Adjuvant Prime on Day #1, and then injected with Adjuvant Boost on Days 5, 9 and 15. A volume of 100 µL was used for all injections, which employed a 22-gauge needle. Mice in the Control group were injected with equal volumes of PBS on days 1, 5, 9 and 15. Tumor volumes were measured 3×/week for six weeks.

Results: Vaccine Efficacy

Figure 4:
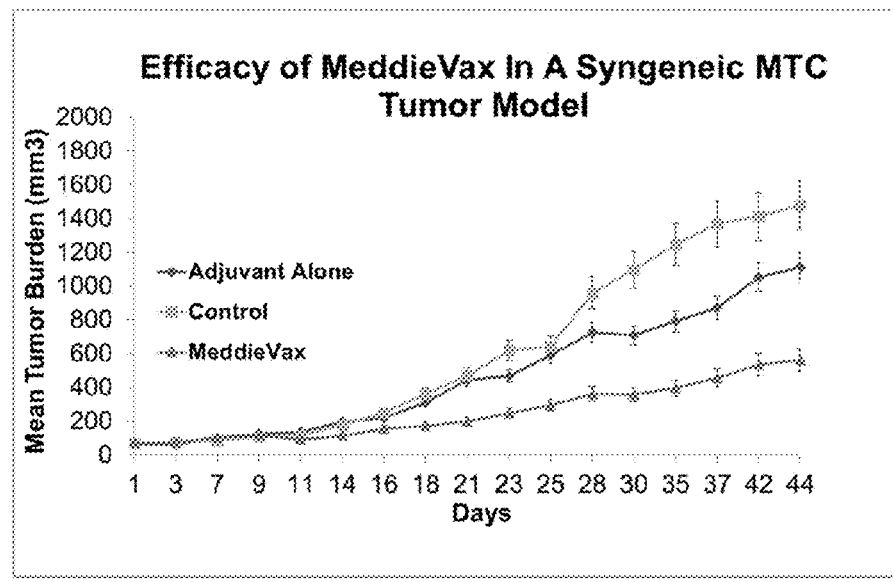
FIG. 4 is a plot demonstrating tumor growth inhibition in a murine syngeneic tumor model of MTC by a disclosed immunogenic composition

Experimental results demonstrate that the disclosed vaccine is immunogenic and significantly inhibits tumor growth. As shown in FIG. 4, MeddieVax significantly inhibited mean tumor growth relative to the Adjuvant Alone and Control groups by 50% ($p<0.01$) and 62% ($p<0.01$), respectively. At day 44, the mean tumor volume in the MeddieVax, Adjuvant Alone and Control groups was 560, 1111, and 1480 mm$^3$, respectively.

To evaluate the immunogenicity of the vaccine, an IFN-gamma ELISPOT assay was performed according to the manufacturer's instructions (Immunospot, Shaker Heights, Ohio). The web-based NetMHCpan 4.0 epitope prediction algorithm (http://www.cbs.dtu.dk/services/NetMHC/) was used to predict murine epitopes contained within the two peptides used for immunization. The epitopes with the strongest predicted MHC I binding affinity for each vaccination peptide were used for ELISPOT assays: TNLSTCML (calcitonin) and RIPVKWTAI (RET). For each mouse group and each peptide, assays were run in triplicate.

Figure 5:
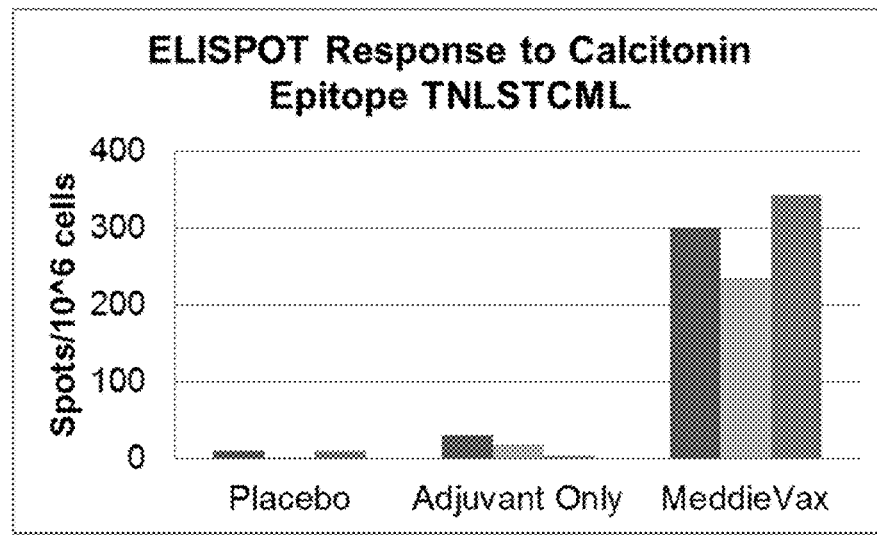
FIG. 5 is a bar graph of murine ELISPOT data which characterizes the immune response to the epitope TNL-STCML in both treatment and control groups
Figure 6:
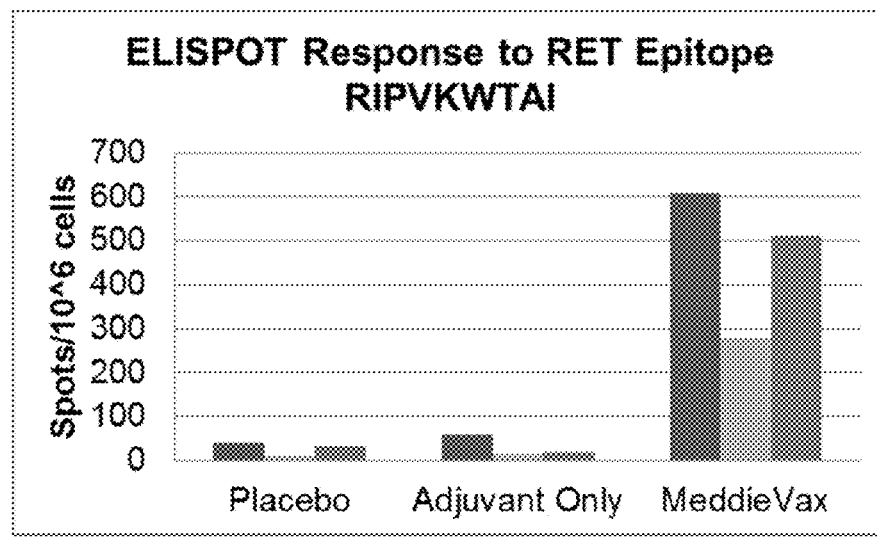
FIG. 6 is a bar graph of murine ELISPOT data which characterizes the immune response to the epitope RIPVK-WTAI in both treatment and control groups

Mice were sacrificed on Day 45. Blood from each of the three experimental groups was pooled and peripheral blood mononuclear cells were isolated using a Ficoll-Paque gradient and centrifugation. After washing twice in PBS, cells were re-suspended in ELISPOT assay medium at a concentration of 2 million cells/mL and then plated into assay wells in 100 µL volumes (200,000 cells/well). Each of the two predicted epitopes was suspended in ELISPOT assay medium at a concentration of 10 µg/mL and then 100 µL volumes were added to each well. The cells were incubated for 24 hours and then the ELISPOT wells were developed per kit instructions. The number of spots per well, corresponding to the total number of IFN-gamma secreting cells was measured using an Immunospot Analyzer. The results are plotted TNLSTCML in FIG. 5 and RIPVKWTAI in FIG. 6. Notably, a strong immune response was present over 20 days since the final boosting vaccination for both epitopes, indicating the presence of cytotoxic T cells expanded due to therapeutic vaccination. Whereas, less than 25 spots/million cells were observed in all three triplicate wells for both control and adjuvant only groups, a peak response of 320 cells/million was observed for the TNLSTCML epitope and 600 cells/million for the RIPVKWTAI epitope, providing strong evidence that the vaccine is immunogenic, increasing the magnitude of T cell responses to each epitope by more than ten-fold.

The combined tumor growth inhibition data and ELISPOT data demonstrate the efficacy and immunogenicity of the disclosed MeddieVax vaccine in a relevant syngeneic tumor model.

The invention claimed is:

1. A method of treating a subject who has medullary thyroid cancer by administering to the subject an immunogenic composition, which comprises SEQ ID NO: 2 in a suitable carrier and/or adjuvant.

2. A method of treating a subject who has medullary thyroid cancer by administering to the subject an immunogenic composition, which consists of SEQ ID NO: 2 and SEQ. ID NO: 28 in a suitable carrier and/or adjuvant.

3. The method of claim 1, whereby SEQ ID NO: 2 may be truncated by 1, 2, 3, 4, 5, 6 or 7 amino acids at either the amino terminus or carboxy terminus.

4. A method of claim 2, whereby either SEQ ID NO: 2 and/or SEQ. ID NO: 28 may be truncated by 1, 2, 3, 4, 5, 6 or 7 amino acids at either the amino terminus or carboxy terminus.

5. A method of treating a subject who has medullary thyroid cancer by administering to the subject an immunogenic composition, which comprises cDNA or mRNA encoding SEQ. ID NO: 2.

6. A method of treating a subject who has medullary thyroid cancer by administering to the subject an immunogenic composition, which consists of cDNA or mRNA encoding SEQ. ID NO: 2 and SEQ. ID NO: 28.

* * * * *